United States Patent
Bowman-Colin et al.

(10) Patent No.: US 12,371,709 B2
(45) Date of Patent: Jul. 29, 2025

(54) MULTIFUNCTIONAL NUCLEIC ACID REPORTER CONSTRUCTS

(71) Applicant: DANA-FARBER CANCER INSTITUTE, INC., Boston, MA (US)

(72) Inventors: Christian Bowman-Colin, Boston, MA (US); David M. Livingston, Brookline, MA (US); Laura C. Wong, South Grafton, MA (US); Shweta Kitchloo, North Attleboro, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 1318 days.

(21) Appl. No.: 17/047,615

(22) PCT Filed: Apr. 19, 2019

(86) PCT No.: PCT/US2019/028378
§ 371 (c)(1),
(2) Date: Oct. 14, 2020

(87) PCT Pub. No.: WO2019/204767
PCT Pub. Date: Oct. 24, 2019

(65) Prior Publication Data
US 2021/0123072 A1 Apr. 29, 2021

Related U.S. Application Data

(60) Provisional application No. 62/660,539, filed on Apr. 20, 2018.

(51) Int. Cl.
*C12N 15/85* (2006.01)
*C12Q 1/6897* (2018.01)

(52) U.S. Cl.
CPC .......... *C12N 15/85* (2013.01); *C12Q 1/6897* (2013.01); *C12N 2310/20* (2017.05); *C12N 2800/80* (2013.01); *C12N 2830/36* (2013.01); *C12N 2830/50* (2013.01); *C12N 2840/203* (2013.01)

(58) Field of Classification Search
CPC ................ C12N 15/85; C12N 2310/20; C12N 2800/80; C12N 2830/36; C12N 2830/50; C12N 2840/203; C12Q 1/6897
See application file for complete search history.

(56) References Cited

U.S. PATENT DOCUMENTS

2004/0171154 A1 9/2004 Storici et al.
2017/0166912 A1 6/2017 Brower-Toland et al.

FOREIGN PATENT DOCUMENTS

WO WO2017147056 8/2017
WO WO-2018014005 A1 * 1/2018 ......... C07K 14/4728

OTHER PUBLICATIONS

Gomez-Cabello et al., "New Tools to Study DNA Double-Strand Break Repair Pathway Choice," PLOS ONE, vol. 8, Published Oct. 2013, pp. 1-9. (Year: 2013).*
Weinstock et al., "Assaying Double-Strand Break Repair Pathway Choice in Mammalian Cells Using a Targeted Endonuclease or the RAG Recombinase", Methods in Enzymology, vol. 409, 2006, pp. 524-538. (Year: 2006).*
Gunn et al., "I-SceI-Based Assays to Examine Distinct Repair Outcomes of Mammalian Chromosomal Double Strand Breaks", DNA Repair Protocols, Methods in Molecular Biology, vol. 920, Chapter 27, 2012, pp. 379-390. (Year: 2012).*
Nagel et al., "Multiplexed DNA Repair assays for multiple lesions and multiple doses via transcription inhibition and transcriptional mutagenesis", PNAS, Published Apr. 22, 2014, pp. E1823-E1832) (Year: 2014).*
Bindra et al., "Development of an assay to measure mutagenic non-homologous end-joining repair activity in mammalian cells", Nucleic Acids Res, vol. 41, Published Apr. 12, 2013, pp. 1-15. (Year: 2013).*
Decottignies, "Microhomology-Mediated End Joining in Fission Yeast Is Repressed by Pku70 and Relies on Genes Involved in Homologous Recobination", Genetics 176 Jul. 2007, pp. 1403-1415. (Year: 2007).*
Ayora et al., "Double-strand break repair in bacteria: a view from Bacillus subtilis", FEMS Microbiol. Rev. vol. 35, 2011, pp. 1055-1081. (Year: 2011).*
Sfeir at al., "Microhomology-mediated end joining: a back-up survival mechanism or dedicated pathway?", Trends Biochem Sci., Nov. 2015, pp. 704-714. (Year: 2015).*
PCT Application No. PCT/US19/28378 International Search Report and Written Opinion, dated Jul. 12, 2019, 13 pages.
PCT Application No. PCT/US19/28378 International Preliminary Report on Patentability, dated Oct. 20, 2020, 9 pages.
Kostyrko et al. "Assays for DNA double-strand break repair by microhomoloy-based end-joining repair mechanisms," Nucleic Acids Res, Dec. 10, 2015, vol. 44, e56, pp. 1-9, entire document.
Mao et al. "Sirtuin 6 (SIRT6) rescues the decline of homologous recombination repair during replicative senescence," Proc Natl Acad Sci USA, Jul. 2, 2012, vol. 109, pp. 11800-11805, entire document.
Xue et al. "A targeted neuroglial reporter line generated by homologous recombination in human embryonic stem cells," Stem Cells, Aug. 1, 2009, vol. 27, pp. 1836-1846, entire document.

(Continued)

*Primary Examiner* — Abigail Vanhorn
*Assistant Examiner* — Stephanie L Sullivan
(74) *Attorney, Agent, or Firm* — Mueting Raasch Group

(57) ABSTRACT

Nucleic acids comprising multifunctional double-stranded break reporter constructs for stable or transient transfection into a cell, as well as detecting a type of double-stranded break repair mechanism in a cell. Methods for detecting types of double-stranded break repair mechanism in a cell, as well as vectors and cells comprising nucleic acids comprising multifunctional double-stranded break reporter constructs.

20 Claims, 39 Drawing Sheets

Specification includes a Sequence Listing.

(56) References Cited

OTHER PUBLICATIONS

Yang et al. "One-step generation of mice carrying reporter and conditional alleles by CRISPR/Cas-mediated genome engineering," Cell, Aug. 29, 2013, vol. 154, pp. 1370-1379, entire document.

* cited by examiner

| uncut | NHEJ | HR | MMEJ | SSA |
|---|---|---|---|---|
| No color | Orange | Green & Orange | Blue & Orange | Maroon |
| • GFP-<br>• BFP-<br>• tdTomato-<br>• iRFP670- | • GFP-<br>• BFP-<br>• tdTomato+<br>• iRFP670- | • GFP+<br>• BFP-<br>• tdTomato+<br>• iRFP670- | • GFP-<br>• BFP+<br>• tdTomato+<br>• iRFP670- | • GFP-<br>• BFP-<br>• tdTomato-<br>• iRFP670+ |

FIG. 3G

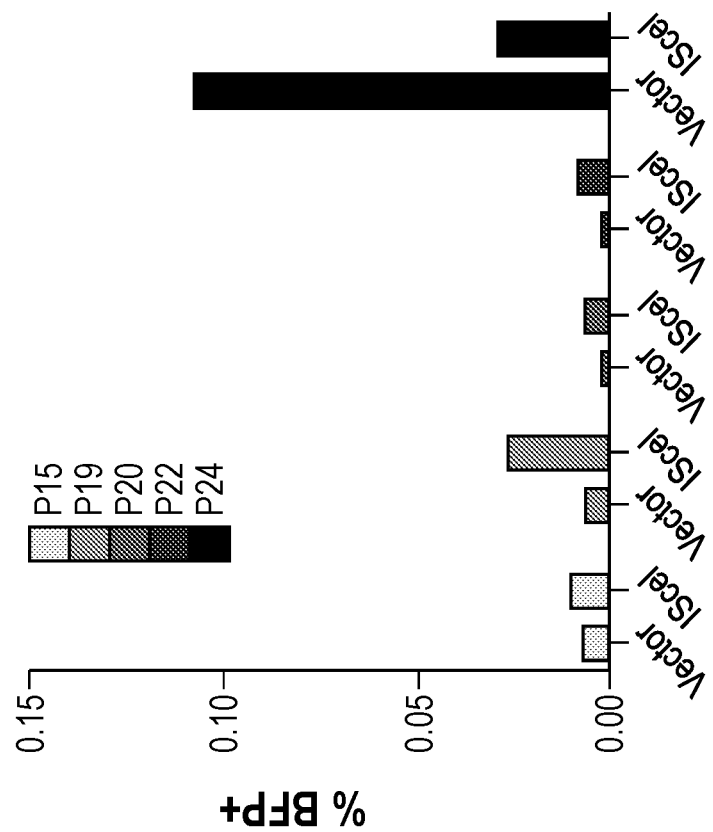
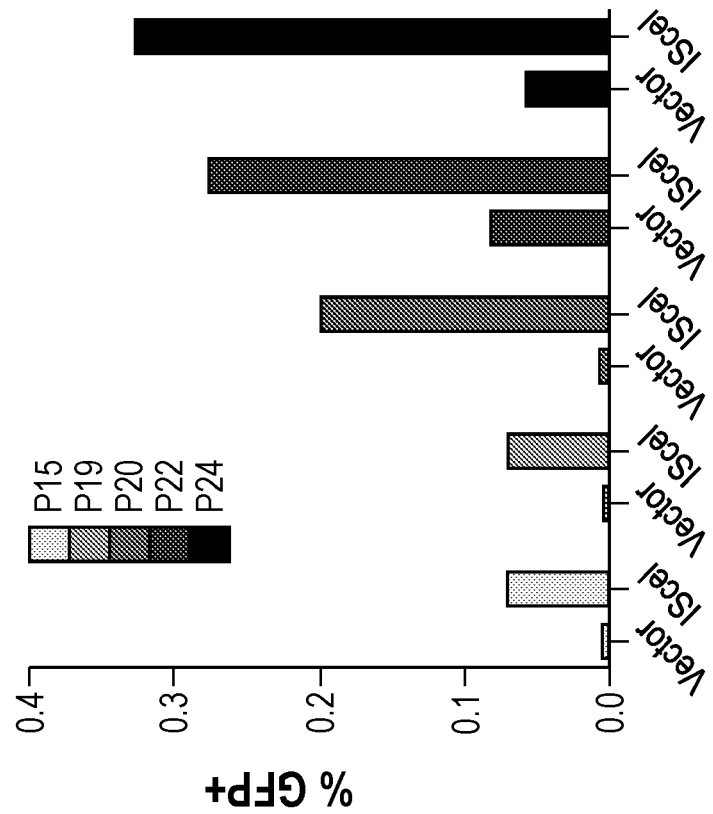
FIG. 5A
FIG. 5B

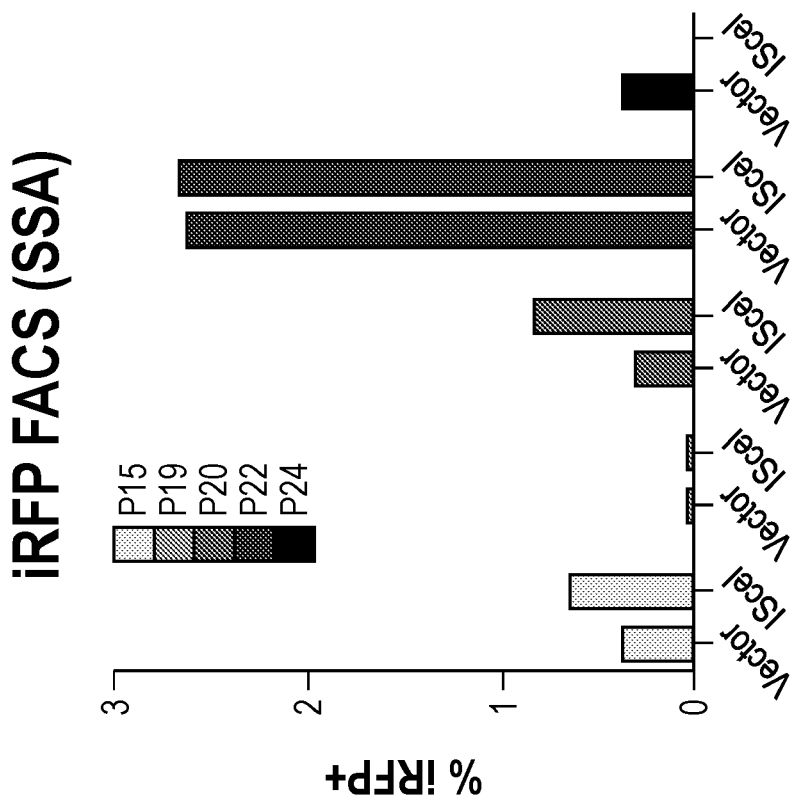
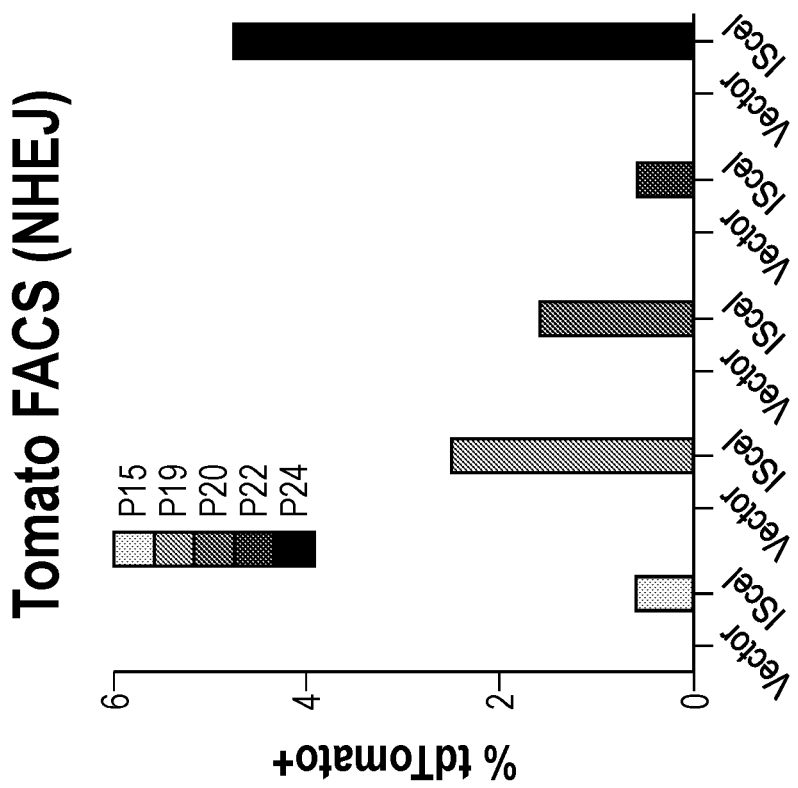
FIG. 5C
FIG. 5D

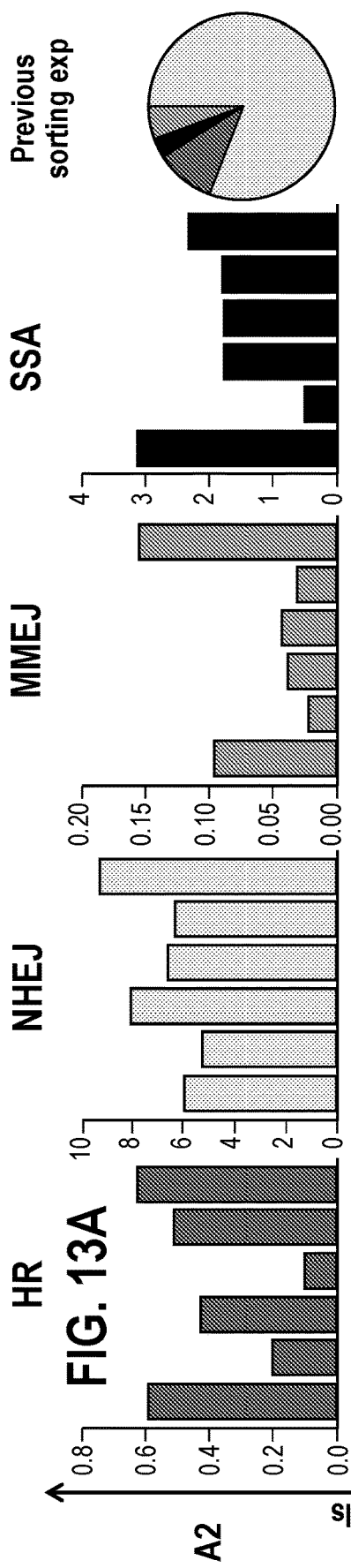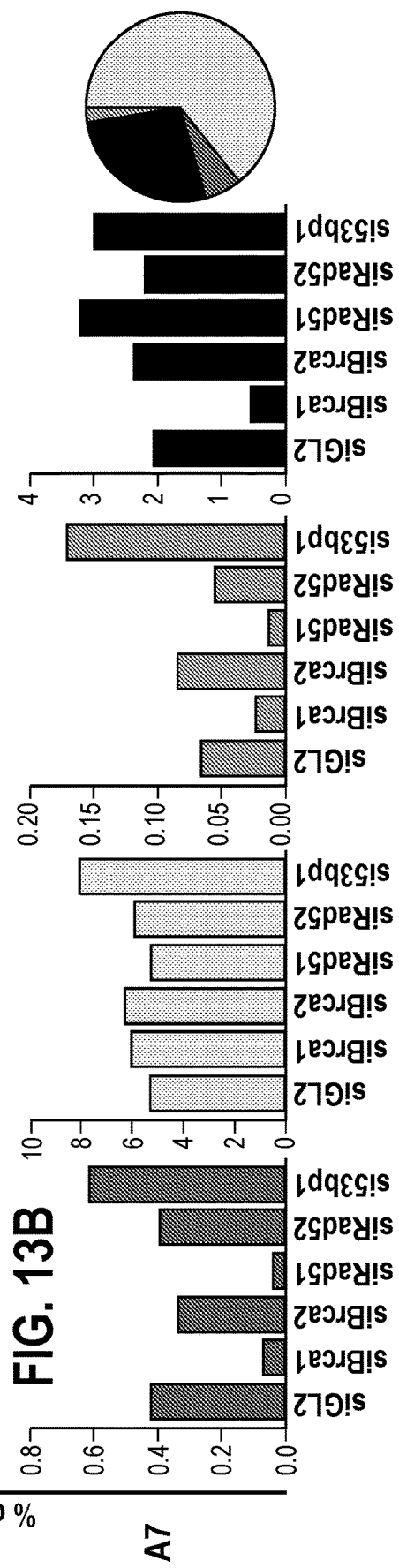
FIG. 13A
FIG. 13B

SEQUENCE LISTING

```
<160> NUMBER OF SEQ ID NOS: 14

<210> SEQ ID NO 1
<211> LENGTH: 28125
<212> TYPE: DNA
<213> ORGANISM: Artificial Sequence
<220> FEATURE:
<223> OTHER INFORMATION: Multifunctional DSB Reporter Construct
<220> FEATURE:
<221> NAME/KEY: misc_feature
<222> LOCATION: (298)..(11295)
<223> OTHER INFORMATION: First and Second cassettes
<220> FEATURE:
<221> NAME/KEY: promoter
<222> LOCATION: (298)..(2018)
<223> OTHER INFORMATION: CAG promoter
<220> FEATURE:
<221> NAME/KEY: misc_feature
<222> LOCATION: (2402)..(2596)
<223> OTHER INFORMATION: 5' EGFP coding region
<220> FEATURE:
<221> NAME/KEY: misc_feature
<222> LOCATION: (2600)..(2600)
<223> OTHER INFORMATION: AsiSI restriction site
<220> FEATURE:
<221> NAME/KEY: misc_feature
<222> LOCATION: (2620)..(2620)
<223> OTHER INFORMATION: I-SceI restriction site
<220> FEATURE:
<221> NAME/KEY: misc_feature
<222> LOCATION: (9240)..(9240)
<223> OTHER INFORMATION: I-SceI restriction site
<220> FEATURE:
<221> NAME/KEY: misc_feature
<222> LOCATION: (9258)..(9258)
<223> OTHER INFORMATION: AsiSI restriction site
<220> FEATURE:
<221> NAME/KEY: misc_feature
<222> LOCATION: (9273)..(9797)
<223> OTHER INFORMATION: 3' EGFP-Y64H coding region
```

```
<220> FEATURE:
<221> NAME/KEY: misc_feature
<222> LOCATION: (9845)..(10497)
<223> OTHER INFORMATION: Internal Ribosome Entry SEquence (IRES)
<220> FEATURE:
<221> NAME/KEY: misc_feature
<222> LOCATION: (10498)..(11925)
<223> OTHER INFORMATION: tdTomato coding region
<220> FEATURE:
<221> NAME/KEY: misc_feature
<222> LOCATION: (17572)..(19191)
<223> OTHER INFORMATION: Third and Fourth Cassettes
<220> FEATURE:
<221> NAME/KEY: misc_feature
<222> LOCATION: (17572)..(18069)
<223> OTHER INFORMATION: 5' EGFP coding region
<220> FEATURE:
<221> NAME/KEY: misc_feature
<222> LOCATION: (18262)..(19161)
<223> OTHER INFORMATION: iRFP670 coding region

<400> SEQUENCE: 1
```

| | | | |
|---|---|---|---|
| tccaggtcct gaccgttctg tccgtcactt cccagatccg cgctttctct gtccttcctg | 60 |
| tgcgacggtt acgccgctcc atgagcttat cgggtccact cgcgaacgca gaaaggccca | 120 |
| cccgaaggtg agccagtgtg attacatttg cggcctaact gtggccagtc cagttacgct | 180 |
| ggagtcacta gtatttaggt gacactatag aagcggccgc gacaacttgt ccacgtggaa | 240 |
| ttctaagctt atttaaattg gcaaacagct attatgggta ttatgggtga gctcgtcgac | 300 |
| attgattatt gactagttat taatagtaat caattacggg gtcattagtt catagcccat | 360 |
| atatggagtt ccgcgttaca taacttacgg taaatggccc gcctggctga ccgcccaacg | 420 |
| acccccgccc attgacgtca ataatgacgt atgttcccat agtaacgcca atagggactt | 480 |
| tccattgacg tcaatgggtg gagtatttac ggtaaactgc ccacttggca gtacatcaag | 540 |
| tgtatcatat gccaagtccg ccccctattg acgtcaatga cggtaaatgg cccgcctggc | 600 |
| attatgccca gtacatgacc ttacgggact ttcctacttg gcagtacatc tacgtattag | 660 |
| tcatcgctat taccatgggt cgaggtgagc cccacgttct gcttcactct ccccatctcc | 720 |
| cccccctccc cacccccaat tttgtattta tttatttttt aattattttg tgcagcgatg | 780 |
| ggggcggggg gggggggggc gcgcgccagg cgggcgggg cggggcgagg ggcggggcgg | 840 |
| ggcgaggcgg agaggtgcgg cggcagccaa tcagagcggc gcgctccgaa agtttccttt | 900 |
| tatggcgagg cggcggcggc ggcggcccta taaaaagcga agcgcgcggc gggcgggagt | 960 |
| cgctgcgttg ccttcgcccc gtgccccgct ccgcgccgcc tcgcgccgcc cgccccggct | 1020 |
| ctgactgacc gcgttactcc cacaggtgag cgggcgggac ggcccttctc ctccgggctg | 1080 |
| taattagcgc ttggtttaat gacggctcgt ttcttttctg tggctgcgtg aaagccttaa | 1140 |
| agggctccgg gagggccctt tgtgcggggg ggagcggctc gggggggtgcg tgcgtgtgtg | 1200 |
| tgtgcgtggg gagcgccgcg tgcggcccgc gctgcccggc ggctgtgagc gctgcgggcg | 1260 |
| cggcgcgggg ctttgtgcgc tccgcgtgtg cgcgagggga gcgcggccgg gggcggtgcc | 1320 |
| ccgcggtgcg ggggggctgc gaggggaaca aaggctgcgt gcggggtgtg tgcgtggggg | 1380 |
| ggtgagcagg gggtgtgggc gcggcggtcg ggctgtaacc ccccctgca cccccctccc | 1440 |
| cgagttgctg agcacggccc ggcttcgggt gcggggctcc gtgcggggcg tggcgcgggg | 1500 |
| ctcgccgtgc cgggcggggg gtggcggcag gtgggggtgc cgggcggggc ggggccgcct | 1560 |
| cgggccgggg agggctcggg ggaggggcgc ggcggcccg gagcgccggc ggctgtcgag | 1620 |
| gcgcggcgag ccgcagccat tgcctttat ggtaatcgtg cgagagggcg cagggacttc | 1680 |

```
ctttgtccca aatctggcgg agccgaaatc tgggaggcgc cgccgcaccc cctctagcgg    1740
gcgcgggcga agcggtgcgg cgccggcagg aaggaaatgg gcggggaggg ccttcgtgcg    1800
tcgccgcgcc gccgtcccct tctccatctc cagcctcggg gctgccgcag ggggacggct    1860
gccttcgggg gggacggggc agggcggggt tcggcttctg gcgtgtgacc ggcggctcta    1920
gagcctctgc taaccatgtt catgccttct tcttttcct acagctcctg ggcaacgtgc     1980
tggttattgt gctgtctcat cattttggca aagaattcgc ccgggcagat ccgccgccac    2040
tgccaccatg ggatcaagat cgccaaaaaa gaagagaaag gtgccgaaga agcatgcagc    2100
accaccaaaa aaaaaacgaa aagtagaaga cccacgaggc aacaccagcg gcgtgctgag    2160
cacccccaag gccaagaggg ccaagcaccc cccggcacc gagaagccca ggagcaggag    2220
ccagagcgag cagcccgcca cctgccccat ctgctacgcc gtgatcaggc agagcaggaa    2280
cctgaggagg cacctggagc tgaggcactt cgccaagccc ggcgtggatc caccggtcgg    2340
cagcggcgag ggccgcggca gcctgctgac ctgcggcgac gtggaggaga ccccggccc     2400 catggtgagc aagggcgagg agctgttcac cggggtggtg cccatcctgg tcgagctgga    2460
cggcgacgta aacggccaca agttcagcgt gtccggcgag ggcgagggcg atgccaccta    2520
cggcaagctg accctgaagt tcatctgcac caccggcaag ctgcccgtgc cctggcccac    2580
cctcgtgacc accctgcgat cgcccctatt accctgttat ccctaggata aacctcgagc    2640
cgttacttag aaccacaaag tgggaatcaa gagaaaaaca atgatcccac gagagatcta    2700
tagatctata gatcatgagt gggaggaatg agctggccct taatttggtt ttgcttgttt    2760
aaattatgat atccaactat gaaacattat cataaagcaa tagtaaagag ccttcagtaa    2820
agagcaggca tttatctaat cccaccccac ccccaccccc gtagctccaa tccttccatt    2880
caaaatgtag gtactctgtt ctcacccttc ttaacaaagt atgacaggaa aaacttccat    2940
tttagtggac atctttattg tttaatagat catcaatttc tgcatcccgg ggatctgata    3000
tcatcgatgc atggggtcgt cgcgctcctt cggtcgggcg ctgcgggtcg tggggcgggc    3060
gctattcctt tgccctcgga cgagtgctgg ggcgtcggtt tccactatcg gcgagtactt    3120
ctacacagcc atcggtccag acggccgcgc ttctgcgggc gatttgtgta cgcccgacag    3180
tcccggctcc ggatcggacg attgcgtcgc atcgaccctg cgcccaagct gcatcatcga    3240
aattgccgtc aaccaagctc tgatagagtt ggtcaagacc aatgcggagc atatacgccc    3300
ggagccgcgg cgatcctgca agctccggat gcctccgctc gaagtagcgc gtctgctgct    3360
ccatacaagc caaccacggc ctccagaaga agatgttggc gacctcgtat tgggaatccc    3420
cgaacatcgc ctcgctccag tcaatgaccg ctgttatgcg gccattgtcc gtcaggacat    3480
tgttggagcc gaaatccgcg tgcacgaggt gccggacttc ggggcagtcc tcggcccaaa    3540
gcatcagctc atcgagagcc tgcgcgacgg acgcactgac ggtgtcgtcc atcacagttt    3600
gccagtgata cacatgggga tcagcaatcg cgcatatgaa atcacgccat gtagtgtatt    3660
gaccgattcc ttgcggtccg aatgggccga acccgctcgt ctggctaaga tcggccgcag    3720
cgatcgcatc catggcctcc gcgaccggct gcagaacagc gggcagttcg gtttcaggca    3780
ggtcttgcaa cgtgacaccc tgtgcacggc gggagatgca ataggtcagg ctctcgctga    3840
attccccaat gtcaagcact tccggaatcg ggagcgcggc cgatgcaaag tgccgataaa    3900
cataacgatc tttgtagaaa ccatcggcgc agctatttac ccgcaggaca tatccacgcc    3960
ctcctacatc gaagctgaaa gcacgagatt cttcgccctc cgagagctgc atcaggtcgg    4020
agacgctgtc gaacttttcg atcagaaact ctctgacaga cgtcgcggtg agttcaggct    4080
```

```
ttttccccat ggtaagcttc agctgctcga tcgagatcta gatggatgca ggtcgaaagg    4140
cccggagatg aggaagagga gaacagcgcg gcagacgtgc gcttttgaag cgtgcagaat    4200
gccgggcctc cggaggacct tcgggcgccc gccccgcccc tgagcccgcc cctgagcccg    4260
cccccggacc cacccctcc cagcctctga gcccagaaag cgaaggagca aagctgctat     4320
tggccgctgc cccaaaggcc tacccgcttc cattgctcag cggtgctgtc catctgcacg    4380
agactagtga gacgtgctac ttccatttgt cacgtcctgc acgacgcgag ctgcggggcg    4440
ggggggaact tcctgactag ggaggagta gaaggtggcg cgaaggggcc accaaagaac     4500
ggagccggtt ggcgcctacc ggtggatgtg gaatgtgtgc gaggccagag gccacttgtg    4560
tagcgccaag tgcccagcgg ggctgctaaa gcgcatgctc cagactgcct tgggaaaagc    4620
gcctcccta cccggtagaa tttcgaggtc gaagggcgca gtagtccagg gtttccttga     4680
tgatgtcata cttatcctgt ccctttttt tccacaggga tcctcgggga caccaaatat     4740
ggcgatctcg gccttttcgt ttcttggagc tgggacatgt ttgccatcga tccatctacc    4800
accagaacgg ccgttagatc tgctgccacc gttgtttcca ccgaagaaac caccgttgcc    4860
gtaaccacca cgacggttgt tgctaaagaa gctgccaccg ccacggccac cgttgtagcc    4920
gccgttgttg ttattgtagt tgctcatgtt atttctggca cttcttggtt ttcctcttaa    4980
gtgaggagga acataaccat tctcgttgtt gtcgttgatg cttaaatttt gcacttgttc    5040
gctcagttca gccataatat gaaatgcttt tcttgttgtt cttacggaat accacttgcc    5100
acctatcacc acaactaact ttttcccgtt cctccatctc ttttatattt tttttctcga    5160
tcgagggatc tttgtgaagg aaccttactt ctgtggtgtg acataattgg acaaactacc    5220
tacagagatt taaagctcta aggtaaatat aaaatttta agtgtataat gtgttaaact     5280
actgattcta attgtttgtg tattttagat tccaacctat ggaactgatg aatgggagca    5340
gtggtggaat gcctttaatg aggaaaacct gttttgctca gaagaaatgc catcagtga    5400
tgatgaggct actgctgact ctcaacattc tactcctcca aaaagaaga gaaaggtaga    5460
agacccaag gactttcctt cagaattgct aagttttttg agtcatgctg tgtttagtaa    5520
tagaactctt gcttgctttg ctatttacac cacaaaggaa aaagctgcac tgctatacaa    5580
gaaaattatg gaaaaatatt ctgtaacctt tataagtagg cataacagtt ataatcataa    5640
catactgttt tttcttactc cacacaggca tagagtgtct gctattaata actatgctca    5700
aaaattgtgt acctttagct ttttaatttg taaaggggtt aataaggaat atttgatgta    5760
tagtgccttg actagagatc ataatcagcc ataccacatt tgtagaggtt ttacttgctt    5820
taaaaaacct cccacacctc cccctgaacc tgaaacataa aatgaatgca attgttgttg    5880
ttaacttgtt tattgcagct tataatggtt acaaataaag caatagcatc acaaatttca    5940
caaataaagc atttttttca ctgcattcta gttgtggttt gtccaaactc atcaatgtat    6000
cttatcatgt ctggtcgagg gatctttgtg aaggaacctt acttctgtgg tgtgacataa    6060
ttggacaaac tacctacaga gatttaaagc tctaaggtaa atataaaatt tttaagtgta    6120
taatgtgtta aactactgat tctaattgtt tgtgtatttt agattccaac ctatggaact    6180
gatgaatggg agcagtggtg gaatgccttt aatgaggaaa acctgttttg ctcagaagaa    6240
atgccatcta gtgatgatga ggctactgct gactctcaac attctactcc tccaaaaaag    6300
aagagaaagg tagaagaccc caaggacttt ccttcagaat tgctaagttt tttgagtcat    6360
gctgtgttta gtaatagaac tcttgcttgc tttgctattt acaccacaaa ggaaaaagct    6420
```

-continued

```
gcactgctat acaagaaaat tatggaaaaa tattctgtaa cctttataag taggcataac    6480
agttataatc ataacatact gttttttctt actccacaca ggcatagagt gtctgctatt    6540
aataactatg ctcaaaaatt gtgtaccttt agcttttaa tttgtaaagg ggttaataag    6600
gaatatttga tgtatagtgc cttgactaga gatcataatc agccatacca catttgtaga    6660
ggttttactt gctttaaaaa acctcccaca cctcccctg aacctgaaac ataaaatgaa    6720
tgcaattgtt gttgttaact tgtttattgc agcttataat ggttacaaat aaagcaatag    6780
catcacaaat ttcacaaata aagcattttt ttcactgcat tctagttgtg gtttgtccaa    6840
actcatcaat gtatcttatc atgtctggtc gagggatctt tgtgaaggaa ccttacttct    6900
gtggtgtgac ataattggac aaactaccta cagagattta aagctctaag gtaaatataa    6960
aatttttaag tgtataatgt gttaaactac tgattctaat tgtttgtgta ttttagattc    7020
caacctatgg aactgatgaa tgggagcagt ggtggaatgc ctttaatgag gaaaacctgt    7080
tttgctcaga agaaatgcca tctagtgatg atgaggctac tgctgactct caacattcta    7140
ctcctccaaa aagaagaga aaggtagaag accccaagga ctttccttca gaattgctaa    7200
gttttttgag tcatgctgtg tttagtaata gaactcttgc ttgctttgct atttacacca    7260
caaaggaaaa agctgcactg ctatacaaga aaattatgga aaaatattct gtaacccttta    7320
taagtaggca taacagttat aatcataaca tactgttttt tcttactcca cacaggcata    7380
gagtgtctgc tattaataac tatgctcaaa aattgtgtac ctttagcttt ttaatttgta    7440
aaggggttaa taaggaatat ttgatgtata gtgccttgac tagagatcat aatcagccat    7500
accacatttg tagaggtttt acttgcttta aaaaacctcc cacacctccc cctgaacctg    7560
aaacataaaa tgaatgcaat tgttgttgtt aacttgttta ttgcagctta taatggttac    7620
aaataaagca atagcatcac aaatttcaca aataaagcat tttttcact gcattctagt    7680
tgtggttgt ccaaactcat caatgtatct tatcatgtct ggtcgaggga tctttgtgaa    7740
ggaaccttac ttctgtggtg tgacataatt ggacaaacta cctacagaga tttaaagctc    7800
taaggtaaat ataaaatttt taagtgtata atgtgttaaa ctactgattc taattgtttg    7860
tgtatttag attccaacct atggaactga tgaatgggag cagtggtgga atgcctttaa    7920
tgaggaaaac ctgttttgct cagaagaaat gccatctagt gatgatgagg ctactgctga    7980
ctctcaacat tctactcctc caaaaagaa gagaaaggta gaagacccca aggactttcc    8040
ttcagaattg ctaagttttt tgagtcatgc tgtgtttagt aatagaactc ttgcttgctt    8100
tgctatttac accacaaagg aaaaagctgc actgctatac aagaaaatta tggaaaaata    8160
ttctgtaacc tttataagta ggcataacag ttataatcat aacatactgt ttttcttac    8220
tccacacagg catagagtgt ctgctattaa taactatgct caaaaattgt gtacctttag    8280
ctttttaatt tgtaaagggg ttaataagga atatttgatg tatagtgcct tgactagaga    8340
tcataatcag ccataccaca tttgtagagg ttttacttgc tttaaaaaac ctcccacacc    8400
tcccctgaa cctgaaacat aaaatgaatg caattgttgt tgttaacttg tttattgcag    8460
cttataatgg ttacaaataa agcaatagca tcacaaattt cacaaataaa gcatttttt    8520
cactgcattc tagttgtggt ttgtccaaac tcatcaatgt atcttatcat gtctggaatt    8580
ccgcaatcta gacaccatgg cttgagtaag tctgcagctc gagaaacaat aaaagtgcac    8640
accttaaaaa tgaggccaag tgtgactttg tggtgtggct gggttggggg cagcagaggg    8700
tgaaccctgc aggagggtga accctgcaaa agggtgggga agtgggggcc aacttgtcct    8760
tacccagagt gcaggtgtgt ggagatccct cctgccttga cattgagcag ccttagaggg    8820
```

```
tgggggaggc tcagggtca ggtctctgtt cctgcttatt ggggagttcc tggcctggcc      8880
cttctatgtc tccccaggta ccccagtttt tctgggttca cccagagtgc agatgcttga      8940
ggaggtggga agggactatt tgggggtgtc tggctcaggt gccatgcctc actggggctg      9000
gttggcacct gcatttcctg ggagtggggc tgtctcaggg tagctgggca cggtgttccc      9060
ttgagtgggg gtgtagtggg tgttcctagc tgccacgcct ttgccttcac ctagctagca      9120
tctagattaa ttaagttcac tgccgtatag gcagctaaga aaataaaagt tcactgccgt      9180
ataggcagct aagaaaaata aagttcactg ccgtataggc agctaagaaa ctagggataa      9240
cagggtaata gggcgatcg ctgaccaccc tgtcacacgt gtgcagtgc ttcagccgct      9300 accccgacca catgaagcag cacgacttct tcaagtccgc catgcccgaa ggctacgtcc      9360
aggagcgcac catcttcttc aaggacgacg gcaactacaa gacccgcgcc gaggtgaagt      9420
tcgagggcga caccctggtg aaccgcatcg agctgaaggg catcgacttc aaggaggacg      9480
gcaacatcct gggcacaag ctggagtaca actacaacag ccacaacgtc tatatcatgg      9540
ccgacaagca gaagaacggc atcaaggtga acttcaagat ccgccacaac atcgaggacg      9600
gcagcgtgca gctcgccgac cactaccagc agaacacccc catcggcgac ggccccgtgc      9660
tgctgcccga caaccactac ctgagcaccc agtccgccct gagcaaagac cccaacgaga      9720
agcgcgatca catggtcctg ctggagttcg tgaccgccgc cgggatcact ctcggcatgg      9780
acgagctgta caagtaataa ggccggcgcg ccgcggccgc tacgtaaatt ccgcccctct      9840 ccctccccc ccctaacgt tactggccga agccgcttgg aataaggccg gtgtgcgttt      9900
gtctatatgt tattttccac catattgccg tcttttggca atgtgagggc ccggaaacct      9960
ggccctgtct tcttgacgag cattcctagg ggtctttccc ctctcgccaa aggaatgcaa     10020
ggtctgttga atgtcgtgaa ggaagcagtt cctctggaag cttcttgaag acaaacaacg     10080
tctgtagcga ccctttgcag gcagcggaac cccccacctg gcgacaggtg cctctgcggc     10140
caaaagccac gtgtataaga tacacctgca aaggcggcac aaccccagtg ccacgttgtg     10200
agttggatag ttgtggaaag agtcaaatgg ctctcctcaa gcgtattcaa caaggggctg     10260
aaggatgccc agaaggtacc ccattgtatg ggatctgatc tggggcctcg gtgcacatgc     10320
tttacatgtg tttagtcgag gttaaaaaac gtctaggccc cccgaaccac ggggacgtgg     10380
ttttcctttg aaaacacga tgataatacc atggatccaa aaagaagag aaggtagat     10440 ccaaaaaga agagaaaggt agatccaaaa agaagagaa aggtaggagc cacaaccatg     10500
ttgagcaagg gcgaggaggt catcaaagag ttcatgcgct tcaaggtgcg catggagggc     10560
tccatgaacg gccacgagtt cgagatcgag ggcgagggcg agggccgccc ctacgagggc     10620
acccagaccg ccaagctgaa ggtgaccaag ggcggccccc tgcccttcgc ctgggacatc     10680 ctgtccccc agttcatgta cggctccaag gcgtacgtga agcaccccgc cgacatcccc     10740
gattacaaga agctgtcctt ccccgagggc ttcaagtggg agcgcgtgat gaacttcgag     10800
gacggcggtc tggtgaccgt gacccaggac tcctccctgc aggacggcac gctgatctac     10860
aaggtgaaga tgcgcggcac caacttcccc cccgacggcc ccgtaatgca gaagaagacc     10920
atgggctggg aggcctccac cgagcgcctg taccccgcg acggcgtgct gaagggcgag     10980
atccaccagg ccctgaagct gaaggacggc ggccactacc tggtggagtt caagaccatc     11040
tacatggcca gaagcccgt gcaactgccc ggctactact acgtggacac caagctggac     11100
atcacctccc acaacgagga ctacaccatc gtggaacagt acgagcgctc cgagggccgc     11160
```

```
caccacctgt tcctggggca tggcaccggc agcaccggca gcggcagctc cggcaccgcc   11220
tcctccgagg acaacaacat ggccgtcatc aaagagttca tgcgcttcaa ggtgcgcatg   11280
gagggctcca tgaacggcca cgagttcgag atcgagggcg agggcgaggg ccgcccctac   11340
gagggcaccc agaccgccaa gctgaaggtg accaagggcg gccccctgcc cttcgcctgg   11400
gacatcctgt cccccagtt catgtacggc tccaaggcgt acgtgaagca ccccgccgac   11460
atccccgatt acaagaagct gtccttcccc gagggcttca gtgggagcg cgtgatgaac   11520
ttcgaggacg gcggtctggt gaccgtgacc caggactcct ccctgcagga cggcacgctg   11580
atctacaagg tgaagatgcg cggcaccaac ttccccccg acggcccgt aatgcagaag   11640
aagaccatgg gctgggaggc ctccaccgag cgcctgtacc ccgcgacgg cgtgctgaag   11700
ggcgagatcc accaggccct gaagctgaag gacggcggcc actacctggt ggagttcaag   11760
accatctaca tggccaagaa gcccgtgcaa ctgcccggct actactacgt ggacaccaag   11820
ctggacatca cctcccacaa cgaggactac accatcgtgg aacagtacga gcgctccgag   11880
ggccgccacc acctgttcct gtacggcatg gacgagctgt acaagggatc tggagctact   11940
aatttctctc ttcttaaaca agctggagat gttgaagaaa atccaggacc aaccgagtac   12000
aagcccaccg tgcgcctggc caccgcgac gacgtgcccc gcgccgtgcg caccctggcc   12060
gccgccttcg ccgactaccc cgccaccgc cacaccgtgg accccgaccg ccacatcgag   12120
cgcgtgaccg agctgcagga gctgttcctg acccgcgtgg gcctggacat cggcaaggtg   12180
tgggtggccg acgacggcgc cgccgtggcc gtgtggacca ccccgagag cgtggaggcc   12240
ggcgccgtgt cgccgagat cggccccgc atggccgagc tgagcggcag ccgcctggcc   12300
gcccagcagc agatggaggg cctgctggcc ccccaccgcc caaggagcc cgcctggttc   12360
ctggccaccg tgggcgtgag ccccgaccac cagggcaagg gctgggcag cgccgtggtg   12420
ctgcccggcg tggaggccgc cgagcgcgcc ggcgtgcccg ccttcctgga ccagcgcc    12480
ccccgcaacc tgcccttcta cgagcgcctg ggcttcaccg tgaccgccga cgtggaggtg   12540
cccgagggcc cccgcacctg gtgcatgacc cgcaagcccg cgcctaata ataagatatc   12600
ggccggccct gcaggaattc gatatcaagc ttatcgataa tcaacctctg gattacaaaa   12660
tttgtgaaag attgactggt attcttaact atgttgctcc ttttacgcta tgtggatacg   12720
ctgctttaat gcctttgtat catgctattg cttcccgtat ggctttcatt ttctcctcct   12780
tgtataaatc ctggttgctg tctctttatg aggagttgtg gcccgttgtc aggcaacgtg   12840
gcgtggtgtg cactgtgttt gctgacgcaa ccccactgg ttggggcatt gccaccacct   12900
gtcagctcct ttccgggact ttcgctttcc ccctccctat gccacggcg gaactcatcg   12960
ccgcctgcct tgcccgctgc tggacagggg ctcggctgtt gggcactgac aattccgtgg   13020
tgttgtcggg gaaatcatcg tcctttcctt ggctgctcgc ctgtgttgcc acctggattc   13080
tgcgcgggac gtccttctgc tacgtccctt cggccctcaa tccagcggac cttcttccc    13140
gcggcctgct gccggctctg cggcctcttc cgcgtcttcg ccttcgccct cagacgagtc   13200
ggatctccct ttgggccgcc tccccgcatc gataccgtcg acctcgactg tgccttctag   13260
ttgccagcca tctgttgttt gccctagcg ccgcgactc tagatcataa tcagccatac   13320
cacatttgta gaggttttac ttgctttaaa aaacctccca cacctccccc tgaacctgaa   13380
acataaaatg aatgcaattg ttgttgttaa cttgtttatt gcagcttata atggttacaa   13440
ataaagcaat agcatcacaa atttcacaaa taaagcattt ttttcactgc attctagttg   13500
tggtttgtcc aaactcatca atgtatctta aggcgtaaat tgtaagcgtt aatctgaagc   13560
```

```
ttctgatgga attagaactt ggcaaaacaa tactgagaat gaagtgtatg tggaacagag    13620
gctgctgatc tcgttcttca ggctatgaaa ctgacacatt tggaaaccac agtacttaga    13680
accacaaagt gggaatcaag agaaaaacaa tgatcccacg agagatctat agatctatag    13740
atcatgagtg ggaggaatga gctggccctt aatttggttt tgcttgttta aattatgata    13800
tccaactatg aaacattatc ataaagcaat agtaaagagc cttcagtaaa gagcaggcat    13860
ttatctaatc ccaccccacc cccaccccg tagctccaat ccttccattc aaaatgtagg     13920
tactctgttc tcaccttct taacaaagta tgacaggaaa aacttccatt ttagtggaca      13980
tctttattgt ttaatagatc atcaatttcg atccgctcct gggcaccgaa ctgcgccgcg    14040
tgttcagcag ggtcggcgtg ttcggtgtgt ccccgcggt gggcctcggg ggcgggtgcg     14100
gggtcggcgg ggccgccccg ggtggcttcg gtcggagcca tggggtcgtg cgctcctttc    14160
ggtcgggcgc tgcgggtcgt ggggcgggcg ttagaaccag ggcacgaagc cgcccttgct    14220
caggccgtag caggtgaagc cgccctcctc ggcggtcacc tgcaggggc cgtggcggat     14280 gaacaggcgg aagtgctggc cggtgctctg gctgcgcagg gtcacgaagg gcaggtccag    14340
ggcgcgggcc acggtgtcgg ggatgcgctt gcgggcctcc tcctcgctca ggtcgtggcg    14400
gcgcatcagg cggcggcgca ggcgctcggg gttgctcttg gcctgcacgc ggctcacctg    14460
gcggtagggg gtggggtggg gcaccacggc gggctcgccg aactgcaggt ggtcgcgcag    14520
gccctccagc caggggcggg ccagcagggc gcgcaggtcg tcggcgctgg cgtggatgcg    14580
caggcgctcg cccaggcggc tgcggctctc gtccaggtcg gggaagctca cgccgatgcg    14640
gtcgccgccc tgggccacca gggcctggtg cagcttgccg aacagcacgc tcatcagctg    14700 ggcgggggg aactcggggt cggggcgcag gcggatgtcc aggtagtggt cgctggcggc     14760
gttgctctgg aagtacaggt tctcgtggtg gtggtggtgg tggctgctct tggggccggg    14820
gttctcctcc acgtcgccgg cctgcttcag caggctgaag ttggtggcgc cgctgccggg    14880
cgcgccctgc agctgcaggc cctcccacac ataaccagag ggcagcaatt cacgaatccc    14940
aactgccgtc ggctgtccat cactgtcctt cactatggct ttgatcccag gatgcagatc    15000
gagaagcacc tgtcggcacc gtccgcaggg gctcaagatg cccctgttct catttccgat    15060
cgcgacgata caagtcaggt tgccagctgc cgcagcagca gcagtgccca gcaccacgag    15120
ttctgcacaa ggtcccccag taaaatgata tacattgaca ccagtgaaga tgcggccgtc    15180
gctagagaga gctgcgctgg cgacgctgta gtcttcagag atggggatgc tgttgattgt    15240
agccgttgct ctttcaatga gggtggattc ttcttgagac aaaggcttgg ccatggtggc    15300
ggctggatcg gtcgaaaggc ccggagatga ggaagaggag aacagcgcgg cagacgtgcg    15360
cttttgaagc gtgcagaatg ccgggcctcc ggaggacctt cgggcgcccg cccgcccct    15420 gagcccgccc ctgagcccgc ccccggaccc accccttccc agcctctgag cccagaaagc    15480
gaaggagcaa agctgctatt ggccgctgcc ccaaaggcct acccgcttcc attgctcagc    15540
ggtgctgtcc atctgcacga gactagtgag acgtgctact tccatttgtc acgtcctgca    15600
cgacgcgagc tgcggggcgg gggggaactt cctgactagg ggaggagtag aaggtggcgc    15660
gaaggggcca ccaaagaacg gagccggttg gcgcctaccg tggatgtgg aatgtgtgag     15720 gccagaggcc acttgtgtag cgccaagtgc ccagcggggc tgctaaagcg catgctccag    15780
actgccttgg gaaaagcgcc tcccctaccc ggtagaattc actcctcagg tgcaggctgc    15840
ctatcagaag gtggtggctg gtgtggccaa tgccctggct cacaaatacc actgagatct    15900
```

```
tttcccctct gccaaaaatt atggggacat catgaagccc cttgagcatc tgacttctgg   15960
ctaataaagg aaatttattt tcattgcaat agtgtgttgg aatttttgt gtctctcact    16020 cggaaggaca tatgggaggg caaatcattt aaaacatcag aatgagtatt tggtttagag   16080
tttggcaaca tatgccatat gctggctgcc atgaacaaag gtggctataa agaggtcatc   16140
agtatatgaa acagccccct gctgtccatt ccttattcca tagaaaagcc ttgacttgag   16200
gttagatttt ttttatattt tgttttgtgt tatttttttc tttaacatcc ctaaaatttt   16260
ccttacatgt tttactagcc agattttttcc tcctctcctg actactccca gtcatagctg   16320
tccctcttct cttatgaaga tccctcgact cgcgatgaat aaatgaaagc ttgcagatct   16380
gcgactctag aggatctgcg actctagagg atcataatca gccataccac attttttgtag  16440 aggttttact tgctttaaaa aacctcccac acctccccct gaacctgaaa cataaaatga   16500
atgcaattgt tgttgttaac ttgttttattg cagcttataa tggttacaaa taaagcaata   16560
gcatcacaaa tttcacaaat aaagcatttt tttcactgca ttctagttgt ggtttgtcca   16620
aactcatcaa tgtatcttat catgtctgga tctgcgactc tagaggatca taatcagcca   16680
taccacattt gtagaggttt tacttgcttt aaaaaacctc ccacacctcc ccctgaacct   16740
gaaacataaa atgaatgcaa ttgttgttgt taacttgttt attgcagctt ataatggtta   16800
caaataaagc aatagcatca caaatttcac aaataaagca ttttttttcac tgcattctag  16860 ttgtggtttg tccaaactca tcaatgtatc ttatcatgtc tggatctgcg actctagagg   16920
atcataatca gccataccac atttgtagag gttttacttg ctttaaaaaa cctcccacac   16980 ctcccccctga acctgaaaca taaatgaat gcaattgttg ttgttaactt gtttattgca    17040
gcttataatg gttacaaata aagcaatagc atcacaaatt tcacaaataa agcatttttt   17100
tcactgcatt ctagttgtgg tttgtccaaa ctcatcaatg tatcttatca tgtctggatc   17160
catcaagctg atccggaacc cttaagccac catgggtaat agggtatacc ccaagctttt   17220
agggatcaag atcccaaaaa gaagagaaag gtgccgaaga agcatgcagc accaccaaaa   17280
aaaaaacgaa aagtagaaga cccacgaggc aacaccagcg gcgtgctgag cacccccaag   17340
gccaagaggg ccaagcaccc ccccggcacc gagaagccca ggagcaggag ccagagcgag   17400
cagcccgcca cctgccccat ctgctacgcc gtgatcaggc agagcaggaa cctgaggagg   17460
cacctggagc tgaggcactt cgccaagccc ggcgtggatc caccggtcgg cagcggcgag   17520
ggccgcggca gcctgctgac ctgcggcgac gtggaggaga cccccggccc cgtgagcaag   17580
ggcgaggagc tgttcaccgg ggtggtgccc atcctggtcg agctggacgg cgacgtaaac   17640
ggccacaagt tcagcgtgtc cggcgagggc gagggcgatg ccacctacgg caagctgacc   17700
ctgaagttca tctgcaccac cggcaagctg cccgtgccct ggcccaccct cgtgaccacc   17760
ctgacatatg gcgtgcagtg cttcagccgc taccccgacc acatgaagca gcacgacttc   17820
ttcaagtccg ccatgcccga aggctacgtc caggagcgca ccatcttctt caaggacgac   17880
ggcaactaca agacccgcgc cgaggtgaag ttcgagggcg acaccctggt gaaccgcatc   17940
gagctgaagg gcatcgactt caaggaggac ggcaacatcc tggggcacaa gctggagtac   18000
aactacaaca gccacaacgt ctatatcatg gccgacaagc agaagaacgg catcaaggtg   18060
aacttcaagg gttcactgcc gtataggcag ctaagaaagg ggcgttcact gccgtatagg   18120
cagctaagaa cccctgttc actgccgtat aggcagctaa gaaatggcag cggcgccacc   18180
aacttcagcc tgctgaagca ggccggcgac gtggaggaga cccccggccc cggatccgat   18240
ccaaaaaaga agagaaaggt agcccgcaag gtggacctga ccagctgcga ccgcgagccc   18300
```

```
atccacatcc ccggcagcat ccagccctgc ggctgcctgc tggcctgcga cgcccaggcc   18360
gtgcgcatca cccgcatcac cgagaacgcc ggcgccttct tcggccgcga gaccccccgc   18420
gtgggcgagc tgctggccga ctacttcggc gagaccgagg cccacgccct gcgcaacgcc   18480
ctggcccaga gcagcgaccc caagcgcccc gccctgatct tcggctggcg cgacggcctg   18540
accggccgca ccttcgacat cagcctgcac cgccacgacg gcaccagcat catcgagttc   18600
gagcccgccg ccgccgagca ggccgacaac ccctgcgcc tgacccgcca gatcatcgcc    18660
cgcaccaagg agctgaagag cctggaggag atggccgccc gcgtgccccg ctacctgcag   18720
gccatgctgg gctaccaccg cgtgatgctg taccgcttcg ccgacgacgg cagcggcatg   18780
gtgatcggcg aggccaagcg cagcgacctg gagagcttcc tgggccagca cttccccgcc   18840
agcctggtgc cccagcaggc ccgcctgctg tacctgaaga cgccatccg cgtggtgagc    18900 gacagccgcg gcatcagcag ccgcatcgtg cccgagcacg acgccagcgg cgccgccctg   18960
gacctgagct tcgcccacct cgcgcagcatc agccctgcc acctggagtt cctgcgcaac    19020
atgggcgtga gcgccagcat gagcctgagc atcatcatcg acggcaccct gtggggcctg   19080
atcatctgcc accactacga gccccgcgcc gtgcccatgg cccagcgcgt ggccgccgag   19140
atgttcgccg acttcctgag cctgcacttc accgccgccc accaccagcg cgggtccggg   19200
caatgtacta attatgccct gctgaaactg gctggggatg tggagagtaa tccgggacct   19260
gccaagttga ccagtgccgt tccggtgctc accgcgcgcg acgtcgccgg agcggtcgag   19320
ttctggaccg accggctcgg gttctcccgg gacttcgtgg aggacgactt cgccggtgtg   19380
gtccgggacg acgtgaccct gttcatcagc gcggtccagg accaggtggt gccggacaac   19440
accctggcct gggtgtgggt gcgcggcctg gacgagctgt acgccgagtg gtcggaggtc   19500
gtgtccacga acttccggga cgcctccggg ccggccatga ccgagatcgg cgagcagccg   19560
tgggggcggg agttcgccct gcgcgacccg gccggcaact gcgtgcactt cgtggccgag   19620
gagcaggacg ggtccgggca atgtactaat tatgccctgc tgaaactggc tggggatgtg   19680
gagagtaatc cgggacctac cgagtacaag cccacggtgc gcctcgccac ccgcgacgac   19740
gtccccaggg ccgtacgcac cctcgccgcc gcgttcgccg actacccgc cacgcgccac   19800 accgtcgacc cggaccgcca catcgagcgg gtcaccgagc tgcaagaact cttcctcacg   19860
cgcgtcgggc tcgacatcgg caaggtgtgg gtcgcggacg acggcgccgc ggtggcggtc   19920
tggaccacgc cggagagcgt cgaagcgggg gcggtgttcg ccgagatcgg cccgcgcatg   19980
gccgagttga gcggttcccg gctggccgcg cagcaacaga tggaaggcct cctggcgccg   20040
caccggccca aggagcccgc gtggttcctg gccaccgtcg gcgtctcgcc cgaccaccag   20100
ggcaagggtc tgggcagcgc cgtcgtgctc cccgagtgg aggcggccga gcgcgccggg    20160
gtgcccgcct tcctggagac ctccgcgccc cgcaacctcc ccttctacga gcggctcggc   20220
ttcaccgtca ccgccgacgt cgaggtgccc gaaggaccgc gcacctggtg catgacccgc   20280
aagcccggtg cctaatttcc ctctgccaaa aattatgggg acatcatgaa gccccttgag   20340
catctgactt ctggctaata aaggaaattt attttcattg caatagtgtg ttggaatttt   20400
ttgtgtctct cactcggaag gacatatggg agggcaaatc atttaaaaca tcagaatgag   20460
tatttggttt agagtttggc aacatatgcc atatgctggc tgccatgaac aaaggtggct   20520
ataaagaggt catcagtata tgaaacagcc cctgctgtc cattccttat tccatagaaa     20580
agccttgact tgaggttaga tttttttat attttgtttt gtgttatttt tttctttaac   20640
```

```
atccctaaaa ttttccttac atgttttact agccagattt ttcctcctct cctgactact   20700
cccagtcata gctgtccctc acgcgtcgta actataacgg tcctaaggta gcgaaattta   20760
aataagcttg gaattcacgt gacttgaagt cgcggccgca ctgaccctat agtgagtcgt   20820
attaatttaa atcataccaa catggtcaaa taaaacgaaa ggctcagtcg aaagactggg   20880
cctttcgttt taatctgatc ggcacgtaag aggttccaac tttcaccata atgaaataag   20940
atcactaccg ggcgtatttt ttgagttatc gagattttca ggagctaagg aagctaaaat   21000
ggagaaaaaa atcactggat ataccaccgt tgatatatcc caatggcatc gtaaagaaca   21060
ttttgaggca tttcagtcag ttgctcaatg tacctataac cagaccgttc agctggatat   21120
tacggccttt ttaaagaccg taaagaaaaa taagcacaag ttttatccgg cctttattca   21180
cattcttgcc cgcctgatga atgctcatcc ggaatttcgt atggcaatga agacggtga    21240
gctggtgata tgggatagtg ttcacccttg ttacaccgtt ttccatgagc aaactgaaac   21300
gttttcatcg ctctggagtg aataccacga cgatttccgg cagtttctac acatatattc   21360
gcaagatgtg gcgtgttacg gtgaaaacct ggcctatttc cctaaagggt ttattgagaa   21420
tatgttttc gtctcagcca atccctgggt gagtttcacc agttttgatt taaacgtggc     21480
caatatggac aacttcttcg ccccgttttt caccatgggc aaatattata cgcaaggcga    21540
caaggtgctg atgccgctgg cgattcaggt tcatcatgcc gtttgtgatg cttccatgt    21600
cggcagaatg cttaatgaat tacaacagta ctgcgatgag tggcagggcg ggcgtaacc    21660
taggtgacag aagtcaaaag cctccggtcg gaggcttttg actttctgct agatcggccg   21720
catcgaatat aacttcgtat aatgtatgct atacgaagtt attagcgatg agctcggact   21780
tccattgttc attccacgga caaaaacaga gaaggaaac gacagaggcc aaaaagctcg    21840
ctttcagcac ctgtcgtttc ctttcttttc agagggtatt ttaaataaaa acattaagtt   21900
atgacgaaga agaacggaaa cgccttaaac cggaaaattt tcataaatag cgaaaacccg   21960
cgaggtcgcc gccccgtaac ctgtcggatc accggaaagg acccgtaaag tgataatgat   22020
tatcatctac atatcacaac gtgcgtggag gccatcaaac cacgtcaaat aatcaattat   22080
gacgcaggta tcgtattaat tgatctgcat caacttaacg taaaagcaac ttcagacaat   22140
acaaatcagc gacactgaat acggggcaac ctcatgtccg agctcgcgag ctcgtcgaca   22200
gcgacacact tgcatcggat gcagcccggt taacgtgccg gcacggcctg ggtaaccagg   22260
tattttgtcc acataaccgt gcgcaaaatg ttgtggataa gcaggacaca gcagcaatcc   22320
acagcaggca tacaaccgca caccgaggtt actccgttct acaggttacg acgaccatgt   22380
caatacttgc ccttgacagg cattgatgga atcgtagtct cacgctgata gtctgatcga   22440
caatacaagt gggaccgtgg tcccagaccg ataatcagac cgacaacacg agtgggatcg   22500
tggtcccaga ctaataatca gaccgacgat acgagtggga ccgtggtccc agactaataa   22560
tcagaccgac gatacgagtg gaccgtggt tccagactaa taatcagacc gacgatacga    22620
gtgggaccgt ggtcccagac taataatcag accgacgata cgagtgggac catggtccca   22680
gactaataat cagaccgacg atacgagtgg accgtggtc ccagtctgat tatcagaccg     22740
acgatacgag tgggaccgtg gtcccagact aataatcaga ccgacgatac gagtgggacc   22800
gtggtcccag actaataatc agaccgacga tacgagtggg accgtggtcc cagtctgatt   22860
atcagaccga cgatacaagt ggaacagtgg gcccagagag aatattcagg ccagttatgc   22920
tttctggcct gtaacaaagg acattaagta aagacagata aacgtagact aaaacgtggt   22980
cgcatcaggg tgctggcttt tcaagttcct taagaatggc ctcaatttc tctatacact      23040
```

```
cagttggaac acgagacctg tccaggttaa gcaccatttt atcgcccttta tacaatactg   23100 tcgctccagg agcaaactga tgtcgtgagc ttaaactagt tcttgatgca gatgacgttt   23160
taagcacaga agttaaaaga gtgataactt cttcagcttc aaatatcacc ccagcttttt   23220
tctgctcatg aaggttagat gcctgctgct taagtaattc ctctttatct gtaaaggctt   23280
tttgaagtgc atcacctgac cgggcagata gttcaccggg gtgagaaaaa agagcaacaa   23340
ctgatttagg caatttggcg gtgttgatac agcgggtaat aatcttacgt gaaatatttt   23400
ccgcatcagc cagcgcagaa atatttccag caaattcatt ctgcaatcgg cttgcataac   23460
gctgaccacg ttcataagca cttgttgggc gataatcgtt acccaatctg gataatgcag   23520
ccatctgctc atcatccagc tcgccaacca gaacacgata atcactttcg gtaagtgcag   23580
cagctttacg acggcgactc ccatcggcaa tttctatgac accagatact cttcgaccga   23640
acgccggtgt ctgttgacca gtcagtagaa aagaagggat gagatcatcc agtgcgtcct   23700
cagtaagcag ctcctggtca cgttcattac ctgaccatac ccgagaggtc ttctcaacac   23760
tatcaccccg gagcacttca agagtaaact tcacatcccg accacataca ggcaaagtaa   23820
tggcattacc gcgagccatt actcctacgc gcgcaattaa cgaatccacc atcggggcag   23880
ctggtgtcga taacgaagta tcttcaaccg gttgagtatt gagcgtatgt tttggaataa   23940
caggcgcacg cttcattatc taatctccca gcgtggttta atcagacgat cgaaaatttc   24000
attgcagaca ggttcccaaa tagaaagagc atttctccag gcaccagttg aagagcgttg   24060
atcaatggcc tgttcaaaaa cagttctcat ccggatctga cctttaccaa cttcatccgt   24120
ttcacgtaca acatttttta gaaccatgct tccccaggca tcccgaattt gctcctccat   24180
ccacggggac tgagagccat tactattgct gtatttggta agcaaaatac gtacatcagg   24240
ctcgaaccct ttaagatcaa cgttcttgag cagatcacga agcatatcga aaaactgcag   24300
tgcggaggtg tagtcaaaca actcagcagg cgtgggaaca atcagcacat cagcagcaca   24360
tacgacatta atcgtgccga tacccaggtt aggcgcgctg tcaataacta tgacatcata   24420
gtcatgagca acagtttcaa tggccagtcg gagcatcagg tgtggatcgg tgggcagttt   24480
accttcatca aatttgccca ttaactcagt ttcaatacgg tgcagagcca gacaggaagg   24540
aataatgtca agccccggcc agcaagtggg ctttattgca taagtgacat cgtccttttc   24600
cccaagatag aaaggcagga gagtgtcttc tgcatgaata tgaagatctg gtacccatcc   24660
gtgatacatt gaggctgttc cctggggtc gttaccttcc acgagcaaaa cacgtagccc   24720
cttcagagcc agatcctgag caagatgaac agaaactgag gttttgtaaa cgcctccttt   24780
atgggcagca cccccgatca ccggtggaaa tacgtcttca gcacgtcgca atcgcgtacc   24840
aaacacatca cgcatatgat taatttgttc aattgtataa ccaacacgtt gctcaacccg   24900
tcctcgaatt tccatatccg ggtgcggtag tcgccctgct ttctcggcat ctctgatagc   24960
ctgagaagaa accccaacta aatccgctgc ttcacctatt ctccagcgcc gggttatttt   25020
cctcgcttcc gggctgtcat cattaaactg tgcaatggcg atagccttcg tcatttcatg   25080
accagcgttt atgcactggt taagtgtttc catgagtttc attctgaaca tcctttaatc   25140
attgctttgc gtttttttat taaatcttgc aatttactgc aaagcaacaa caaaatcgca   25200
aagtcatcaa aaaaccgcaa agttgtttaa aataagagca acactacaaa aggagataag   25260
aagagcacat acctcagtca cttattatca ctagcgctcg ccgcagccgt gtaaccgagc   25320
atagcgagcg aactggcgag gaagcaaaga agaactgttc tgtcagatag ctcttacgct   25380
```

```
cagcgcaaga agaaatatcc accgtgggaa aaactccagg tagaggtaca cacgcggata    25440
gccaattcag agtaataaac tgtgataatc aaccctcatc aatgatgacg aactaacccc    25500
cgatatcagg tcacatgacg aagggaaaga gaaggaaatc aactgtgaca aactgccctc    25560
aaatttggct tccttaaaaa ttacagttca aaaagtatga gaaatccat gcaggctgaa     25620 ggaaacagca aaactgtgac aaattaccct cagtaggtca gaacaaatgt gacgaaccac    25680
cctcaaatct gtgacagata accctcagac tatcctgtcg tcatggaagt gatatcgcgg    25740
aaggaaaata cgatatgagt cgtctggcgg cctttctttt tctcaatgta tgagaggcgc    25800
attggagttc tgctgttgat ctcattaaca cagacctgca ggaagcggcg gcggaagtca    25860
ggcatacgct ggtaactttg aggcagctgg taacgctcta tgatccagtc gatttcaga    25920 gagacgatgc ctgagccatc cggcttacga tactgacaca gggattcgta taaacgcatg    25980
gcatacggat tggtgatttc ttttgtttca ctaagccgaa actgcgtaaa ccggttctgt    26040
aacccgataa agaagggaat gagatatggg ttgatatgta cactgtaaag ccctctggat    26100
ggactgtgcg cacgtttgat aaaccaagga aaagattcat agccttttc atcgccggca    26160 tcctcttcag ggcgataaaa aaccacttcc ttccccgcga aactcttcaa tgcctgccgt    26220
atatccttac tggcttccgc agaggtcaat ccgaatattt cagcatattt agcaacatgg    26280
atctcgcaga taccgtcatg ttcctgtagg gtgccatcag attttctgat ctggtcaacg    26340
aacagataca gcatacgttt ttgatcccgg gagagactat atgccgcctc agtgaggtcg    26400
tttgactgga cgattcgcgg gctatttta cgtttcttgt gattgataac cgctgtttcc    26460
gccatgacag atccatgtga agtgtgacaa gtttttagat tgtcacacta aataaaaaag    26520
agtcaataag cagggataac tttgtgaaaa aacagcttct tctgagggca atttgtcaca    26580
gggttaaggg caatttgtca cagacaggac tgtcatttga gggtgatttg tcacactgaa    26640
agggcaattt gtcacaacac cttctctaga accagcatgg ataaaggcct acaaggcgct    26700
ctaaaaaaga agatctaaaa actataaaaa aaataattat aaaatatcc ccgtggataa     26760 gtggataacc ccaagggaag ttttttcagg catcgtgtgt aagcagaata tataagtgct    26820
gttccctggt gcttcctcgc tcactcgacc gggagggttc gagaaggggg ggcaccccc    26880 ttcggcgtgc gcggtcacgc gcacagggcg cagccctggt taaaaacaag gtttataaat    26940
attggtttaa aagcaggtta aaagacaggt tagcggtggc cgaaaaacgg gcggaaaccc    27000
ttgcaaatgc tggattttct gcctgtggac agcccctcaa atgtcaatag gtgcgcccct    27060
catctgtcag cactctgccc ctcaagtgtc aaggatcgcg cccctcatct gtcagtagtc    27120
gcgcccctca agtgtcaata ccgcagggca cttatcccca ggcttgtcca catcatctgt    27180
gggaaactcg cgtaaaatca ggcgttttcg ccgatttgcg aggctggcca gctccacgtc    27240
gccggccgaa atcgagcctg cccctcatct gtcaacgccg cgccgggtga tcggcccct    27300 caagtgtcaa cgtccgcccc tcatctgtca gtgagggcca gttttccgc gaggtatcca    27360 caacgccggc ggccggccgc ggtgtctcgc acacggcttc gacggcgttt ctggcgcgtt    27420
tgcagggcca tagacggccg ccagcccagc ggcgagggca accagccgag ggcttcgccc    27480
tgtcgctcga ctgcggcgag cactactggc tgtaaaagga cagaccacat catggttctg    27540
tgttcattag gttgttctgt ccattgctga cataatccgc tccacttcaa cgtaacaccg    27600
cacgaagatt tctattgttc ctgaaggcat attcaaatcg ttttcgttac gcttgcagg    27660 catcatgaca gaacactact tcctataaac gctacacagg ctcctgagat taataatgcg    27720
gatctctacg ataatgggag attttcccga ctgtttcgtt cgcttctcag tggataacag    27780
```

```
ccagcttctc tgtttaacag acaaaaacag catatccact cagttccaca tttccatata    27840
aaggccaagg catttattct caggataatt gtttcagcat cgcaaccgca tcagactccg    27900
gcatcgcaaa ctgcacccgg tgccgggcag ccacatccag cgcaaaaacc ttcgtgtaga    27960
cttccgttga actgatggac ttatgtccca tcaggctttg cagaactttc agcggtatac    28020
cggcatacag catgtgcatc gcataggaat ggcggaacgt atgtggtgtg accggaacag    28080
agaacgtcac accgtcagca gcagcggcgg caaccgcctc cccaa                    28125

<210> SEQ ID NO 2
<211> LENGTH: 11628
<212> TYPE: DNA
<213> ORGANISM: Artificial Sequence
<220> FEATURE:
<223> OTHER INFORMATION: First and Second Cassettes

<400> SEQUENCE: 2
gacattgatt attgactagt tattaatagt aatcaattac gggtcatta gttcatagcc       60 catatatgga gttccgcgtt acataactta cggtaaatgg cccgcctggc tgaccgccca      120 acgaccccg cccattgacg tcaataatga cgtatgttcc catagtaacg ccaatagggga     180 ctttccattg acgtcaatgg gtggagtatt tacggtaaac tgcccacttg gcagtacatc     240
aagtgtatca tatgccaagt ccgcccccta ttgacgtcaa tgacggtaaa tggcccgcct     300
ggcattatgc ccagtacatg accttacggg actttcctac ttggcagtac atctacgtat     360
tagtcatcgc tattaccatg gtcgaggtg agccccacgt tctgcttcac tctccccatc      420 tccccccct ccccacccc aattttgtat ttatttattt tttaattatt ttgtgcagcg       480 atggggggcgg gggggggggg ggcgcgcgcc aggcggggcg gggcggggcg aggggcgggg     540
cggggcgagg cggagaggtg cggcggcagc caatcagagc ggcgcgctcc gaaagtttcc     600
ttttatggcg aggcggcggc ggcggcggcc ctataaaaag cgaagcgcgc ggcgggcggg     660
agtcgctgcg ttgccttcgc cccgtgcccc gctccgcgcc gcctcgcgcc gcccgccccg     720
gctctgactg accgcgttac tcccacaggt gagcgggcgg gacggccctt ctcctccggg     780
ctgtaattag cgcttggttt aatgacggct cgtttctttt ctgtggctgc gtgaaagcct     840
taaagggctc cggagggcc ctttgtgcgg gggggagcgg ctcgggggg tgcgtgcgtgt      900 gtgtgtgcgt gggagcgcc gcgtgcgcc cgcgctgccc ggcggctgtg agcgctgcgg      960
gcgcggcgcg ggctttgtg cgctccgcgt gtgcgcgagg ggagcgcggc cggggcggt     1020 gccccgcggt gcggggggc tgcgagggga acaaaggctg cgtgcgggt gtgtgcgtgg    1080 gggggtgagc aggggtgtg ggcgcggcgg tcggctgta acccccccct gcacccccct     1140
ccccgagttg ctgagcacgg cccggcttcg ggtgcgggc tccgtgcggg gcgtggcgcg    1200
gggctcgccg tgccgggcgg ggggtggcgg caggtggggg tgccgggcgg ggcggggccg    1260
cctcgggccg gggagggctc gggggagggg cgcggcggcc ccgagcgcc ggcggctgtc     1320 gaggcgcggc gagccgcagc cattgccttt tatggtaatc gtgcgagagg gcgcagggac    1380
ttcctttgtc ccaaatctgg cggagccgaa atctgggagg cgccgccgca ccccctctag    1440
cgggcgcggg cgaagcggtg cggcgccggc aggaaggaaa tgggcgggga gggccttcgt    1500
gcgtcgccgc gccgccgtcc ccttctccat ctccagcctc ggggctgccg cagggggacg    1560
gctgccttcg ggggggacgg ggcagggcgg ggttcggctt ctggcgtgtg accggcggct    1620
ctagagcctc tgctaaccat gttcatgcct tcttctttt cctacagctc ctgggcaacg    1680
```

```
tgctggttat tgtgctgtct catcattttg caaagaatt cgcccgggca gatccgccgc    1740
cactgccacc atgggatcaa gatcgccaaa aagaagaga aggtgccga agaagcatgc    1800 agcaccacca aaaaaaaac gaaaagtaga agacccacga ggcaacacca gcggcgtgct    1860
gagcaccccc aaggccaaga gggccaagca ccccccggc accgagaagc ccaggagcag    1920
gagccagagc gagcagcccg ccacctgccc catctgctac gccgtgatca ggcagagcag    1980
gaacctgagg aggcacctgg agctgaggca cttcgccaag cccggcgtgg atccaccggt    2040
cggcagcggc gagggccgcg gcagcctgct gacctgcggc gacgtggagg agaacccgg    2100 ccccatggtg agcaagggcg aggagctgtt caccggggtg gtgcccatcc tggtcgagct    2160
ggacggcgac gtaaacggcc acaagttcag cgtgtccggc gagggcgagg gcgatgccac    2220
ctacggcaag ctgaccctga agttcatctg caccaccggc aagctgcccg tgccctggcc    2280
caccctcgtg accaccctgc gatcgcccct attaccctgt tatccctagg ataaacctcg    2340
agccgttact tagaaccaca aagtgggaat caagagaaaa acaatgatcc cacgagagat    2400
ctatagatct atagatcatg agtgggagga atgagctggc ccttaatttg gttttgcttg    2460
tttaaattat gatatccaac tatgaaacat tatcataaag caatagtaaa gagccttcag    2520
taaagagcag gcatttatct aatcccaccc cacccccacc cccgtagctc caatccttcc    2580
attcaaaatg taggtactct gttctcaccc ttcttaacaa agtatgacag gaaaaacttc    2640
cattttagtg gacatctta ttgtttaata gatcatcaat ttctgcatcc cggggatctg    2700
atatcatcga tgcatggggt cgtgcgctcc tttcggtcgg cgctgcggg tcgtggggcg    2760 ggcgctattc ctttgccctc ggacgagtgc tggggcgtcg gtttccacta tcggcgagta    2820
cttctacaca gccatcggtc cagacggccg cgcttctgcg ggcgatttgt gtacgcccga    2880
cagtcccggc tccggatcgg acgattgcgt cgcatcgacc ctgcgcccaa gctgcatcat    2940
cgaaattgcc gtcaaccaag ctctgataga gttggtcaag accaatgcgg agcatatacg    3000
cccggagccg cggcgatcct gcaagctccg gatgcctccg ctcgaagtag cgcgtctgct    3060
gctccataca agccaaccac ggcctccaga agaagatgtt ggcgacctcg tattgggaat    3120
ccccgaacat cgcctcgctc cagtcaatga ccgctgttat gcggccattg tccgtcagga    3180
cattgttgga gccgaaatcc gcgtgcacga ggtgccggac ttcggggcag tcctcggccc    3240
aaagcatcag ctcatcgaga gcctgcgcga cggacgcact gacggtgtcg tccatcacag    3300
tttgccagtg atacacatgg ggatcagcaa tcgcgcatat gaaatcacgc catgtagtgt    3360
attgaccgat tccttgcggt ccgaatgggc cgaacccgct cgtctggcta agatcggccg    3420
cagcgatcgc atccatggcc tccgcgaccg gctgcagaac agcgggcagt tcggtttcag    3480
gcaggtcttg caacgtgaca ccctgtgcac ggcgggagat gcaataggtc aggctctcgc    3540
tgaattcccc aatgtcaagc acttccggaa tcgggagcgc ggccgatgca aagtgccgat    3600
aaacataacg atctttgtag aaaccatcgg cgcagctatt taccggagg acatatccac    3660 gccctcctac atcgaagctg aaagcacgag attcttcgcc ctccgagagc tgcatcaggt    3720
cggagacgct gtcgaacttt tcgatcagaa acttctcgac agacgtcgcg gtgagttcag    3780
gcttttcccc catggtaagc ttcagctgct cgatcgagat ctagatggat gcaggtcgaa    3840
aggcccggag atgaggaaga ggagaacagc gcggcagacg tgcgcttttg aagcgtgcag    3900
aatgccgggc ctccggagga ccttcgggcg cccgccccgc ccctgagccc gcccctgagc    3960
ccgcccccgg acccacccct tcccagcctc tgagcccaga aagcgaagga gcaaagctgc    4020
tattggccgc tgccccaaag gcctacccgc ttccattgct cagcggtgct gtccatctgc    4080
```

```
acgagactag tgagacgtgc tacttccatt tgtcacgtcc tgcacgacgc gagctgcggg    4140 gcgggggga  acttcctgac taggggagga gtagaaggtg gcgcgaaggg gccaccaaag    4200
aacggagccg gttggcgcct accggtggat gtggaatgtg tgcgaggcca gaggccactt    4260
gtgtagcgcc aagtgcccag cggggctgct aaagcgcatg ctccagactg ccttgggaaa    4320
agcgcctccc ctacccggta gaatttcgag gtcgaagggc gcagtagtcc agggtttcct    4380
tgatgatgtc atacttatcc tgtccctttt ttttccacag ggatcctcgg ggacaccaaa    4440
tatggcgatc tcggccttt  cgtttcttgg agctgggaca tgtttgccat cgatccatct    4500
accaccagaa cggccgttag atctgctgcc accgttgttt ccaccgaaga aaccaccgtt    4560
gccgtaacca ccacgacggt tgttgctaaa gaagctgcca ccgccacggc caccgttgta    4620
gccgccgttg ttgttattgt agttgctcat gttatttctg gcacttcttg gttttcctct    4680
taagtgagga ggaacataac cattctcgtt gttgtcgttg atgcttaaat tttgcacttg    4740
ttcgctcagt tcagccataa tatgaaatgc ttttcttgtt gttcttacgg ataccacttt    4800
gccacctatc accacaacta actttttccc gttcctccat ctcttttata ttttttttct    4860
cgatcgaggg atctttgtga aggaaccttg cttctgtggt gtgacataat tggacaaact    4920
acctacagag atttaaagct ctaaggtaaa tataaaattt ttaagtgtat aatgtgttaa    4980
actactgatt ctaattgttt gtgtatttta gattccaacc tatggaactg atgaatggga    5040
gcagtggtgg aatgccttta atgaggaaaa cctgttttgc tcagaagaaa tgccatctag    5100
tgatgatgag gctactgctg actctcaaca ttctactcct ccaaaaaaga agagaaaggt    5160
agaagacccc aaggactttc cttcagaatt gctaagtttt ttgagtcatg ctgtgtttag    5220
taatagaact cttgcttgct ttgctatta  caccacaaag gaaaagctg cactgctata    5280 caagaaaatt atggaaaaat attctgtaac ctttataagt aggcataaca gttataatca    5340
taacatactg ttttttctta ctccacacag gcatagagtg tctgctatta ataactatgc    5400
tcaaaaattg tgtaccttta gctttttaat ttgtaaaggg gttaataagg aatatttgat    5460
gtatagtgcc ttgactagag atcataatca gccataccac atttgtagag gttttacttg    5520
ctttaaaaaa cctcccacac ctccccctga acctgaaaca taaaatgaat gcaattgttg    5580
ttgttaactt gtttattgca gcttataatg gttacaaata agcaatagc  atcacaaatt    5640 tcacaaataa agcatttttt tcactgcatt ctagttgtgg tttgtccaaa ctcatcaatg    5700
tatcttatca tgtctggtcg agggatcttt gtgaaggaac cttacttctg tggtgtgaca    5760
taattggaca aactacctac agagatttaa agctctaagg taaatataaa attttaagt     5820 gtataatgtg ttaaactact gattctaatt gtttgtgtat tttagattcc aacctatgga    5880
actgatgaat gggagcagtg gtggaatgcc tttaatgagg aaaacctgtt ttgctcagaa    5940
gaaatgccat ctagtgatga tgaggctact gctgactctc aacattctac tcctccaaaa    6000
aagaagagaa aggtagaaga ccccaaggac tttccttcag aattgctaag ttttttgagt    6060
catgctgtgt ttagtaatag aactcttgct tgctttgcta tttacaccac aaaggaaaaa    6120
gctgcactgc tatacaagaa aattatgaa  aaatattctg taacctttat aagtaggcat    6180
aacagttata atcataacat actgtttttt cttactccac acaggcatag agtgtctgct    6240
attaataact atgctcaaaa attgtgtacc tttagctttt taatttgtaa aggggttaat    6300
aaggaatatt tgatgtatag tgccttgact agagatcata atcagccata ccacatttgt    6360
agaggtttta cttgctttaa aaaacctccc acacctcccc ctgaacctga acataaaat     6420
```

```
gaatgcaatt gttgttgtta acttgtttat tgcagcttat aatggttaca aataaagcaa    6480
tagcatcaca aatttcacaa ataaagcatt tttttcactg cattctagtt gtggtttgtc    6540
caaactcatc aatgtatctt atcatgtctg gtcgagggat ctttgtgaag gaaccttact    6600
tctgtggtgt gacataattg gacaaactac ctacagagat ttaaagctct aaggtaaata    6660
taaaattttt aagtgtataa tgtgttaaac tactgattct aattgtttgt gtattttaga    6720
ttccaaccta tggaactgat gaatgggagc agtggtggaa tgcctttaat gaggaaaacc    6780
tgttttgctc agaagaaatg ccatctagtg atgatgaggc tactgctgac tctcaacatt    6840
ctactcctcc aaaaagaag agaaaggtag aagaccccaa ggactttcct tcagaattgc    6900 taagttttttt gagtcatgct gtgtttagta atagaactct tgcttgcttt gctatttaca    6960
ccacaaagga aaaagctgca ctgctataca agaaaattat ggaaaaatat tctgtaacct    7020
ttataagtag gcataacagt tataatcata acatactgtt ttttcttact ccacacaggc    7080
atagagtgtc tgctattaat aactatgctc aaaaattgtg taccttttagc ttttaatttt    7140 gtaaggggt taataaggaa tatttgatgt atagtgcctt gactagagat cataatcagc    7200
cataccacat ttgtagaggt tttacttgct ttaaaaaacc tcccacacct cccctgaac    7260 ctgaaacata aaatgaatgc aattgttgtt gttaacttgt ttattgcagc ttataatggt    7320
tacaaataaa gcaatagcat cacaaatttc acaaataaag cattttttc actgcattct    7380 agttgtggtt tgtccaaact catcaatgta tcttatcatg tctggtcgag ggatctttgt    7440
gaaggaacct tacttctgtg gtgtgacata attggacaaa ctacctacag agatttaaag    7500
ctctaaggta aatataaaat ttttaagtgt ataatgtgtt aaactactga ttctaattgt    7560
ttgtgtattt tagattccaa cctatggaac tgatgaatgg gagcagtggt ggaatgcctt    7620
taatgaggaa aacctgtttt gctcagaaga aatgccatct agtgatgatg aggctactgc    7680
tgactctcaa cattctactc ctccaaaaaa gaagagaaag gtagaagacc caaggactt    7740 tccttcagaa ttgctaagtt ttttgagtca tgctgtgttt agtaatagaa ctcttgcttg    7800
ctttgctatt tacaccacaa aggaaaaagc tgcactgcta acaagaaaaa ttatggaaaaa    7860 atattctgta acctttataa gtaggcataa cagttataat cataacatac tgttttttct    7920
tactccacac aggcatagag tgtctgctat taataactat gctcaaaaat tgtgtacctt    7980
tagcttttta atttgtaaag gggttaataa ggaatatttg atgtatagtg ccttgactag    8040
agatcataat cagccatacc acatttgtag aggttttact tgctttaaaa aacctcccac    8100 acctcccccct gaacctgaaa cataaaatga atgcaattgt tgttgttaac ttgtttattg    8160
cagcttataa tggttacaaa taaagcaata gcatcacaaa tttcacaaat aaagcatttt    8220
tttcactgca ttctagttgt ggtttgtcca aactcatcaa tgtatcttat catgtctgga    8280
attccgcaat ctagacacca tggcttgagt aagtctgcag ctcgagaaac aataaaagtg    8340
cacaccttaa aaatgaggcc aagtgtgact ttgtggtgtg gctgggttgg gggcagcaga    8400
gggtgaaccc tgcaggaggg tgaaccctgc aaaagggtgg ggcagtgggg gccaacttgt    8460
ccttacccag agtgcaggtg tgtggagatc cctcctgcct tgacattgag cagccttaga    8520
gggtggggga ggctcagggg tcaggtctct gttcctgctt attggggagt tcctggcctg    8580
gcccttctat gtctccccag gtaccccagt ttttctgggt tcacccagag tgcagatgct    8640
tgaggaggtg ggaagggact atttgggggt gtctggctca ggtgccatgc ctcactgggg    8700
ctggttggca cctgcatttc ctgggagtgg ggctgtctca gggtagctgg gcacggtgtt    8760
cccttgagtg ggggtgtagt gggtgttcct agctgccacg cctttgcctt cacctagcta    8820
```

```
gcatctagat taattaagtt cactgccgta taggcagcta agaaaataaa agttcactgc   8880
cgtataggca gctaagaaaa ataaagttca ctgccgtata ggcagctaag aaactaggga   8940
taacagggta ataggggcga tcgctgacca ccctgtcaca cggtgtgcag tgcttcagcc   9000
gctaccccga ccacatgaag cagcacgact tcttcaagtc cgccatgccc gaaggctacg   9060
tccaggagcg caccatcttc ttcaaggacg acggcaacta caagacccgc gccgaggtga   9120
agttcgaggg cgacaccctg gtgaaccgca tcgagctgaa gggcatcgac ttcaaggagg   9180
acggcaacat cctggggcac aagctggagt acaactacaa cagccacaac gtctatatca   9240
tggccgacaa gcagaagaac ggcatcaagg tgaacttcaa gatccgccac aacatcgagg   9300
acggcagcgt gcagctcgcc gaccactacc agcagaacac ccccatcggc gacggccccg   9360
tgctgctgcc cgacaaccac tacctgagca cccagtccgc cctgagcaaa gaccccaacg   9420
agaagcgcga tcacatggtc ctgctggagt tcgtgaccgc cgccgggatc actctcggca   9480
tggacgagct gtacaagtaa taaggccggc gcgccgcggc cgctacgtaa attccgcccc   9540
tctccctccc cccccccctaa cgttactggc cgaagccgct tggaataagg ccggtgtgcg   9600
tttgtctata tgttattttc caccatattg ccgtcttttg gcaatgtgag ggcccggaaa   9660
cctggccctg tcttcttgac gagcattcct aggggtcttt cccctctcgc caaaggaatg   9720
caaggtctgt tgaatgtcgt gaaggaagca gttcctctgg aagcttcttg aagacaaaca   9780
acgtctgtag cgacccttg caggcagcgg aaccccccac ctggcgacag gtgcctctgc   9840
ggccaaaagc cacgtgtata agatacacct gcaaaggcgg cacaaccccca gtgccacgtt   9900 gtgagttgga tagttgtgga aagagtcaaa tggctctcct caagcgtatt caacaagggg   9960
ctgaaggatg cccagaaggt acccattgt atgggatctg atctgggcc tcggtgcaca   10020 tgctttacat gtgtttagtc gaggttaaaa aacgtctagg ccccccgaac cacggggacg   10080
tggttttcct ttgaaaaaca cgatgataat accatggatc caaaaagaa gagaaaggta   10140 gatccaaaaa agaagagaaa ggtagatcca aaaagaaga gaaaggtagg agccacaacc   10200
atgttgagca agggcgagga ggtcatcaaa gagttcatgc gcttcaaggt gcgcatggag   10260
ggctccatga acggccacga gttcgagatc gagggcgagg cgagggccg cccctacgag   10320 ggcacccaga ccgccaagct gaaggtgacc aagggcggcc ccctgccctt cgcctgggac   10380
atcctgtccc cccagttcat gtacggctcc aaggcgtacg tgaagcaccc cgccgacatc   10440
cccgattaca agaagctgtc cttccccgag ggcttcaagt gggagcgcgt gatgaacttc   10500
gaggacggcg tctggtgac cgtgacccag gactcctccc tgcaggacgg cacgctgatc   10560
tacaaggtga agatgcgcgg caccaacttc cccccgacg ccccgtaat gcagaagaag   10620 accatgggct gggaggcctc caccgagcgc ctgtaccccc gcgacggcgt gctgaagggc   10680
gagatccacc aggccctgaa gctgaaggac ggcggccact acctggtgga gttcaagacc   10740
atctacatgg ccaagaagcc cgtgcaactg cccggctact actacgtgga caccaagctg   10800
gacatcacct cccacaacga ggactacacc atcgtggaac agtacgagcg ctccgagggc   10860
cgccaccacc tgttcctggg gcatggcacc ggcagcaccg gcagcggcag ctccggcacc   10920
gcctcctccg aggacaacaa catggccgtc atcaaagagt tcatgcgctt caaggtgcgc   10980
atggagggct ccatgaacgg ccacgagttc gagatcgagg gcgagggcga gggccgcccc   11040
tacgagggca cccagaccgc caagctgaag gtgaccaagg gcggccccct gcccttcgcc   11100
tgggacatcc tgtccccccca gttcatgtac ggctccaagg cgtacgtgaa gcaccccgcc   11160
```

-continued

```
gacatccccg attacaagaa gctgtccttc cccgagggct tcaagtggga gcgcgtgatg  11220
aacttcgagg acggcggtct ggtgaccgtg acccaggact cctccctgca ggacggcacg  11280
ctgatctaca aggtgaagat gcgcggcacc aacttccccc ccgacggccc cgtaatgcag  11340
aagaagacca tgggctggga ggcctccacc gagcgcctgt acccccgcga cggcgtgctg  11400
aagggcgaga tccaccaggc cctgaagctg aaggacggcg gccactacct ggtggagttc  11460
aagaccatct acatggccaa gaagcccgtg caactgcccg gctactacta cgtggacacc  11520
aagctggaca tcacctccca caacgaggac tacaccatcg tggaacagta cgagcgctcc  11580
gagggccgcc accacctgtt cctgtacggc atggacgagc tgtacaag              11628
```

<210> SEQ ID NO 3
<211> LENGTH: 1620
<212> TYPE: DNA
<213> ORGANISM: Artificial Sequence
<220> FEATURE:
<223> OTHER INFORMATION: Third and Fourth Cassettes

<400> SEQUENCE: 3

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacatatgg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacaacag ccacaacgtc tatatcatgg ccgacaagca gaagaacggc   480
atcaaggtga acttcaaggg ttcactgccg tataggcagc taagaaaggg gcgttcactg   540
ccgtataggc agctaagaaa cccctgttca ctgccgtata ggcagctaag aaatggcagc   600
ggcgccacca acttcagcct gctgaagcag gccggcgacg tggaggagaa ccccggcccc   660
ggatccgatc caaaaaagaa gagaaaggta gcccgcaagg tggacctgac cagctgcgac   720
cgcgagccca tccacatccc cggcagcatc cagccctgcg gctgcctgct ggcctgcgac   780
gcccaggccg tgcgcatcac ccgcatcacc gagaacgccg gcgccttctt cggccgcgag   840
accccccgcg tgggcgagct gctggccgac tacttcggcg agaccgaggc ccacgccctg   900
cgcaacgccc tggcccagag cagcgacccc aagcgccccg ccctgatctt cggctggcgc   960
gacggcctga ccggccgcac cttcgacatc agcctgcacc gccacgacgg caccagcatc  1020
atcgagttcg agcccgccgc cgccgagcag gccgacaacc ccctgcgcct gacccgccag  1080
atcatcgccc gcaccaagga gctgaagagc ctggaggaga tggccgcccg cgtgccccgc  1140
tacctgcagg ccatgctggg ctaccaccgc gtgatgctgt accgcttcgc cgacgacggc  1200
agcggcatgg tgatcggcga ggccaagcgc agcgacctgg agagcttcct gggccagcac  1260
ttccccgcca gcctggtgcc ccagcaggcc cgcctgctgt acctgaagaa cgccatccgc  1320
gtggtgagcg acagccgcgg catcagcagc cgcatcgtgc ccgagcacga cgccagcggc  1380
gccgccctgg acctgagctt cgcccacctg cgcagcatca gcccctgcca cctggagttc  1440
ctgcgcaaca tgggcgtgag cgccagcatg agcctgagca tcatcatcga cggcaccctg  1500
tggggcctga tcatctgcca ccactacgag ccccgcgccg tgcccatggc ccagcgcgtg  1560
gccgccgaga tgttcgccga cttcctgagc ctgcacttca ccgccgccca ccaccagcgc  1620
```

<210> SEQ ID NO 4
<211> LENGTH: 239
<212> TYPE: PRT
<213> ORGANISM: Artificial Sequence
<220> FEATURE:
<223> OTHER INFORMATION: EGFP-Y64H

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 5
<211> LENGTH: 476
<212> TYPE: PRT
<213> ORGANISM: Artificial Sequence
<220> FEATURE:
<223> OTHER INFORMATION: TdTomato

<400> SEQUENCE: 5

```
Met Leu Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
```

```
                65                  70                  75                  80
Pro Asp Tyr Lys Lys Leu Ser Phe Pro Glu Gly Phe Lys Trp Glu Arg
                        85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
    210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
        275                 280                 285

Leu Lys Val Thr Lys Gly Gly Pro Leu Pro Phe Ala Trp Asp Ile Leu
    290                 295                 300

Ser Pro Gln Phe Met Tyr Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Asn Phe Glu Asp Gly Gly Leu Val Thr Val Thr Gln
            340                 345                 350

Asp Ser Ser Leu Gln Asp Gly Thr Leu Ile Tyr Lys Val Lys Met Arg
        355                 360                 365

Gly Thr Asn Phe Pro Pro Asp Gly Pro Val Met Gln Lys Lys Thr Met
    370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430

Pro Gly Tyr Tyr Tyr Val Asp Thr Lys Leu Asp Ile Thr Ser His Asn
        435                 440                 445

Glu Asp Tyr Thr Ile Val Glu Gln Tyr Glu Arg Ser Glu Gly Arg His
    450                 455                 460

His Leu Phe Leu Tyr Gly Met Asp Glu Leu Tyr Lys
465                 470                 475

<210> SEQ ID NO 6
```

```
<211> LENGTH: 239
<212> TYPE: PRT
<213> ORGANISM: Artificial Sequence
<220> FEATURE:
<223> OTHER INFORMATION: EGFP

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 7
<211> LENGTH: 300
<212> TYPE: PRT
<213> ORGANISM: Artificial Sequence
<220> FEATURE:
<223> OTHER INFORMATION: iRFP

<400> SEQUENCE: 7

Ala Arg Lys Val Asp Leu Thr Ser Cys Asp Arg Glu Pro Ile His Ile
1               5                   10                  15

Pro Gly Ser Ile Gln Pro Cys Gly Cys Leu Leu Ala Cys Asp Ala Gln
            20                  25                  30

Ala Val Arg Ile Thr Arg Ile Thr Glu Asn Ala Gly Ala Phe Phe Gly
        35                  40                  45

Arg Glu Thr Pro Arg Val Gly Glu Leu Leu Ala Asp Tyr Phe Gly Glu
    50                  55                  60

Thr Glu Ala His Ala Leu Arg Asn Ala Leu Ala Gln Ser Ser Asp Pro
65                  70                  75                  80

Lys Arg Pro Ala Leu Ile Phe Gly Trp Arg Asp Gly Leu Thr Gly Arg
```

```
                    85                  90                  95
Thr Phe Asp Ile Ser Leu His Arg His Asp Gly Thr Ser Ile Ile Glu
            100                 105                 110

Phe Glu Pro Ala Ala Ala Glu Gln Ala Asp Asn Pro Leu Arg Leu Thr
        115                 120                 125

Arg Gln Ile Ile Ala Arg Thr Lys Glu Leu Lys Ser Leu Glu Glu Met
    130                 135                 140

Ala Ala Arg Val Pro Arg Tyr Leu Gln Ala Met Leu Gly Tyr His Arg
145                 150                 155                 160

Val Met Leu Tyr Arg Phe Ala Asp Asp Gly Ser Gly Met Val Ile Gly
                165                 170                 175

Glu Ala Lys Arg Ser Asp Leu Glu Ser Phe Leu Gly Gln His Phe Pro
            180                 185                 190

Ala Ser Leu Val Pro Gln Gln Ala Arg Leu Leu Tyr Leu Lys Asn Ala
        195                 200                 205

Ile Arg Val Val Ser Asp Ser Arg Gly Ile Ser Ser Arg Ile Val Pro
    210                 215                 220

Glu His Asp Ala Ser Gly Ala Ala Leu Asp Leu Ser Phe Ala His Leu
225                 230                 235                 240

Arg Ser Ile Ser Pro Cys His Leu Glu Phe Leu Arg Asn Met Gly Val
                245                 250                 255

Ser Ala Ser Met Ser Leu Ser Ile Ile Ile Asp Gly Thr Leu Trp Gly
            260                 265                 270

Leu Ile Ile Cys His His Tyr Glu Pro Arg Ala Val Pro Met Ala Gln
        275                 280                 285

Arg Val Ala Ala Glu Met Phe Ala Asp Phe Leu Ser
    290                 295                 300

<210> SEQ ID NO 8
<211> LENGTH: 23
<212> TYPE: DNA
<213> ORGANISM: Artificial Sequence
<220> FEATURE:
<223> OTHER INFORMATION: Encodes sgRNA for CrPD

<400> SEQUENCE: 8
gtagggataa cagggtaata tgg                                              23

<210> SEQ ID NO 9
<211> LENGTH: 23
<212> TYPE: DNA
<213> ORGANISM: Artificial Sequence
<220> FEATURE:
<223> OTHER INFORMATION: Coding sequence for sgRNA for CrlA

<400> SEQUENCE: 9
taacgaataa aagttacgct agg                                              23

<210> SEQ ID NO 10
<211> LENGTH: 23
<212> TYPE: DNA
<213> ORGANISM: Artificial Sequence
<220> FEATURE:
<223> OTHER INFORMATION: Coding sequence for sgRNA for CrlB

<400> SEQUENCE: 10
aacgaataaa agttacgcta ggg                                              23

<210> SEQ ID NO 11
```

```
<211> LENGTH: 23
<212> TYPE: DNA
<213> ORGANISM: Artificial Sequence
<220> FEATURE:
<223> OTHER INFORMATION: Coding sequence for sgRNA for CrlC

<400> SEQUENCE: 11
aagttacgct agggataaca ggg                                              23

<210> SEQ ID NO 12
<211> LENGTH: 23
<212> TYPE: DNA
<213> ORGANISM: Artificial Sequence
<220> FEATURE:
<223> OTHER INFORMATION: Coding sequence sgRNA for CrlD

<400> SEQUENCE: 12
aaagttacgc tagggataac agg                                              23

<210> SEQ ID NO 13
<211> LENGTH: 28
<212> TYPE: RNA
<213> ORGANISM: Artificial Sequence
<220> FEATURE:
<223> OTHER INFORMATION: Hairpin with Csy4 recognition sequence

<400> SEQUENCE: 13
guucacugcc guauaggcag cuaagaaa                                         28

<210> SEQ ID NO 14
<211> LENGTH: 20
<212> TYPE: RNA
<213> ORGANISM: Artificial Sequence
<220> FEATURE:
<223> OTHER INFORMATION: Product of cleaving hairpin with Cy4

<400> SEQUENCE: 14
guucacugcc guauaggcag                                                  20
```

MULTIFUNCTIONAL NUCLEIC ACID REPORTER CONSTRUCTS

RELATED APPLICATIONS

This application is the § 371 U.S. National Stage of International Application No. PCT/US2019/028378, filed Apr. 19, 2019, which claims priority to U.S. Provisional Application No. 62/660,539, entitled "Multifunctional Nucleic Acid Reporter Constructs", filed on Apr. 20, 2018. The contents of the aforementioned applications are hereby incorporated by reference herein in their entireties.

SEQUENCE LISTING

This application contains a Sequence Listing electronically submitted via EFS-Web to the United States Patent and Trademark Office as an ASCII text file entitled "0680.002298US01_ST25_V2" having a size of 67 kilobytes and created on Sep. 23, 2024. The information contained in the Sequence Listing is incorporated by reference herein.

FIELD

This disclosure relates generally to nucleic acid constructs for detecting the pathway choice that ensues to repair a controlled double-stranded break induced in a specific region of a genome, and the methods and tools to generate the controlled double strand break as well as for the delivery of this system in mammalian cell lines and primary culture.

BACKGROUND

Tumor cells may emerge when their precursors lose the ability to maintain the integrity of their genomic DNA sequence in response to DNA damage. Among the forms of DNA damage that are the most deleterious are double-stranded breaks (DSBs). Chronic failure to repair DSBs efficiently and perfectly may lead to a state of chronic genomic instability, a hallmark of human cancer.

When DSBs develop at different genomic loci, a choice of different DSB repair pathways (either error-free or error-prone) may be triggered, depending on a variety of factors, such as transcriptional activity at or near the affected locus, chromatin state, etc. Moreover, varying cellular and molecular scenarios such as cell cycle status, differentiation status, cell/tissue type and genetics can each influence the choice of which DSB repair pathway will be called upon to repair a given DSB. It is currently not fully known how cells select a single repair pathway to eliminate a given DSB. Since the known DSB repair pathways can be either error-free or error-prone depending on a number of variables, the choice of pathway to mend a given DSB has deep ramifications for the maintenance of genomic stability and integrity.

The four best known DSB repair pathways are homologous recombination (HR), non-homologous end joining (NHEJ), micro-homology-mediated end joining (MMEJ), and single-strand annealing (SSA). Only HR and occasionally NHEJ can promote DNA DSB repair in an error-free fashion, while the other pathways are prone to produce DNA mutations. Therefore, understanding how each DSB is repaired and how the decision is made to repair each DSB in a particular way can lead to new insights into how cancer development is both prevented and/or best treated.

However, a robust system that assesses the repertoire of repair pathways chosen at any defined genomic locus has yet to be described. Absent such a tool, it is difficult to know which pathway was preferentially chosen at a given genomic DSB and why. Thus, a cell-by-cell or organ-by-organ understanding of the biological and medical implications of error-free vs. mutagenic repair pathway choices remains a mystery. Furthermore, the nature of the preferred repair pathways that operate at the relatively few genomic sites that have been studied has been deduced indirectly, largely from studying the docking of relevant repair factors, rather than the detection of actual DNA repair products at the relevant loci (see Aymard et al., Nat Struct Mol Biol. 2014 April; 21 (4): 366-74). Moreover, most studies addressing DSB repair choice have focused primarily on the dichotomy of the HR vs. NHEJ choice. Thus, amidst a scarcity of appropriate tools, the underpinnings of MMEJ and SSA repair choice remain largely unknown, much less is known about the processes of repair pathway choice at a given genomic site.

Although the current reporter-based assays can measure the relative activity of each these DSB repair pathways individually (see, e.g., Truong et al., Proc Natl Acad Sci USA. 2013 May 7; 110 (19): 7720-5; Xie et al., Nat Struct Mol Biol. 2009 August; 16 (8): 814-8; Bennardo et al., PLOS Genet. 2008 Jun. 27; 4 (6); Pierce et al., Genes Dev. 2001 Dec. 15; 15 (24): 3237-42; Pierce et al., Genes Dev. 1999 Oct. 15; 13 (20): 2633-8), these DSB reporter assays only allow interrogating a single DSB repair pathway at a time. For studying the major four DSB pathways, multiple clonal cell lines need to be generated with different DNA reporter constructs in order to measure the relative activity of each pathway in a given biological context, which can be exceedingly labor intensive. Furthermore, no such tool has been so far reported which would allow assaying all four known DSB repair pathway choices in response to a defined, on-command DNA DSB break. Finally, the current DNA repair reporter systems require the assayed DNA locus to be transcriptionally active in order to quickly obtain a repair readout, hampering the study of DNA repair in heterochromatic regions in which DNA is not actively transcribed. Though the novel system described herein also depends on transcriptional activity for the quantitation of the reporter genes, it lays the foundation for future developments in which this will not be necessary.

Thus, it is desirable to have a single DNA repair reporter system that provides a distinguishable output for each of the four major DSB repair pathways in a cell in response to single, on-command DNA DSB break.

SUMMARY

The summary of the invention described above is non-limiting and other features and advantages of the invention will be apparent from the following detailed description of the invention, and from the claims.

The instant disclosure provides a nucleic acid reporter sequence that is useful in detecting the type of double-stranded break repair mechanism in a cell (e.g., a mammalian cell such as a human cell, a mouse cell, or a cynomolgus cell). Also provided are vectors and vector features to facilitate the delivery of this reporter sequence to a cell, cells comprising this reporter construct, and methods of detecting the type of double-stranded break repair mechanism using this reporter sequence.

Accordingly, in one aspect, the instant disclosure provides a nucleic acid (e.g., an isolated nucleic acid) comprising from 5' to 3':
(a) a first cassette comprising:
(i) a 5' portion of an open reading frame of a first reporter gene (5'RP1);
(ii) a first microhomology domain (MHD);
(iii) a sequence comprising from 5' to 3': a first double-stranded endonuclease recognition sequence (DSE-RS) recognized by a first double-stranded endonuclease (DSE), one or more sequences that lead to termination of transcription, and a second DSE-RS recognized by a second DSE;
(iv) a second MHD that has sequence homology to the first MHD; and
(v) a 3' portion of an open reading frame for an allele of the first reporter gene (3'RP1),
wherein a complete open reading frame of the first reporter gene (RP1) comprises from 5' to 3': 5'RP1, the first MHD or the second MHD, and 3'RP1, wherein removal of the sequence between the cleavage site in the first DSE-RS and the cleavage site in the second DSE-RS from the first cassette results in a reading frame shift of 3'RP1 relative to its native reading frame;
(b) a second cassette comprising:
(vi) an internal ribosome entry site sequence (IRES);
(vii) an open reading frame of a second reporter gene (RP2) that is operably linked to the IRES;
(c) a third cassette comprising a portion of an open reading frame of a third reporter gene (RP3), wherein the portion of RP3 comprises from 5' to 3':
(viii) a first portion that has sequence homology to the 5'RP1; and
(ix) a second portion that has sequence homology to the 3'RP1, wherein homologous recombination between the first and third cassettes results in a complete open reading frame of the third reporter gene comprising from 5' to 3': a 5' portion of the 5'RP1, the portion of RP3, and a 3' portion of the 3'RP1; and
(d) a fourth cassette comprising an open reading frame of a fourth reporter gene (RP4) lacking a start codon,
wherein the first and second cassettes are operably linked, and wherein the third and fourth cassettes are fused in the same reading frame.

In some embodiments, the nucleic acid comprises a linker nucleotide sequence encoding a cleavage site of a protease or a ribosomal skipping peptide, wherein the linker nucleotide sequence is located between the third cassette and the fourth cassette and is in the same reading frame as the third and fourth cassette.

In some embodiments,
(a) the RP1 gene product is capable of producing a first signal;
(b) the RP2 gene product is capable of producing a second signal;
(c) the RP3 gene product is capable of producing a third signal; and
(d) the RP4 gene product is capable of producing a fourth signal.

In some embodiments, a complete open reading frame of RP1 consists of from 5' to 3': 5'RP1, the first MHD or the second MHD, and 3'RP1. In some embodiments, the nucleic acid further comprises a promoter sequence operably linked to the first cassette. In some embodiments, the third cassette does not comprise a start codon in the RP3 reading frame.

In some embodiments, one or more of RP1, RP2, RP3, and RP4 are a fluorescent protein. In some embodiments, each of RP1, RP2, RP3, and RP4 is a fluorescent protein. In some embodiments, RP1 encodes EGFP-Y64H, optionally wherein the EGFP-Y64H comprises the amino acid sequence of SEQ ID NO: 4. In some embodiments, RP3 encodes EGFP, optionally wherein the EGFP comprises the amino acid sequence of SEQ ID NO: 5. In some embodiments, RP2 encodes tdTomato, optionally wherein the tdTomato comprises the amino acid sequence of SEQ ID NO: 6. In some embodiments, RP4 encodes iRFP670, optionally wherein the iRFP670 comprises the amino acid sequence of SEQ ID NO: 7.

In some embodiments, one or more of RP1, RP2, RP3, and RP4 are an enzyme that catalyzes a reaction with a substrate to produce an observable change in that substrate.

In some embodiments, the first and second DSE are the same DSE. In some embodiments, the first and second DSE are different DSEs.

In some embodiments, the first DSE is a rare-cutting endonuclease. In some embodiments, the second DSE is a rare-cutting endonuclease. In some embodiments, each of the first and the second DSEs is a rare-cutting endonuclease. In some embodiments, the rare-cutting endonuclease is selected from the group consisting of I-SceI and AsiSI.

In some embodiments, the first DSE is an RNA-guided DNA endonuclease associated with a guide RNA comprising a nucleotide sequence complementary to the first DSE-RS. In some embodiments, the second DSE is an RNA-guided DNA endonuclease associated with a guide RNA comprising a nucleotide sequence complementary to the second DSE-RS. In some embodiments, the first DSE is an RNA-guided DNA endonuclease associated with a guide RNA comprising a nucleotide sequence complementary to the first DSE-RS, and the second DSE is an RNA-guided DNA endonuclease associated with a guide RNA comprising a nucleotide sequence complementary to the second DSE-RS. In some embodiments, the RNA-guided DNA endonuclease is selected from the group consisting of spCas9, saCas9, and Cpf1. In some embodiments, the first and/or the second DSE-RSs comprise a promoter adjacent motif (PAM) sequence.

In some embodiments, the first DSE is a transcription activator-like nuclease (TALEN) or a zinc finger nuclease. In some embodiments, the second DSE is a transcription activator-like nuclease (TALEN) or a zinc finger nuclease. In some embodiments, the first DSE is a transcription activator-like nuclease (TALEN) or a zinc finger nuclease, and the second DSE is a transcription activator-like nuclease (TALEN) or a zinc finger nuclease.

In some embodiments, the first and/or the second DSE-RSs comprise a nucleotide sequence of low frequency in a genome. In some embodiments, the first and the second DSE-RSs are identical. In some embodiments, the first and the second DSE-RSs are different.

In some embodiments, the sequence of the first and second cassette comprises SEQ ID NO: 2. In some embodiments, the sequence of the third and fourth cassettes comprise SEQ ID NO: 3. In some embodiments, the sequence of the first and second cassette comprises SEQ ID NO: 2, and the sequence of the third and fourth cassettes comprise SEQ ID NO: 3. In some embodiments, the nucleic acid sequence comprises SEQ ID NO: 1.

In some embodiments, the transcriptional terminators of the first cassette comprise polyadenylation signal sequences. In some embodiments, the transcriptional terminators of the first cassette comprise four polyadenylation signal sequences. In some embodiments, the nucleic acid sequence comprises an additional three polyadenylation signal sequences not within the first cassette.

In some embodiments, the second cassette further comprises an open reading frame of a CRISPR-associated protein. In some embodiments, the second cassette further comprises an open reading frame of a CRISPR-associated protein comprising Csy4. In some embodiments, the open reading frame of the CRISPR-associated protein is located 3' to the RP2.

In some embodiments, the first cassette further comprises a nucleic acid sequence that forms an RNA hairpin upon transcription. In some embodiments, the fourth cassette further comprises a nucleic acid sequence that forms an RNA hairpin upon transcription. In some embodiments, the nucleic acid sequence that forms the RNA hairpin upon transcription comprises sequence that is cleaved by the CRISPR-associated protein. In some embodiments, the nucleic acid sequence that forms the RNA hairpin upon transcription forms multiple hairpins. In some embodiments, the nucleic acid sequence that forms the RNA hairpin is located between the 5' portion of the first reporter gene and the 3' portion of the first reporter gene. In some embodiments, the nucleic acid sequence that forms the RNA hairpin is located between the third reporter gene and fourth reporter gene.

In some embodiments, the nucleic acid sequence further comprises a fifth cassette comprising an additional reporter protein or proteins.

In another aspect, the instant disclosure provides a vector comprising the nucleic acid disclosed herein, and/or a nucleic acid having a sequence complementarity thereto. In some embodiments, the vector (e.g., an adenoviral vector) comprises a double-stranded DNA genome comprising the nucleic acid disclosed herein. In some embodiments, the vector (e.g., an adeno-associated viral vector) comprises a single-stranded DNA genome comprising the nucleic acid disclosed herein, or a nucleic acid having a sequence complementarity thereto. In some embodiments, the vector (e.g., a retroviral vector, such as a lentiviral vector) comprises a single-stranded RNA genome comprising the nucleic acid disclosed herein, or a nucleic acid having a sequence complementarity thereto.

In another aspect, the instant disclosure provides a cell comprising a vector comprising the nucleic acid disclosed herein. In some embodiments, the cell comprises the nucleic acid as an extrachromosomal DNA. In some embodiments, the cell comprises the nucleic acid in its chromosome. In some embodiments, the cell comprises the first DSE and/or the second DSE. In some embodiments, the cell comprises a nucleic acid encoding the first DSE and/or the second DSE, optionally wherein the nucleic acid encoding the first DSE and/or the second DSE is operably linked to a promoter sequence (e.g., an inducible promoter sequence).

In another aspect, the instant disclosure provides a method for detecting a type of double-stranded break repair mechanism in a cell, comprising:
(a) integrating a nucleic acid sequence into the genome of a cell, wherein the nucleic acid sequence comprises at least four reporter genes that generate a different signal;
(b) inducing a double-stranded break into the nucleic acid sequence;
(c) detecting at least one signal generated by at least one reporter gene, that signal being indicative of the type of double-stranded break repair mechanism.

In some embodiments, a different signal or combination of signals is detected for each of the double-stranded break repair mechanisms HR, NHEJ, MMEJ, and SSA.

In another aspect, the instant disclosure provides a method for detecting a type of double-stranded break repair mechanism in a cell comprising:
(a) obtaining a cell comprising a vector comprising a nucleic acid disclosed herein;
(b) expressing in the cell the first DSE and the second DSE, thereby generating a double-stranded break; and
(c) detecting one or more of the first, second, third, and/or fourth signals in response to the double-stranded break, wherein detection of a first, second, third, and/or fourth signal is indicative of a type of double-stranded break repair mechanism. In some embodiments, detecting only the second signal indicates that the cell used non-homologous end joining (NHEJ) to repair the double-stranded break. In some embodiments, detecting only the second signal and the third signal indicates that the cell used homologous recombination (HR) to repair the double-stranded break. In some embodiments, detecting only the first signal and the second signal indicates that the cell used microhomology-mediated end joining (MMEJ) to repair the double-stranded break. In some embodiments, detecting only the fourth signal indicates that the cell used single-strand annealing (SSA) to repair the double-stranded break.

In some embodiments, expressing in the cell the first DSE and the second DSE comprises contacting the cell with a composition comprising a nucleic acid encoding the first DSE and/or the second DSE. In some embodiments, the cell comprises a nucleic acid encoding the first DSE and/or the second DSE operably linked to an inducible promoter sequence, and expressing in the cell the first DSE and the second DSE comprises inducing the activity of the promoter sequence. In some embodiments, the cell expresses an RNA-guided DNA endonuclease, and expressing in the cell the first DSE and the second DSE comprises contacting the cell with a composition comprising a guide RNA comprising a nucleotide sequence complementary to the first DSE-RS and/or a second guide RNA comprising a nucleotide sequence complementary to the second DSE-RS.

In some embodiments, one or more of RP1, RP2, RP3, and RP4 are a fluorescent protein. In some embodiments, detecting one or more of the first, second, third, and fourth signals comprises use of flow cytometry. In some embodiments, detecting one or more of the first, second, third, and fourth signals comprises use of fluorescent microscopy.

In some embodiments, the cell is a cancer cell (e.g., derived from a patient or an experimental animal). In some embodiments, the signal(s) from the cancer cell is detected in a tumor sample, either in vivo or ex vivo. In some embodiments, the relevant cell is a normal cell (e.g., a non-cancerous cell or non-tumorous cell) from a laboratory animal (e.g., a wild-type animal, or an animal that has been genetically modified or engineered).

BRIEF DESCRIPTION OF THE FIGURES

The foregoing and other objects of the present disclosure, the various features thereof, as well as the disclosure itself may be more fully understood from the following description, when read together with the accompanying drawings.

FIG. 3G is a schematic diagram summarizing the fluorescent proteins, and associated colors, that can be detected for each of the repair pathways (see FIGS. 3C-3F).

FIG. 5A is a histogram of the percentage of GFP-positive cells detected in five different 293T cell clones stably transfected with a nucleic acid reporter construct, following transient transfection with the rare-cutting endonuclease I-SceI.

FIG. 5B is a histogram of the percentage of BFP-positive cells detected in five different 293T cell clones stably transfected with a nucleic acid reporter construct, following transient transfection with the rare-cutting endonuclease I-SceI.

FIG. 5C is a histogram of the percentage of Tomato-positive cells detected in five different 293T cell clones stably transfected with a nucleic acid reporter construct, following transient transfection with the rare-cutting endonuclease I-SceI.

FIG. 5D is a histogram of the percentage of iRFP-positive cells detected in five different 293T cell clones stably transfected with a nucleic acid reporter construct, following transient transfection with the rare-cutting endonuclease I-SceI.

FIG. 11A shows fluorescent reporter signal detected corresponding to HR. FIG. 11B shows fluorescent reporter signal detected corresponding to MMEJ. FIG. 11C shows fluorescent reporter signal detected corresponding to NHEJ. FIG. 11D shows fluorescent reporter signal detected corresponding to SSA.

As shown in FIG. 12A, the cells were FACs sorted based on the fluorescent signal they displayed. Genomic DNA was extracted from the color sorted cells in order to analyze the repair products formed. As shown in FIG. 12B, restriction enzyme digestion or PCR amplification was used to distinguish between products of the respective repair pathways. Data is shown for 293T cell clones A2, A7, B10, and B12.

FIGS. 13A-D are a set of histograms depicting detection of four different fluorescent reporter proteins in 293T cell clones A2 (FIG. 13A), A7 (FIG. 13B), B10 (FIG. 13C), and B12 (FIG. 13C) when DNA repair proteins are selectively depleted. The 293T cells were infected with the ISceI-encoding virus and then transfected with siRNAs targeted at depleting either BRCA1, BRCA2, Rad51, Rad52 or 53BP1, or the siRNA control (siGL2).

DETAILED DESCRIPTION

Figure 1A:
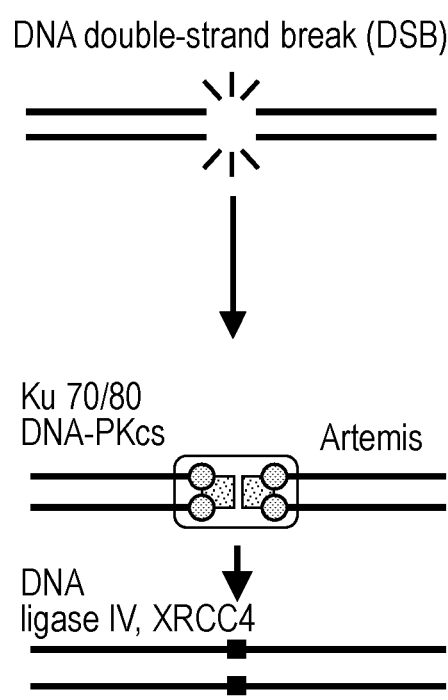
FIG. 1A is a schematic diagram of the non-homologous end joining (NHEJ) repair pathway following a double-stranded DNA break.

The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art.

That the disclosure may be more readily understood, select terms are defined below.

As used herein, the term "nucleic acid" refers to a polymer of two or more nucleotides or nucleotide analogues (such as ribonucleic acid having methylene bridge between the 2'-O and 4'-C atoms of the ribose ring) capable of hybridizing to a complementary nucleic acid. As used herein, this term includes, without limitation, DNA, RNA, LNA, and PNA. A nucleic acid may be single-stranded or double-stranded. Where the nucleic acid is single-stranded, a skilled person in the art will appreciate that the nucleic acid can be in the sense or antisense orientation relative to the direction of transcription of the reporter genes.

As used herein, the term "reporter protein" refers to a protein that is detectable by a user when expressed by a cell in a non-truncated form, and the term "reporter gene" refers to a gene encoding a reporter protein that is detectable by fluorescence, luminescence, color change, enzyme assay, or histochemistry. For example, a reporter protein may be a fluorescent protein that fluoresces when exposed to a certain wavelength of light (e.g., GFP, enhanced GFP). A reporter protein may be an enzyme that catalyzes a reaction with a substrate to produce an observable change in that substrate, such as luciferase which acts on luciferin to emit photons, or β-galactosidase which can hydrolyze X-gal (5-bromo-4-chloro-3-indolyl-β-D-galactopyranoside) to form a blue precipitate that can visualized. In some embodiments, a reporter protein is detectable by an antibody binding interaction.

As used herein, the term "fluorescent protein" refers to a protein that emits light at some wavelength after excitation by light at another wavelength. Exemplary fluorescent proteins that emit in the green spectrum range include, but are not limited to: green fluorescent protein (GFP); enhanced GFP (EGFP); superfolder GFP; AcGFP1; and ZsGreen1. Exemplary fluorescent proteins that emit light in the blue spectrum range include, but are not limited to: enhanced blue fluorescent protein (EBFP), EBFP2, Azurite, and mKalama1. Exemplary fluorescent proteins that emit light in the cyan spectrum range include, but are not limited to: cyan fluorescent protein (CFP); enhanced CFP (ECFP); Cerulean; mHoneydew; and CyPet. Exemplary fluorescent proteins that emit light in the yellow spectrum range include, but are not limited to: yellow fluorescent protein (YFP); Citrine; Venus; mBanana; ZsYellow1; and Ypet. Exemplary fluorescent proteins that emit in the orange spectrum range include, but are not limited to: mOrange; tdTomato; Exemplary fluorescent proteins that emit light in the red and far-red spectrum range include, but are not limited to: DsRed; DsRed-monomer; DsRed-Express2; mRFP1; mCherry; mStrawberry; mRaspberry; mPlum; E2-Crimson; iRFP670; iRFP682; iRFP702; iRFP720. Exemplary listings of fluorescent proteins and their characteristics may be found in Day and Davidson, Chem Soc Rev. 2009 October; 38 (10): 2887-2921, incorporated herein by reference.

Fluorescent proteins may include chimeric combinations of fluorescent proteins that transfer and receive energy through fluorescent resonance energy transfer (FRET) when exposed to a particular wavelength of light. In some embodiments, an acceptor in a FRET pair may emit light at a certain wavelength after accepting energy from a donor molecule exposed to another wavelength of light. Exemplary chimeric FRET pairs, include, but are not limited to ECFP-EYFP; mTurquoise2-SeYFP; EGFP-mCherry; and Clover-mRuby. In some embodiments, the acceptor molecule of chimeric fluorescent molecule may quench the light emission of a donor molecule exposed to its preferred wavelength of light. Quenching between different portions of chimeric fluorescent proteins may occur using a photoactivatable acceptor. For example, a chimeric fluorescent protein may include a photoactivatable GFP that can then quench photoemission by CFP. Examples of FRET proteins are discussed in Hildebrandt et al., Sensors (Basel). 2016 September; 16 (9): 1488, incorporated herein by reference.

As used herein, the term "double-stranded endonuclease recognition sequence" or "DSE-RS" refers to a nucleotide sequence that is recognized by an double-stranded endonuclease, optionally wherein the endonuclease is a rare-cutting endonuclease, an RNA-guided DNA endonuclease, a zinc-finger nuclease, or a TALEN, which cleaves both strands of DNA in or to the proximity of the double-stranded endonuclease recognition sequence. In some embodiments, the double-stranded endonuclease recognition sequence does not occur in the cellular genome at a high frequency. For example, the frequency of the double-stranded endonuclease recognition sequence in a wild-type genome (e.g., a human genome, a mouse genome, or a cynomolgus genome) may occur every 4^7 nucleotides (16,384 nucleotides) or less. In some embodiments, the double-stranded endonuclease recognition sequence may be absent in the wild-type genome. The double-stranded endonuclease recognition sequence may be recognized by more than one double-stranded endonuclease. For example, a double-stranded endonuclease recognition domain that is recognized by I-SceI may also be recognized by Cas9 with a gRNA for the same sequence.

As used herein, the term "double-stranded endonuclease" or "DSE" refers to a DNA endonuclease that creates a double-stranded break in double-stranded DNA at a specific DNA sequence. Exemplary double-stranded endonucleases include, but are not limited to, rare-cutting endonucleases, RNA-guided DNA endonucleases, zinc finger endonucleases, and TALENS.

As used herein, the term "rare-cutting endonuclease" refers to an endonuclease that cuts a nucleic acid recognition sequence that is found in a cellular genome at a frequency of once every 4^7 nucleotides (16,384 nucleotides) or less. In some embodiments, a rare-cutting endonuclease may cut a nucleic acid recognition sequence that occurs only once in a cellular genome. Exemplary rare-cutting endonucleases include, but are not limited to, NotI (a type II restriction enzyme), I-SceI (a homing endonuclease), and AsiSI.

As used herein, the term "RNA-guided DNA endonuclease" refers to an endonuclease that uses a guide RNA to selectively detect and make a double-stranded cut at a complementary genomic DNA sequence. Exemplary RNA-guided DNA endonucleases include, but are not limited to, Staphylococcus pyogenes Cas9 (spCas9), Staphylococcus aureus (saCas9), and Cpf1.

As used herein, the term "guide RNA" refers to a single-stranded RNA that includes an RNA sequence used as template by RNA-guided DNA endonucleases (such as spCas9) to specifically detect a complementary sequence in double-stranded DNA. This template RNA is called crRNA. The guide RNA may also include a transactivating crRNA (tracrRNA) with a certain sequence is required for some Cas9 endonucleases to function (such as spCas9 and saCas9).

As used herein, the term "zinc-finger nuclease" (ZFN) refers to a chimeric protein having multiple zinc finger modules that recognize a specific nucleic acid sequence, and a nucleic acid cleavage domain (e.g., FokI) that creates a double-stranded break at the recognized nucleic acid sequence. Each ZFN module can comprise two zinc fingers and recognizes a unique 6 bp sequence. In the context of this application, a ZFN may be engineered to recognize a double-stranded cutting recognition sequence that occurs at a low frequency in a genome.

As used herein, the term "transcription activator-like nucleases" (TALEN) refers to a chimeric protein comprising a TAL effector nucleic acid-binding domain engineered to bind a specific nucleic acid sequence, fused with a nucleic acid nuclease domain (e.g., FokI). Once a TAL effector nucleic acid-binding domain interacts with the double-stranded nucleic acid sequence it is engineered to bind, the nuclease domain cleaves the double-stranded nucleic acid. In the context of this application, a ZFN may be engineered to recognize a double-stranded cutting recognition sequence that occurs at a low frequency in a genome.

As used herein, the term "microhomology domain" or "MHD" refers to nucleic acid sequences that are used by cellular MMEJ double-stranded break repair mechanisms in a cell. A first microhomology domain is identical to a second microhomology domain that is 3' to the first microhomology nucleic acid sequence on the same nucleic acid strand. Both of the MHD's may be between 3 and 25 nucleotides long. The two MHD's may flank an intervening sequence. During MMEJ break repair, the non-coding strand of the 5' MHD anneals with the 3' MHD in the coding strand and allows MMEJ repair of the double-stranded break to occur.

As used herein, the term "transcriptional terminator" refers to a nucleotide sequence that is capable of ending transcription of mRNA. Such sequences are sometimes referred to as polyadenylation signals. In prokaryotes, rho-independent transcriptional terminators form a hairpin-DNA secondary structure that destabilizes the transcription complex, resulting in transcript cleavage. Rho-dependent transcriptional terminators require the helicase Rho factor to unwind the RNA-DNA helical region and end termination. In eukaryotes, transcriptional terminators may result in RNA secondary structure that induces transcript termination, or may use recruitment of one or more enzymes that terminate and cleave the mRNA transcript. Exemplary eukaryotic transcriptional terminators include, but are not limited to, human actin beta (hACTB) terminator sequence, phosphoglucokinase (PGK) terminator sequence, simian virus 40 (SV40) terminator sequence, human growth hormone (hGH) terminator sequence, bovine growth hormone (bGH) terminator sequence, and rabbit beta-globin (rbGlob) terminator sequence.

As used herein, the term "linker nucleotide sequence" refers to a nucleotide sequence that is located between two other nucleotide sequences. In some embodiments, a linker nucleotide sequence may encode an IRES, a cleavage site of a protease, or a ribosomal skipping peptide, if the linker nucleotide sequence links two coding sequences in the same reading frame. For example, if two proteins are translated with a linker nucleotide sequence encoding an amino acid sequence of a protease cleavage site (e.g., 3C or "PreScission"; enterokinase (EKT); Factor Xa (Fxa); Tobacco etch virus (TEV); or thrombin) from a multicistronic mRNA, specific proteases that are concomitantly expressed by the cell will cleave the peptide at the cleavage site. In another example, the nucleotide sequence encoding peptide 2A (such as T2A, P2A, E2A, or F2A) may be used, which causes ribosomal skipping at the end of the 2A sequence. This leaves no peptide bond between the 2A peptide and any peptide translated after the 2A peptide, and allows multiple separate proteins to be translated from a single transcript.

As used herein, the term "homologous template" is a nucleic acid with identical or nearly-identical (homologous sequence) that a cell's machinery can use as a "mold" to repair the broken ends. Since the information in the DNA is in the specific sequence of "bases", whether a broken piece of DNA will be restored to its original sequence or not depends on the homologous template that the cell will "base itself" on to mend the broken ends.

This disclosure provides in part, a construct with reporter genes useful in detecting multiple DNA repair pathways, detection of which is mutually exclusive. These pathways can be any DNA repair pathway known in the art or later determined. The construct can use any reporter gene that expresses a detectable product.

The technology described herein allows interrogation of DSB repair choices of cells, in some embodiments at specific genomic loci, in which the readout can be quickly obtained e.g., by using Fluorescence-Activated Cell Sorting (FACS). The novel concepts involved can also be applied to create transcription-independent DNA repair assays.

The technology is a composite of synthetic DNA sequences that function as a reporter construct that allows an investigator to assess the precise nature of the dominant DNA repair pathway that is applied to a DSB, for example in a defined region of the genome.

Expression or addition of specific DNA endonucleases in mammalian cells that carry the described nucleic acid reporter sequences, for example embedded at a particular genomic locus, will create a DSB at that locus. The DSB can then be repaired by any of the four major DSB repair pathways. Depending on the repair pathway chosen by the cell, a reporter protein e.g., a fluorescent protein that emits a unique fluorescent signal, will be expressed. The fluorescent signal can be readily detected (e.g., within 24 hours or less) by multicolor FACS. The design of this DSB reporter allows for one single repair event to take place after a DSB is generated within it. Once a repair product is generated, no further cutting and repair of the reporter sequences is possible. Therefore, knowing which fluorescent reporter was activated in individual cells of a population after induction of a single DSB will ultimately indicate which type of DSB repair that was chosen by the cells of interest to repair the DSB.

In some embodiments, the reporter sequence is inserted into the genome of a cell (e.g., a mammalian cell). In some embodiments, only one copy of the reporter sequence is inserted into the genome. In some embodiments, only one copy of the reporter sequence is inserted into each allele at the same locus of the genome. Such cells can be generated by single colony expansion followed by copy number analysis. Accordingly, in some embodiments, the instant disclosure provides a collection of the cells disclosed herein that are substantially homogenous. Since genome integration of the reporter is generally used to study the DSB repair pathway choices at specific genomic loci, a vector comprising the reporter sequence can further comprise homology arms for site-specific integration. A negative selection cassette can be added outside the homology arms of the vector to allow removal the cells in which the reporter construct is integrated by insertion, thereby disfavoring the isolation of viable cells with multiple copies of the reporter integrated. Accordingly, in some embodiments, the instant disclosure provides a collection of the cells disclosed herein that are heterogeneous. Such collection of cells is still useful for monitoring DSB repair pathway choice, because the cells comprising reporter sequences inserted at unintended genomic locations constitute only a small portion of the collection, and signals from these cells are diluted out in statistical analysis. A split toxic gene that encodes a functional suicidal gene product in the event of integration of more than one copy per cell can also be used to isolate and/or enrich the cells with single-copy integration. When the cell expresses more than one copy of the integrated construct results in formation from each portion of the split toxin that kills the cell. If only one portion of the split toxin gene is expressed by the cell, that expressed gene portion does not cause cell death.

Protein toxins that may be split include plant holotoxins, class II ribosome inactivating protein, plant hemitoxins, and class I ribosome inactivating protein. Further examples include, but are not limited to, saporin (SAP); pokeweed antiviral protein (PAP); bryodin 1; bouganin and gelonin or naturally occurring variants, or genetically engineered variants or fragments thereof. Toxins may also include a nuclease, for example but not limited to sarcin or restrictocin.

In some embodiments, a split toxin may be a nuclease or has endonucleolytic activity, such as a DNA nuclease or DNA endonuclease, or DNA endonuclease I or natural variants or genetically engineered variant thereof. In some embodiments, a nuclease can be a RNA nuclease or RNA endonuclease, for example but not limited to RNA endonuclease I; RNA endonuclease II; RNA endonuclease III. In some embodiments, a RNA nuclease can be for example, but not limited to angiogenin, Dicer, RNase A or variants or fragments thereof. In some embodiments, the toxin may be a proteolytic enzyme, including, but not limited to caspase enzymes; calpain enzymes; cathepsin enzymes; endoprotease enzymes; granzymes; matrix metalloproteases; pepsins; pronases; proteases; proteinases; rennin; trypsin or variants or fragments thereof.

In some embodiments, the split toxin is capable of inducing a cell death pathway in the cell. In such embodiments, effector molecules useful in the methods as disclosed herein include a pro-apoptotic molecules, such as but not limited to Hsp90; TNFα; DIABLO; BAX; inhibitors of Bcl-2; Bad; poly ADP ribose polymerase-1 (PARP-1): Second Mitochondrial-derived Activator or Caspases (SMAC); apoptosis inducing factor (AIF); Fas (also known as Apo-1 or CD95); Fas Ligand (FasL) or variants or fragments thereof. In some embodiments, the toxin is capable of sensitizing a cell to one or more secondary agents. In such embodiments, effector molecules useful in the methods as disclosed herein include, but are not limited to β-glucosidase; hypoxanthine-guianine phosphoribosyltransferase; β-lactamase; carboxylesterase HCE1; peroxidase enzyme and variants or fragments thereof. In some embodiments, a secondary agent may be an antiviral drug, such as oseltamivir; allopurinol. Further examples of split toxin genes are discussed in U.S. Patent Publication No. US20100047179A1, incorporated by reference herein.

Accordingly, in another aspect, the instant disclosure provides a method of generating a reporter cell, the method comprising contacting a cell with a nucleic acid disclosed herein. In some embodiments, the cell is a mammalian cell (e.g., a human cell). Any cell types disclosed herein can be used. In some embodiments, the method further comprises a step of single colony expansion. In some embodiments, the method further comprises a step of negative selection if the nucleic acid comprises a negative selection cassette or encodes a split toxic gene.

In another aspect, the instant disclosure provides a vector comprising the reporter sequence disclosed herein, further comprising a first homology arm 5' to the reporter sequence and a second homology arm 3' to the reporter sequence, wherein the first and second homology arms are substantially identical to two nucleotide sequences at a genomic locus. In some embodiments, the two nucleotide sequences are adjacent at the genomic locus. In some embodiments, the two nucleotide sequences are no more than 10, 20, 50, 100, 200, 500, 1,000, 2,000, or 5,000 nucleotides apart at the genomic locus. In some embodiments, the vector further comprises a negative selection cassette (e.g., a inducible or constitutive promoter region operably linked to a sequence encoding a toxic or suicide protein) 5' to the first homology arm or 3' to the second homology arm. In some embodiments, the vector further comprises a nucleotide sequence encoding a split toxic gene.

In some embodiments, the instant disclosure provides a reporter construct comprising polyadenylation signal sequences. In some embodiments the polyadenylation signal sequences function as transcriptional stop elements. In some embodiments the polyadenylation signal sequence comprises SV40-polyA sequence. In some embodiments to reporter construct comprises 1, 2, 3, 4, 5, 6, 7, 8, 9, 10, 11, 12, 13, 14, 15, 16, 17, 18, 19, or 20 polyadenylation signal sequences. In some embodiments, 1, 2, 3, 4, 5, 6, 7, 8, 9, or 10 polyadenylation signal sequences are located between the first and second microhomology domains (MHDs). In some embodiments, 1, 2, 3, 4, 5, 6, 7, 8, 9, or 10 polyadenylation signal sequences are located between the second and third reporter proteins. In some embodiments, 1, 2, 3, 4, 5, 6, 7, 8, 9, or 10 polyadenylation signal sequences are located after the fourth reporter protein.

In some embodiments the DSB reporter construct incorporates a mechanism using a ribonuclease to destroy mRNA transcripts that result from run-through transcription in the absence of DNA repair. In some embodiments the ribonuclease is a CRISPR-associated protein. In particular embodiments the ribonuclease is Csy4 (as known as Cas6). In some embodiments the DNA encoding the ribonuclease is contained within the DSB reporter construct. In some embodiments the ribonuclease is encoded by an expression cassette contained within the DSB reporter construct. In some embodiments the expression cassette is spaced 3' to the second reporter gene and 5' to the third reporter gene. In some embodiments a segment of the RNA encoded by the DSB reporter construct comprises a specific sequence that is recognized by a ribonuclease. In some embodiments a segment of the RNA encoded by the DSB reporter construct is recognizable by a CRISPR-associated protein. In some embodiments a segment of the RNA encoded by the DSB reporter construct is recognizable by Csy4. In some embodiments a segment of the RNA encoded by the DSB reporter construct is in a hairpin structure. In some embodiments the RNA encoded by the DSB reporter construct comprises 1, 2, 3, 4, 5, 6, 7, 8, 9, 10, 11, 12, 13, 14, 15, 16, 17, 18, 19, or 20 RNA hairpin structures. In some embodiments the sequence within the DSB reporter construct encoding an RNA hairpin structure or structures is located between the 5' portion of the first reporter gene and the 3' portion of the first reporter gene. In some embodiments sequence encoding three hairpin sequences in the transcript of the DSB reporter construct is located between the 5' portion of the first reporter gene and the 3' portion of the first reporter gene. In some embodiments the sequence within the DSB reporter construct encoding an RNA hairpin structure or structures is located between the third reporter gene and the fourth reporter gene. In some embodiments sequence encoding three hairpin sequences in the transcript of the DSB reporter construct is located between the third reporter gene and the fourth reporter gene. In some embodiments the polycistronic transcript of the second reporter gene and the polycistronic transcript of the fourth reporter gene each contain 1, 2, 3, 4, 5, 6, 7, 8, 9, or 10 hairpins with a RNA sequence that is recognized by a ribonuclease. In some embodiments the polycistronic transcript of the second reporter gene and the polycistronic transcript of the fourth reporter gene each contain 3 RNA hairpins with sequence that is recognized by a ribonuclease. Given that cancer chemo- and radiotherapy are strongly associated with DNA damage and repair processes, the ability to profile the DSB repair capacity of human cancers has the potential to dramatically improve prognostication and/or optimization of cancer patient therapies. The technology described herein may be used as a tool to predict tumor response from chemotherapeutics in cancer patients prior to treatment. For example, live tumor cells can be isolated from a patient's tumor. The patient tumor cells can be immortalized and cultivated in vitro or as a xenograft in rodents, and a nucleic acid reporter sequence can be introduced into the patient tumor cell culture or xenograft, either transiently or stably (e.g., using a viral vector, such as baculovirus). The cultured or xenograft tumor cells can then be assessed for one or more commonly used DSB repair pathways in those cells by exposing the cells to a double-stranded cutting endonuclease amenable to cleave the DNA construct. Depending on the preferred DNA double strand break repair pathways used by tumor cells from the patient, a drug or drug combination therapy may be administered to the patient that specifically targets and inhibits the preferred DSB repair pathway of the patient's tumor cells.

The methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

Double-Stranded Break Repair Pathways
Non-Homologous End Joining (NHEJ) Repair Pathway In the NHEJ repair pathway (also called canonical or c-NHEJ), the double stranded break is repaired using blunt end ligation of the DSB by DNA ligase IV and XRCC4, in combination with several co-factors (see FIG. 1A). The blunt ends are generated either by the DSB itself or by DNA polymerase- and/or exonuclease-mediated polishing of the non-homologous cohesive DNA ends resulting from the DSB. NHEJ can have both a fast process, and a slow process. The fast process uses the co-factors Ku70/80 and DNA-PKcs. In the slow process, the ends of the double-stranded break are processed by an additional protein Artemis is used in the joining process. The NHEJ repair pathway is potentially error-prone and homology-independent and is believed to be active throughout the cell cycle. Despite its error-prone nature, NHEJ is thought to be the major pathway that is most frequently used to repair DSBs in mammalian cells.

Homologous Recombination (HR) Repair Pathway

Figure 1B:
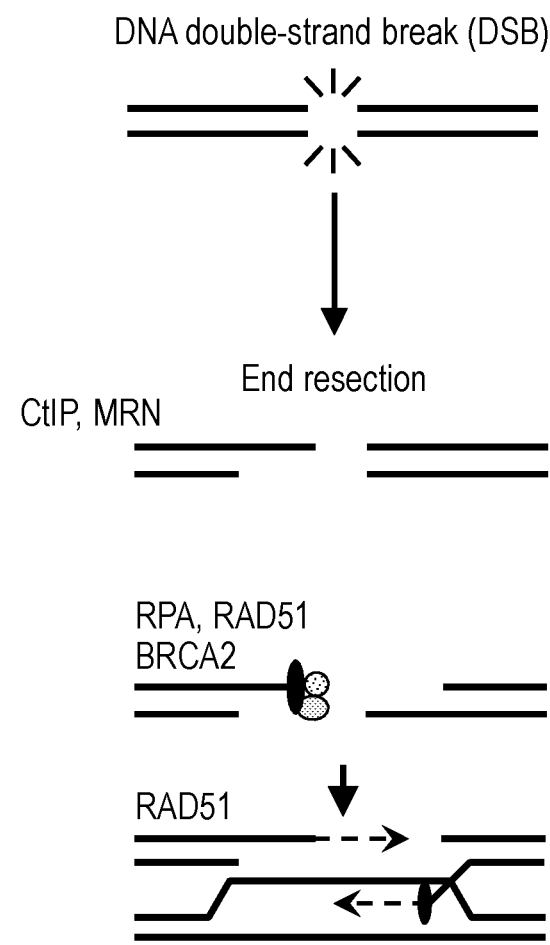
FIG. 1B is a schematic diagram of the homologous recombination (HR) repair pathway following a double-stranded DNA break.

In the HR repair pathway, the ends of the double stranded break are first resected via CtIP and MRN complexes, creating single-stranded 3' tails on each side of the DSB. The 3'tails are used with a sister or homologous chromatid which serves as the homology template for repairing the DSB (see FIG. 1B). The recombinase RAD51 mediates strand invasion of the sister chromatid by the 3'tails, along with co-factors RPA, and BRCA2 to result in a repaired DSB. Due to the requirement of a sister chomatid template, this repair pathway is mainly active during late S and G2 phases of the cell cycle. If properly controlled, HR can be the most conservative pathway to repair DSBs and can be, in most settings, considered an error-free repair pathway. This pathway is known to be upregulated in cells that are NHEJ-deficient (by genetic or pharmacological disruption).

Single Strand Annealing (SSA) Repair Pathway

Figure 1C:
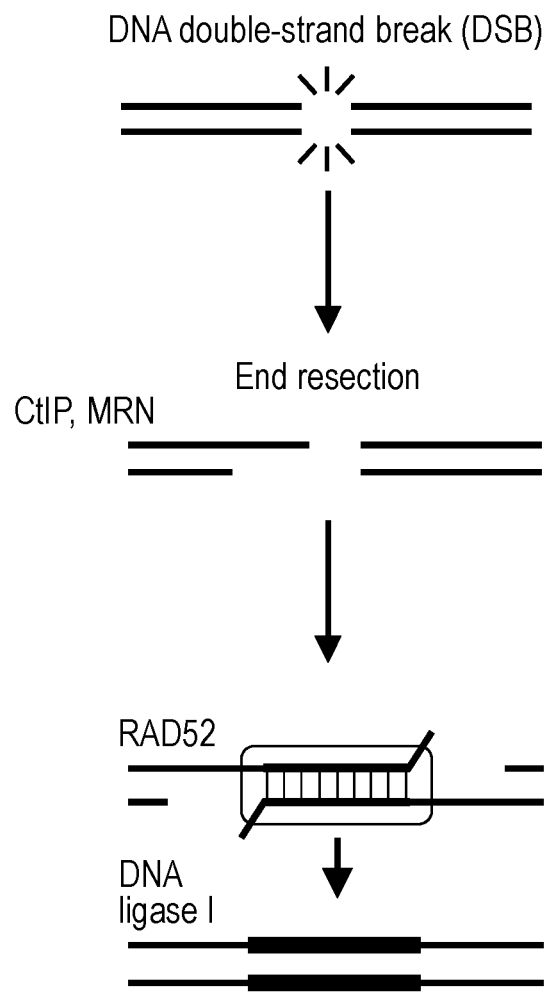
FIG. 1C is a schematic diagram of the single strand annealing (SSA) repair pathway following a double-stranded DNA break.

Alike in HR, in the SSA repair pathway the ends of the double stranded break are first resected via CtIP and MRN complex, creating single-stranded 3' tails on each side of the DSB (see FIG. 1C). The recombinase RAD52 then mediates annealing of a 3' tail with a homologous sequence from the same chromatid and deletion of any intervening sequence. Because of this, SSA is thought to be an obligate error-prone pathway. Little is known about how this pathway is regulated, though its apparent that the deficiency of several different HR factors lead to upregulation of the SSA repair pathway.

Microhomology-Mediated End Joining (MMEJ) Repair Pathway

Figure 1D:
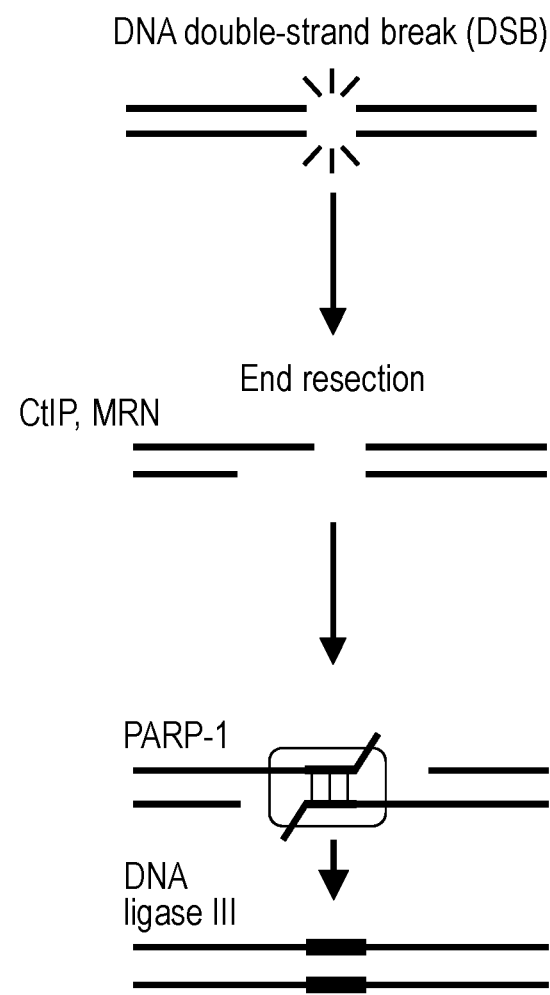
FIG. 1D is a schematic diagram of the microhomology-mediated end joining (MMEJ) repair pathway following a double-stranded DNA break.

In the MMEJ repair pathway (also called alternative end joining, or alt-EJ), the ends of the double stranded break are first resected via CtIP and MRN complex, creating single-stranded 3' tails on each side of the DSB (see FIG. 1D). Microhomology regions (1-20 bp) from each of the 3' tails on the same chromatid are combined in a PARP1- and POLQ-dependent manner and ligated together via DNA ligase III to repair the DSB.

Multifunctional DSB Reporter Construct

The multifunctional DSB reporter construct described herein uses multiple reporter genes and portions of genes, along with a double-stranded cutting recognition domain. Once inserted into the genome of a cell, a double-stranded cutting endonuclease may be administered to or expressed by the cell to create a double-stranded break at the double-stranded cutting recognition domain. The configuration of the reporter genes, reporter gene portions, and double-stranded recognition domain allows repair of the double-stranded break in the construct by any one of the four major DSB repair pathways. Irreversible expression of one of four reporter gene or reporter gene combinations allows a user to distinguishably detect which of the four DSB repair pathways was utilized in that particular cell. Likewise, analyzing the preferred repair pathway in whole populations of cells under a certain biological setting, will reveal how the relevant setting influences the most likely choice of DSB repair.

The multifunctional DSB reporter construct described herein may be introduced into a cell using transient transfection techniques (e.g., using a plasmid introduced by lipids), or it may be stably integrated into a cellular genome, such as by viral delivery (e.g., using a lentivirus or baculovirus vector). The multifunctional DBS reporter constructs may also be integrated into a specific genomic region of interest, using site-directed recombinase technology (e.g., Cre-Lox or FLP-FRT) or transposon-based technology (e.g., Sleeping Beauty transposon/SB100X). Electroporation is another of such methods that can be used.

Figure 2:
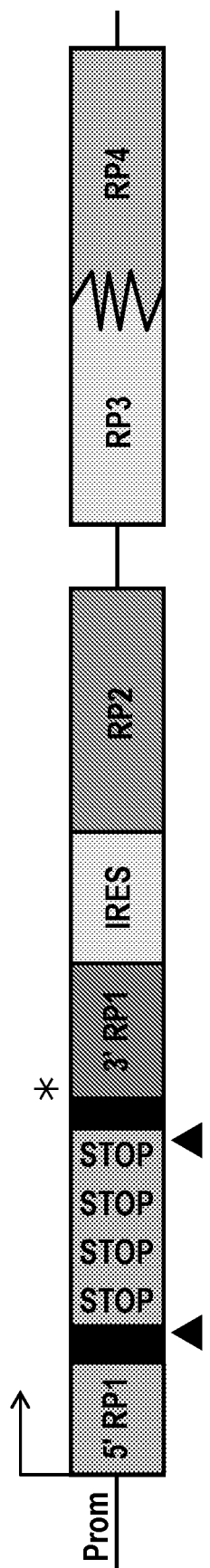
FIG. 2. is a schematic diagram of a nucleic acid reporter construct.

FIG. 2 is a schematic diagram of a multifunctional DSB reporter construct, from 5' on the left hand side to 3' on the right hand side. The text "Prom" denotes a promoter region, and the arrow shows the direction of transcription/translation. The promoter region may be a strong constitutive promoter, including but not limited to, a CAG promoter or a GDS promoter (also called TDH3 or GAPDH).

The promoter region drives expression of a 5' portion of an open reading frame for a first reporter gene (5'RP1). The 5'RP1 is a 5' portion of the first reporter gene. If the 5'RP1 is expressed as a truncated protein, the truncated protein is not capable of producing the intended signal of the full-length RP1.

A first microhomology domain (MHD) is 3' from the 5'RP1 (see FIG. 2, region marked by "μ" that is 3' of the 5'RP1). In some embodiments, the first MHD may be a part of the 5'RP1 itself. A second MHD is 3' of the first MHD, and has homology with the first MHD (see FIG. 2, region marked with "u"). If the cell having the reporter construct uses the MMEJ pathway to repair a double-stranded break created in the multifunctional DSB reporter construct, the homology of the first and second MHDs is used to repair the DSB.

Two or more double-stranded endonuclease recognition sequences (DSE-RS) are located between the first and second microhomology domains (see FIG. 2, black triangles). Each black triangle is a single DSE-RS. In the embodiment shown in FIG. 2, there are two DSE-RSs. When both of the DSE-RSs are recognized by a double-stranded cutting endonuclease, the double stranded nucleic acid between the two DSE-RSs is removed. In some embodiments, each of the DSE-RSs may be a different nucleic acid sequence and is cut by a different double-stranded endonuclease. The nucleic acids in between each of the first and second DSE-RSs may include one or more stop codons in-frame with the open reading frame of 5'RP1 (a termination cassette). In some embodiments, each of the two DSE-RSs is the same nucleic acid sequence, and is cut by the same double-stranded cutting endonuclease. In some embodiments, more than one pair of DSE-RSs may be included in the construct. For example a pair of DSC-RSs for I-SceI and a pair of DSE-RSs for AsiSI may each flank the intervening sequence. In such an embodiment, a single DSE may be chosen (e.g., either I-SceI, AsiSI, or an RNA-guided endonuclease with a guide RNA specific to a single pair of DSE-RSs) to cut and remove intervening sequence (e.g., a termination cassette), allowing a choice of which DSE-RS to target. In some embodiments, three, four, five, six, seven, eight, nine, ten, or more individual DSE-RSs may be used that are each recognized by a different double-stranded cutting endonuclease. In some embodiments, other types of sequences might replace or be added to the endonuclease sites in the current form of the reporter. For example, a fragile DNA sequence that is prone to spontaneous breakage during DNA replication might be added/substituted for. Likewise, a specific sequence that would allow docking of a protein that would promote stalling of the replication fork could be added/substituted for (Tus/Ter system, for instance).

The construct also contains a terminator cassette (two rows of letters on black background) that prevents any reporter genes from being expressed before a double-stranded break is created in the construct. The terminator cassette may include multiple transcriptional terminators that ensure termination of transcription before any full-length open reading frames can be transcribed as mRNA (such as tdTomato or iRFP670). Exemplary transcriptional terminators may include, but are not limited to, human actin beta (hACTB) terminator sequence, phosphoglucokinase (PGK) terminator sequence, simian virus 40 (SV40) terminator sequence, human growth hormone (hGH) terminator sequence, bovine growth hormone (bGH) terminator sequence, and rabbit beta-globin (rbGlob) terminator sequence. Forced expression of a DSE that recognizes the DSE-RSs in cells harboring this reporter construct will create a nucleic acid DSB in the reporter. This removes the termination cassette and results in two broken DNA ends. If the cell employs NHEJ to ligate the broken ends together, the IRES and RP2 are allowed to become part of the transcribed RNA, and only RP2 will be expressed, (see description of FIG. 3C below).

A 3' portion of an open reading frame for an allele of the first reporter gene (labeled 3'RP1 in FIG. 2) is located 3' to the second MHD (see, e.g., discussion of FIG. 3A below). If the 5'RP1 is in the same reading frame as the 3'RP1 following a DSB repair event (such as the MMEJ repair pathway), the resulting translated protein will have the signaling properties of the 3'RP1 allele (see FIG. 3E for example). The translated protein of the 5'RP1/MHD/3'RP1 is capable of producing a first signal, such as a fluorescence emission at a given wavelength or an enzymatic by-product if the translated 5'RP1/MHD/3'RP1 is an enzyme.

An internal ribosome entry site (labeled IRES in FIG. 2) is located 3' to the 3'RP1. The IRES allows cap-independent translation of an open reading frame for a second reporter gene that is located 3' from the IRES.

The second reporter gene (RP2) is operably linked to the IRES, and is capable of producing a second signal when translated. The second signal of RP2 is distinguishable from the first signal of a translated 5'RP1/3'RP1 protein. For example, the second signal of the RP2 may be a different wavelength of fluorescent emission from that of full-length RP1, or the second signal may be a catalytic by-product if the RP2 is an enzyme. Due to the IRES element, this reporter gene would be expressed even if the repair of the broken ends produced insertions or deletions that would cause unpredictable frameshifted repair products-provided that the IRES sequence remains intact after the repair event.

A second 5' portion of an open reading frame for a third reporter gene (RP3) is located 3' to the RP2. The RP3 has homology with portions of both the 5'RP1 and the 3'RP1, and is an allele of RP1. Cells that utilize the HR repair pathway to repair the double-stranded break in the construct homologously recombine the RP3 in a sister chromatid with the 5'RP1 and the 3'RP1, replacing the allelic portion of the 3'RP1. After this homologous recombination has taken place, the 5'RP1, the RP3, and the 3'RP1 (with a replaced allelic portion) form a functional RP3 protein. This functional RP3 protein is capable of producing a third signal that is distinguishable from both the first and second signals (see, e.g., FIG. 3D).

The construct shown in FIG. 2 also includes an open reading frame for a fourth reporter gene (labeled RP4 in FIG. 2). The RP4 encodes a full-length protein that produces a fourth signal when translated after an SSA repair event (see FIG. 3F). The fourth signal is distinguishable from each of the first, second, and third signals, such as a different wavelength of fluorescent emission, or a different catalytic by-product if the RP4 is an enzyme. In some embodiments, RP4 and RP3 may be separated by a linker nucleotide sequence that allows multicistronic expression of RP4 and RP3, if RP3 interferes with the reporting signal of RP4. The linker sequence may include, but is not limited to, an IRES, a cleavage site of a protease (e.g., 3C or "PreScission"; enterokinase (EKT); Factor Xa (Fxa); Tobacco etch virus (TEV); or thrombin), or a ribosomal skipping peptide (such as T2A, P2A, E2A, or F2A).

The DSB reporter may further comprise reporter genes such as, but not limited to RP5, RP5 and RP6, or RP5, RP6, and RP7. In some embodiments, additional or distinct repair homologous templates are added to the reporter construct along with additional reporter genes, thereby allowing expansion of the repertoire of DSB repair pathway choices that can be assayed with this system. In some embodiments RP5, RP6, and RP7 correspond to repair products of pathways other than HR, NHEJ, MMEJ, and SSA. These repair pathways can be any repair pathways known in the art or later discovered.

Reference will now be made to specific examples illustrating the disclosure. It is to be understood that the examples are provided to illustrate exemplary embodiments and that no limitation to the scope of the disclosure is intended thereby.

Example 1: Multifunctional DSB Reporter Construct with Fluorescent Reporter Genes An exemplary DSB reporter construct that uses fluorescent reporter genes is described in this example. The features of this exemplary cellular DSB repair choice detection system include: a strong mammalian promoter to drive expression of the fluorescent reporter genes (a CAG promoter); two tandem repeats of partial EGFP/BFP coding sequences that act as repair templates for the HR, MMEJ and SSA repair pathways; an intact coding sequence for tdTomato as a fluorescent reporter for NHEJ; and the coding sequence for iRFP670, which acts as a reporter for SSA repair.

The construct also contains a terminator cassette that prevents any reporter genes from being expressed before a double-stranded break is created in the construct. The terminator cassette may include one or more stop codons and/or one or more transcriptional polyadenylation sequences (four SV40-poly A sequences) that ensure termination of transcription before any full-length open reading frames can be transcribed (such as tdTomato or iRFP670). The reporter construct also includes microhomology regions adjacent to the DSE-RSs for rare-cutting restriction enzymes (AsiSI, I-SceI). Forced expression of either AsiSI or I-SceI enzyme in cells harboring this reporter construct will create a nucleic acid DSB in the reporter. This results in excision of the terminator cassette, forming two broken DNA ends. If the cell employs NHEJ to ligate the broken ends, the flanking GFP-encoding sequences will not be sufficient for encoding a functional GFP. However, since an IRES is allowed to become part of the transcribed RNA (via removal of the termination cassette), only tdTomato will be expressed, which fluoresces orange (see description of FIG. 3C below).

Alternatively, one of the recombination-based repair pathways (HR, MMEJ or SSA) can drive the repair of the broken ends of the DSB. In that case, one of the three repair different templates provided by the DSB reporter construct will be utilized depending on the pathway that is chosen. If the cell uses HR to repair the DSB, then the homologous recombination of the partial EGFP sequence results in expression of a functional EGFP protein and tdTomato, which have distinguishable fluorescent emissions (see discussion of FIG. 3D below). If the cell uses MMEJ and the two microhomology domains to repair the DSB, then the partial EGFP sequence and the partial EBFP sequence (an allele of EGFP) together allow expression of a fluorescent protein that emits light at a blue wavelength, along with expression of tdTomato (see discussion of FIG. 3E below). If the cell uses the SSA pathway to repair the DSB, the homology of the partial EGFP sequence and its associated promoter result in excision of the tdTomato sequence and expression of iRFP670 as the sole functional fluorescent protein, resulting in only a maroon fluorescence from the iRFP670 being detectable (see discussion of FIG. 3F below).

In one embodiment, the fluorescent DSB reporter construct is integrated into a cellular genome. Following forced expression of one or both of the rare-cutting endonucleases in a cell results in a double-stranded cut in the reporter construct and expression of one or more of the fluorescent reporter genes, depending on the repair pathway utilized. Thus, counting how many cells are expressing each one of these different fluorescent proteins by FACS will reflect the relative frequency in which a particular repair pathway is chosen to promote one single event of DSB repair in a cell's genome.

Figure 3A:
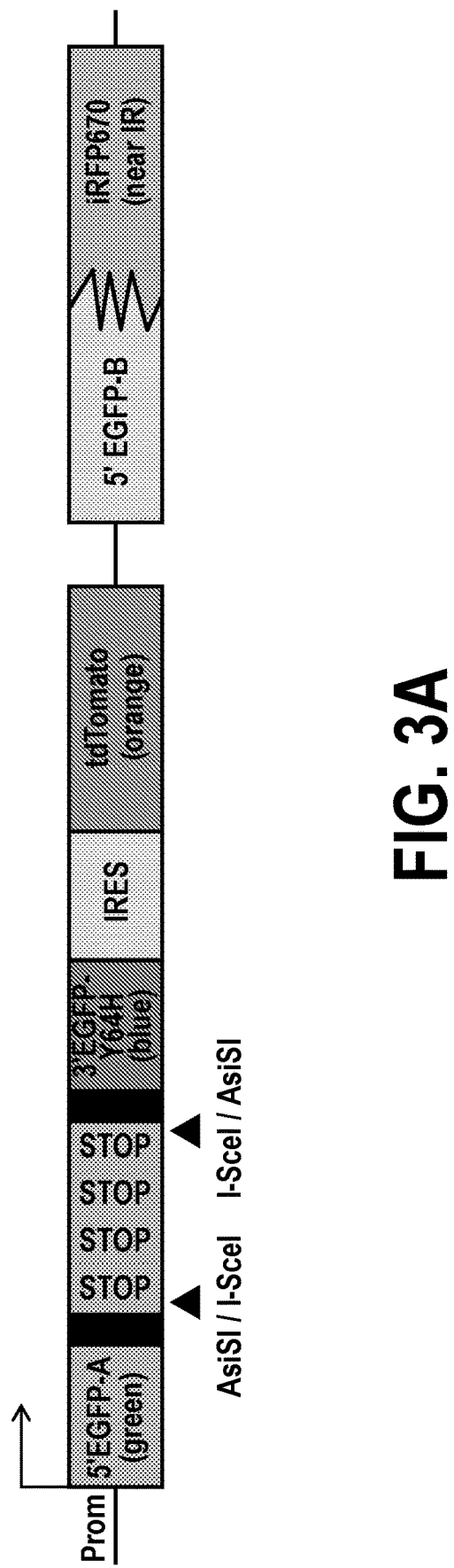
FIG. 3A is a schematic diagram of a nucleic acid reporter construct using fluorescent reporter proteins.

FIG. 3A is a schematic diagram of an exemplary fluorescent DSB reporter construct, from 5' on the left hand side to 3' on the right hand side. The text "Prom" denotes a promoter region (a CAG promoter), and the arrow shows the direction of transcription/translation. The promoter drives expression of a 5' portion of an open reading frame for enhanced green fluorescent protein (labeled 5'EGFP-A).

A first microhomology domain (MHD) is 3' from the 5'EGFP-A (see FIG. 3A, region marked by "µ" that is 3' of the 5'EGFP-A). In the embodiment shown, the first MHD sequence is part of the 5'EGFP-A. Thus, the sequence of the 5'EGFP-A includes the first MHD and ends at the termination cassette (discussed below). A second MHD is 3' of the first MHD (see FIG. 3A, region marked with "u" that is 3' of the first MHD), and has homology with the first MHD.

A termination cassette (see FIG. 3A, black box with two rows of letters) is located between the first and second MHD to ensure that transcription of the 5'EGFP-A does not continue beyond the cassette. The termination cassette includes multiple polyadenylation signal sequences, including four SV40-polyA sequences.

Each of the black triangles each indicate pairs of double-stranded cutting recognition domains (DSE-RS) that are near each other. In each pair of DSE-RSs, one DSE-RS is recognized by AsiSI, and the other DSE-RS is recognized by I-SceI. Although a pair of DSE-RSs is used, only a single restriction enzyme is needed to create two double-stranded cuts and remove the termination cassette (see FIG. 3B). Having different DSE-RSs provides flexibility in using restriction enzymes to make the double-stranded break. In some embodiments, only a single DSE-RS (for example an AsiSI recognition domain) may be included on each side of the termination cassette. In some embodiments, more than two DSE-RSs may be included on each side of the termination cassette (e.g., AsiSI domain, I-SceI domain, and a unique sequence that can be recognized by an RNA-guided endonuclease with a guide RNA).

A 3' portion of an open reading frame for an allele of EGFP (labeled 3'EGFP-Y64H in FIG. 3A) is located 3' to the second MHD. If the 5'EGFP-A is in the same reading frame as the 3'EGFP-Y64H following an MMEJ pathway repair event, the resulting translated protein will have the signaling properties of blue fluorescent protein (BFP) (see discussion of FIG. 3E below).

An internal ribosome entry site (labeled IRES in FIG. 3A) is located 3' to the 3'EGFP-Y64H. The IRES allows cap-independent translation of an open reading frame for a tdTomato gene sequence located 3' from the IRES. The tdTomato sequence is operably linked to the IRES, and when expressed produces an orange fluorescent signal. The tdTomato gene is expressed in response to an NHEJ, HR, or MMEJ repair event following creation of the double-stranded break by forced expression of AsiSI and/or I-SceI and removal of the termination cassette (see discussion of FIGS. 3C-3E below).

A second 5'portion of an open reading frame for EGFP (5'EGFP-B) is located 3'to the tdTomato sequence. The 5'EGFP-B has homology with portions of both the 5'EGFP-A and the 3'EGFP-Y64H. Cells that utilize the HR repair pathway to repair the double-stranded break in the construct homologously recombine the 5'RP1-B in a sister chromatid with the 5'EGFP-A and the 3'EGFP-Y64H, replacing the allelic portion of the 3'EGFP-Y64H. After this homologous recombination has taken place, the 5'RP1-A, the newly recombined gene sequence forms a functional EGFP protein (see discussion of FIG. 3D below).

An open reading frame for the gene sequence of iRFP670 (labeled iRFP670 in FIG. 3A). The iRFP670 encodes a full-length protein that fluoresces maroon when translated after an SSA repair event (see discussion of FIG. 3F). A linker nucleotide sequence is located between the 5'EGFP-B sequence and the iRFP670 sequence. The linker sequence comprises nucleotide sequence encoding peptide P2A, which causes ribosomal skipping during translation of the 5'EGFP-B and the iRFP670 from the same mRNA following an SSA event. This allows iRFP670 to be expressed without the 5'EGFP-B peptide fragment quenching or otherwise affecting its fluorescence. In some embodiments, other linker nucleotide sequences may be used, such as another 2A peptide encoding sequence, an encoded protease cleavage site, or an IRES.

Figure 3B:
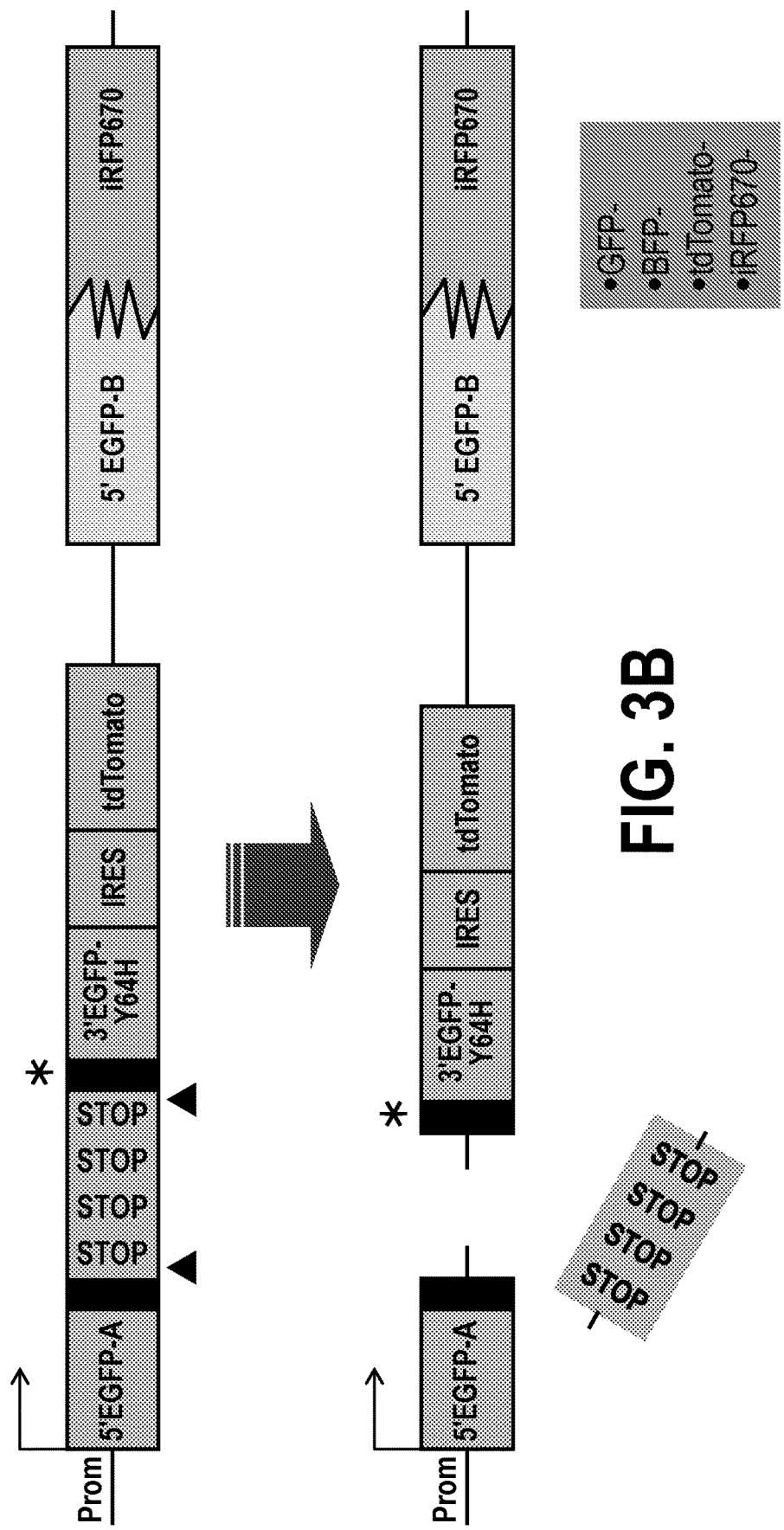
FIG. 3B is a schematic diagram of the nucleic acid reporter construct of FIG. 3A before and after contact with a rare-cutting endonuclease or an RNA-guided DNA endonuclease.

FIG. 3B is a schematic diagram of the fluorescent DSB construct before (top construct) and after exposure to AsiSI or I-SceI (bottom construct). A double stranded break is created, removing the termination cassette. The cell harboring the construct can now utilize its preferred DSB repair pathway to mend these broken DNA ends.

Figure 3C:
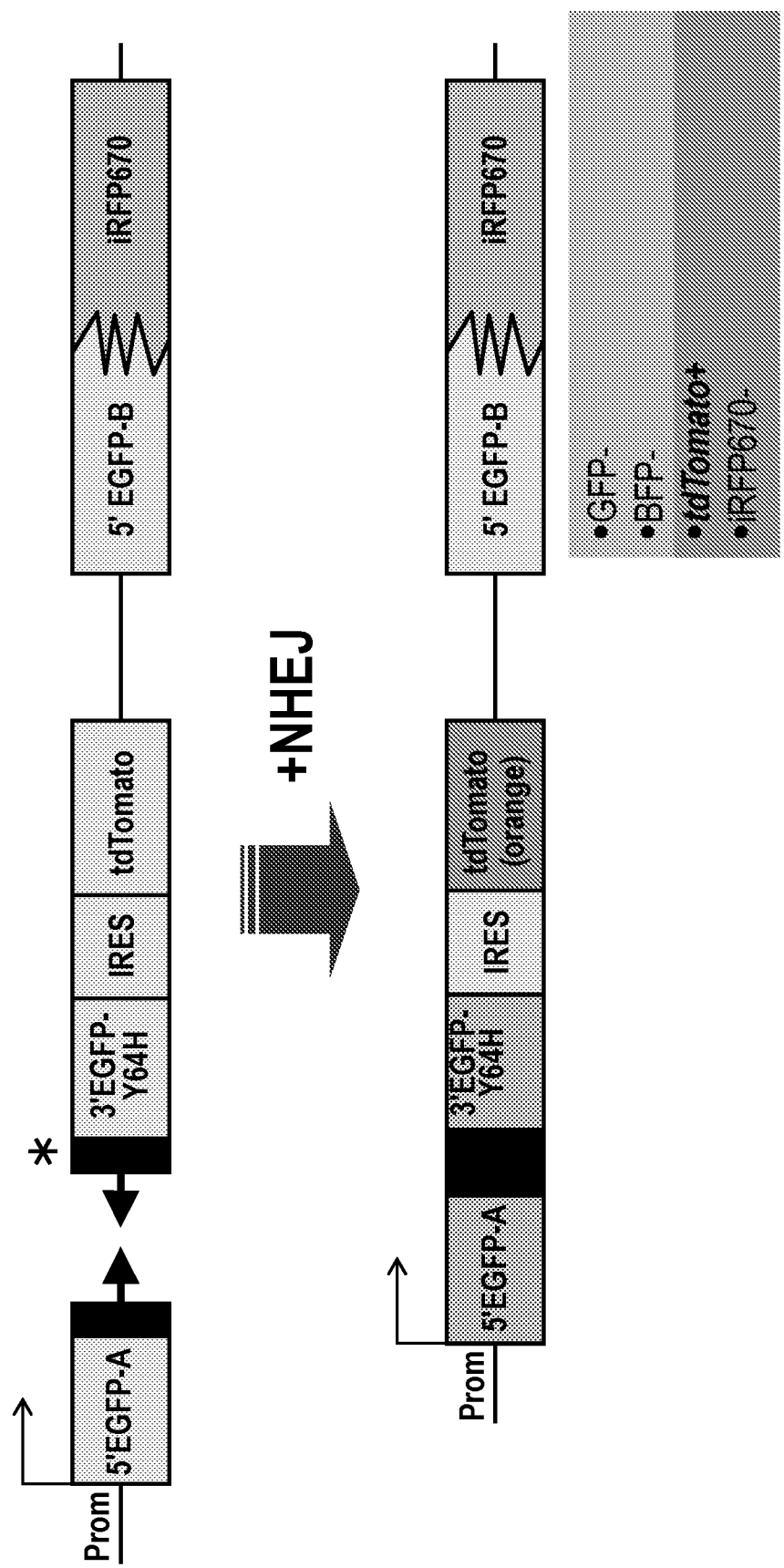
FIG. 3C is a schematic diagram of the cleaved nucleic acid reporter construct of FIG. 3B before and after repair by the NHEJ repair pathway.

FIG. 3C is a schematic diagram of the NHEJ repair pathway being used to repair the fluorescent DSB construct. During NHEJ, the ends of the double-stranded break are ligated together directly (see arrows on ends of the microhomology domains on the top construct). Following this removal of the termination cassette and direct ligation, the transcribed RNA is no long terminated before transcription of the IRES, and tdTomato protein is expressed. None of the other reporters are expressed at full-length and/or in-frame, and therefore cannot be detected by fluorescence.

Figure 3D:
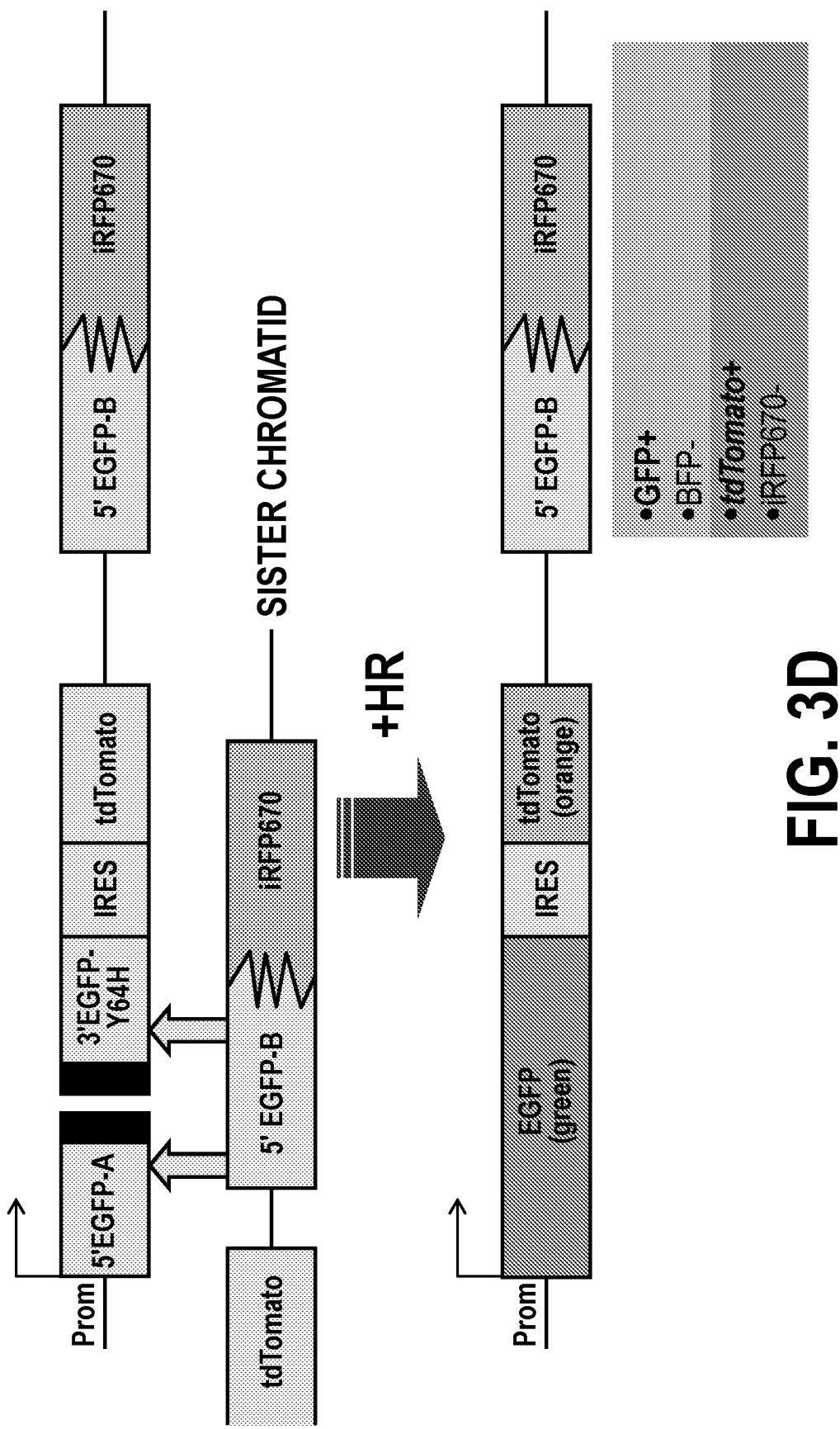
FIG. 3D is a schematic diagram of the cleaved nucleic acid reporter construct of FIG. 3B before and after repair by the HR repair pathway.

FIG. 3D is a schematic diagram of the HR repair pathway being used to repair the fluorescent DSB construct. After the DSB has been made in the construct, the 5'EGFP-B portion of the construct from a sister chromatid is used to repair the break. The 5'EGFP-B has homology to both the 5'EGFP-A and the 3'EGFP-Y64H (see gray arrows indicating homologous regions). When the HR repair process is complete, the repaired sequence is that of a full-length EGFP. Both full-length EGFP (green fluorescence) and tdTomato (orange fluorescence) are expressed.

Figure 3E:
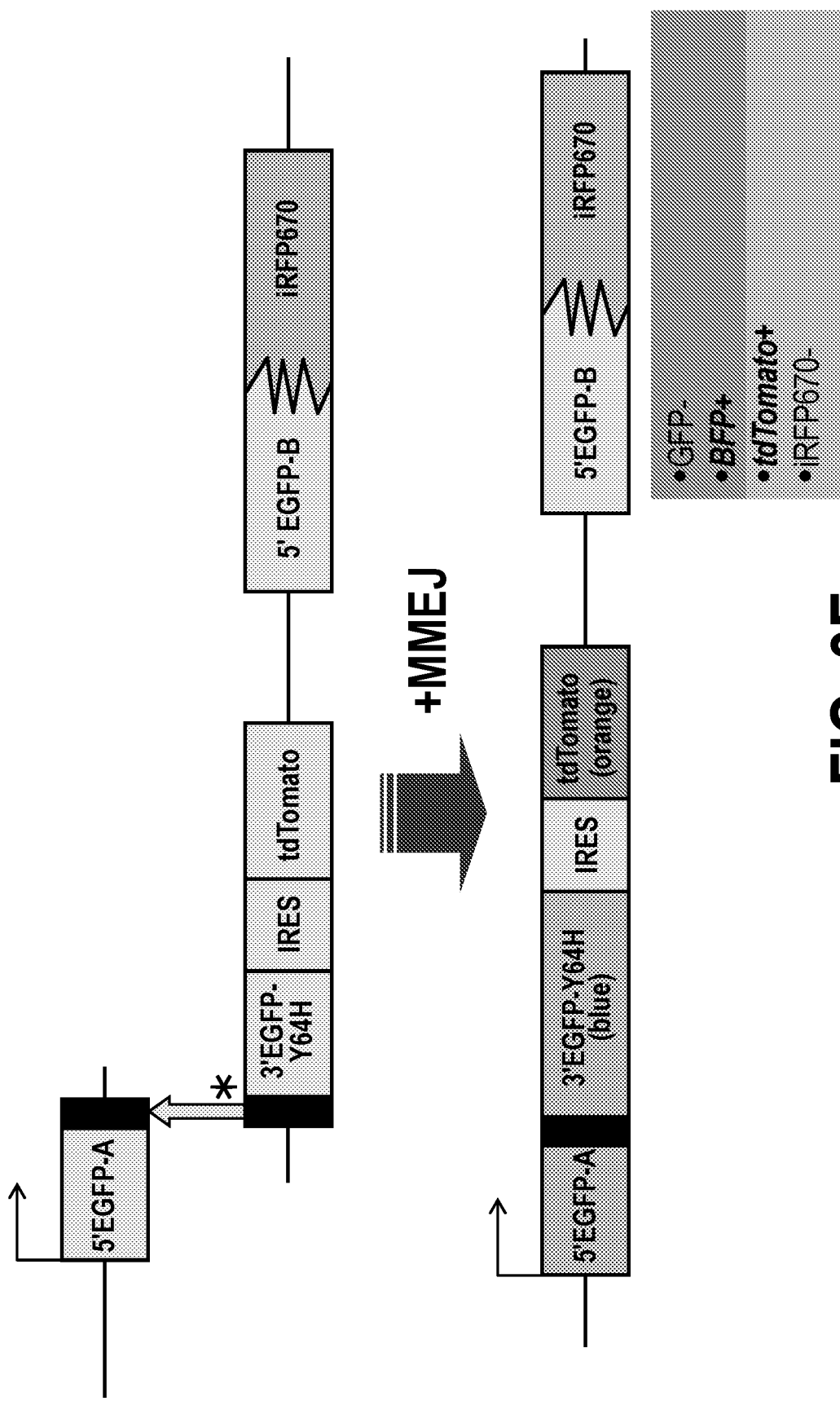
FIG. 3E is a schematic diagram of the cleaved nucleic acid reporter construct of FIG. 3B before and after repair by the MMEJ repair pathway.

FIG. 3E is a schematic diagram of the MMEJ repair pathway being used to repair the fluorescent DSB construct.

During the MMEJ repair process, the microhomology domains (labeled "u") on each end of the broken chromatid recombine (see gray arrow between the MHD on each end of the break) and the ends of the break are ligated together, leaving a single microhomology domain. This leaves the 5'EGFP-A in the same reading frame as the 3'EGFP-Y64H, allowing expression of a full-length EGFP-Y64H protein and a full-length tdTomato protein. The full-length EGFP-Y64H fluoresces blue, and the tdTomato fluoresces orange.

Figure 3F:
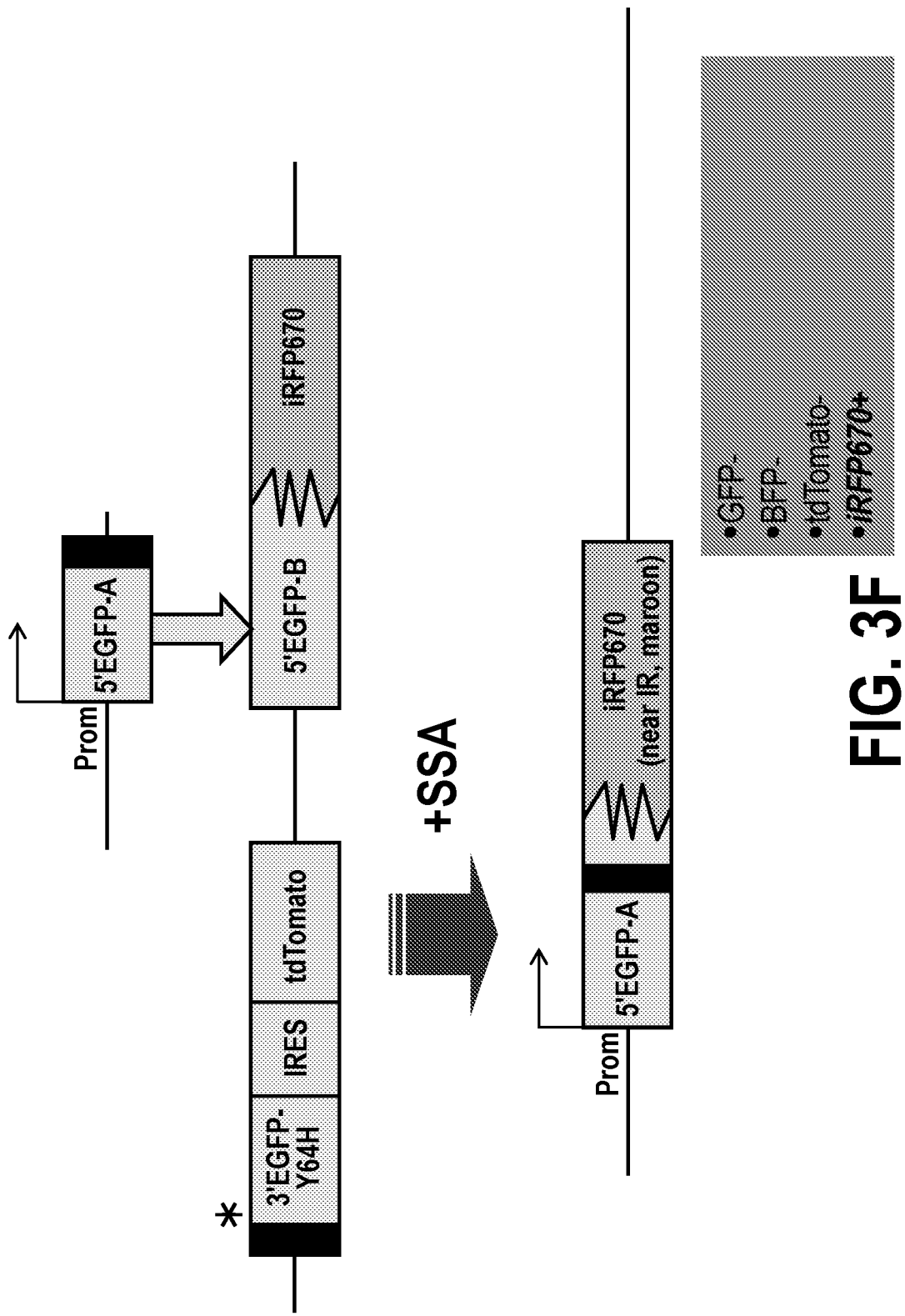
FIG. 3F is a schematic diagram of the cleaved nucleic acid reporter construct of FIG. 3B before and after repair by the SSA repair pathway.

FIG. 3F is a schematic diagram of the SSA repair pathway being used to repair the fluorescent DSB construct. The 5'EGFP-A is annealed with homologous sequence of 5'EGFP-B on the same chromatid. The promoter associated with the 5'EGFP-A drives expression of the iRFP670 protein, which fluoresces maroon. The section of chromatid containing the 3'EGFP-Y64H, the IRES, and the tdTomato is deleted; thus no other fluorescent proteins are retained in the repaired construct.

FIG. 3G is a schematic diagram that summarizes which fluorescent proteins are expressed by the fluorescent DSB construct after each repair pathway. Uncut fluorescent DSB construct does not express any fluorescent proteins and thus no fluorescent colors. Cut fluorescent DSB construct that has been repaired via the NHEJ pathway expresses only tdTomato protein, and thus fluoresces orange when excited at around 554 nm. Cut fluorescent DSB construct that has been repaired via the HR pathway expresses both EGFP (fluorescing green when excited at around the maximal excitation wavelength of 488 nm) and tdTomato (fluorescing orange when excited at around the maximal excitation wavelength of 554 nm). Cut fluorescent DSB construct that has been repaired via the MMEJ pathway expresses BFP (EGFP-Y64H; fluorescing blue when excited at around the maximal excitation wavelength of 383 nm) and tdTomato (fluorescing orange when excited at around the maximal excitation wavelength of 554 nm). Cut fluorescent DSB construct that has been repaired via the SSA pathway expresses only iRFP670, which fluoresces maroon when excited at around the maximal excitation wavelength of 670 nm.

Example 2-DSBR Repair Pathway Choice Assay Using Transient Transfection

Equal amounts of the fluorescent DSB reporter construct (FluoMulti) described in Example 1 were transfected as uncut, in vitro-cut, or co-transfected with Cas9+sgRNA dual expression vectors and their respective non-target controls. Naïve 293T cells were transfected using LIPOFECTAMINE 2000 (Thermo Fisher Scientific) following the manufacturer's instructions. Briefly, for each transfection, one subconfluent (70-80%) P100 plate of asynchronous cultures of 293T cells was trypsinized and transfected in suspension with a total 25 µg of plasmid DNA and using 60 µL of Lipofectamine 2000 reagent. The DNA being transfected consisted of a mixture of 5 µg of the FluoMulti plasmid (digested in vitro with I-SceI or undigested, depending on the condition tested) and 20 µg of either non-similar plasmid (pUC18, Addgene #50004), I-SceI-encoding plasmid (pCB-ASCe, Addgene #26477), or Cas9+sgRNA expression vectors (LentiCrisprV2, Addgene #52961) in which the sgRNA expressed directs Cas9 to cleave within the I-SceI sites of FluoMulti. Empty vector controls for I-SceI or Cas9+sgRNA (20 µg) were also co-transfected with 5 µg of FluoMulti, when appropriate. The cells were cultivated in 5% $CO_2$, humidity-saturated incubators at 37° C. Seventy-two hours post-transfection, the cells were harvested by trypsinization, fixed with buffered paraformaldehyde and analyzed in a FORTESSA flow cytometer (BD Biosciences) equipped with violet, blue, yellow-green and red lasers (405, 488, 561 and 641 nm excitation wavelengths, respectively). The DNA coding sequences for the sgRNAs include

```
                                    (SEQ ID NO: 8; CrPD)
            GTAGGGATAACAGGGTAATATGG, (SEQ ID NO: 9; Cr1A)
            TAACGAATAAAAGTTACGCTAGG, (SEQ ID NO: 10; Cr1B)
            AACGAATAAAAGTTACGCTAGGG, (SEQ ID NO: 11; Cr1C)
            AAGTTACGCTAGGGATAACAGGG,
            and (SEQ ID NO: 12; Cr1D)
            AAAGTTACGCTAGGGATAACAGG.
```

Figure 4:
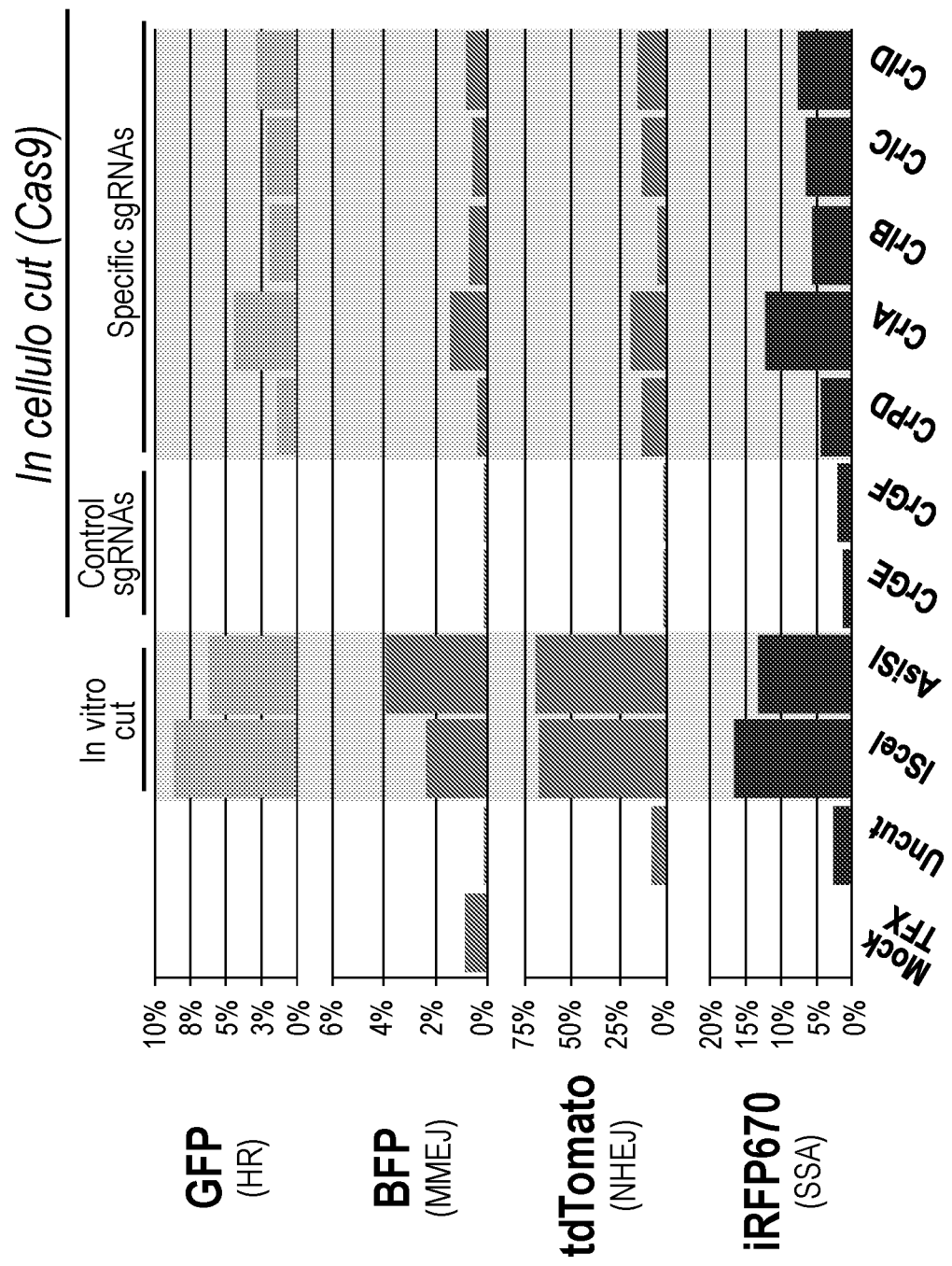
FIG. 4 is a set of histograms depicting detection of four different fluorescent reporter proteins in 293T cells transiently transfected with a nucleic acid reporter construct. The reporter construct was either cut in vitro with the endonuclease I-SceI and then transfected into the 293T cells, or the cells were co-transfected with Cas9+sgRNA dual expression vectors specific for the I-SceI cutting recognition sequence.

Transfection of in vitro-cut reporter DNA leads to a clear surge in fluorescence-positive cells of all colors, reflecting use of all repair pathways (see bar charts of FIG. 4). Likewise, there is a noticeable increase in fluorescent protein expression for EGFP, BFP (EGFP-Y64H), tdTomato, and iRFP670 when on-target Cas9+sgRNA vectors were used, but not with the non-similar pUC18 plasmid nor with off-target Cas9+sgRNA combinations were used.

Example 3-DSBR Repair Pathway Choice Assay Using Stably Transfected Cell Clones

In order to obtain cell clones in which one copy of FluoMulti was integrated in the cells' genome, electroporation was used to deliver the relevant plasmid. For that purpose, 293T cells (around $10^7$ cells) were electroporated with 30 µg of supercoiled FluoMulti plasmid in a final volume of 400 µL of OPTI-MEM medium (Thermo Fisher Scientific), at room temperature. GENEPULSER II equipment (Bio-Rad) was used to deliver an electric pulse of 300V with 950 µF of capacitance. Cells were plated with fresh medium (DMEM+10% FBS+2 mM Glutamine) immediately after the pulse. Selection with 250 µg/mL of Hygromycin B was started around 48 h post electroporation. When cell colonies became visible (15-20 days), cells were isolated using cloning discs and transferred to multi-well tissue culture plates and the antibiotic selection was switched to blasticidin at 10 g/mL. The antibiotic-resistant, clonal populations that resulted after blasticidin selection were used for generation of cells stocks and further analyses. The serial selection with these two antibiotics favored the selection of clonal cell lines in which the intact reporter was stably integrated in the cells' genome.

The cell clones isolated as above were initially screened for their ability to generate fluorescent repair products following in cellulo cleavage of the reporter following forced overexpression of I-SceI. For that purpose, cells were infected with an inducible lentiviral vector that drives overexpression of I-SceI in response to doxycycline along with puromycin resistance, or its corresponding empty vector. After selection of the stably infected cells with puromycin at 4 µg/mL for 48 h, cells were split 1:2 in multi-well plates, so that for each condition there are cells treated with either 1 µM doxycycline or with the same volume of phosphate buffered saline (PBS) as a vehicle control. Approximately 72 hours post-addition of doxycycline, cells were fixed and analyzed as described in Example 2. Clones that displayed the ability to execute DSBR repair by all 4 pathways (albeit at different proportions) were chosen for further analysis. FIGS. 5A-5D show bar graphs for the percentage of fluorescent marker detected by FACS for each clone transfected with either I-SceI expression vector or its corresponding empty vector control. These independent clones have one or more copies of the FluoMulti reporter randomly integrated in their genome. While all five clones noticeably report performance of HR and NHEJ, only clones P19, P20, and P22 report performance of MMEJ in response to IsceI-mediated cleavage, and only clones P15 and P20 report performance of SSA. This heterogeneity of repair capacity is expected, given that the isolated clones have randomly integrated the FluoMulti reporter in their genome. Despite the small fold-induction values observed for MMEJ (clones P19, P20, and P22) and SSA (clones P15 and P20), these signals represent authentic formation of the expected repair products, as judged by independent confirmation both by regular PCR on genomic DNA as well as by quantitative RT-PCR (data not shown).

Figures 6A, 6B:
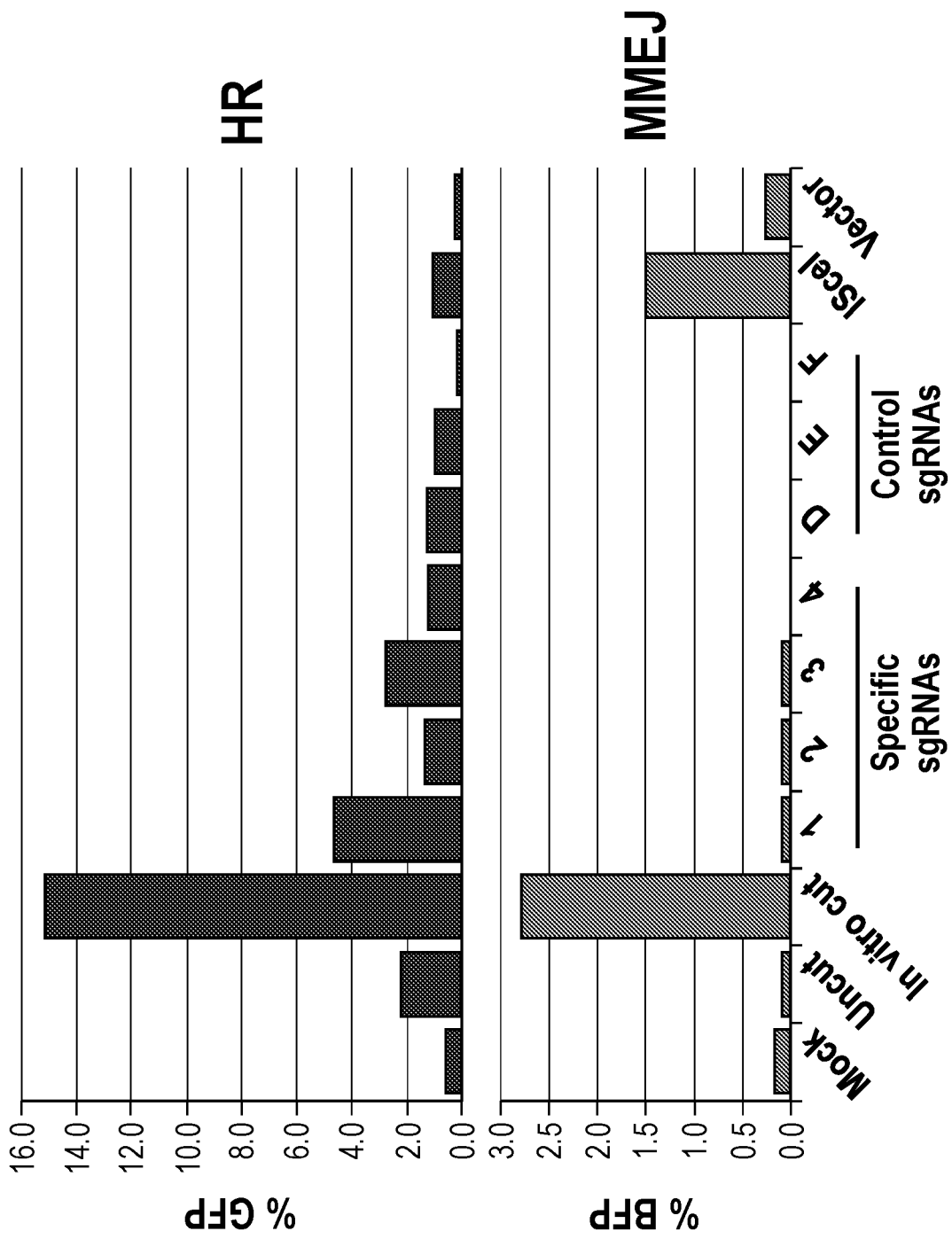
FIGS. 6A-B are a histogram showing the percentage of GFP (FIG. 6A) or BFP-positive (FIG. 6B) cells detected in 293T cell clones stably transfected with a nucleic acid reporter construct, following transient transfection with either an endonuclease I-SceI encoding vector or a CRISPR vector encoding both Cas9 and the relevant sgRNA (single guide RNA).

FIGS. 6A-B show bar graphs representing the percentage of fluorescent marker detected by FACS of 293T cells transfected with a CRISPR encoding vector or a I-SceI encoding vector. A transient transfection of the FluoMulti reporter into naïve cells was completed. 293T cells were plated at 80% confluency in 6-well plates and the transfection was performed with the cells still in suspension using Lipofectamine 2000 (ThermoFisher). 5 μg of naked plasmid DNA was used per transfection (well/condition). For Cas9/sgRNA conditions, 4 μg of the relevant CRISPR vector encoding both Cas9 and the relevant sgRNA were transfected along with 1 μg of the reporter plasmid.

Similarly, either 4 μg of ISceI-encoding vector (or the corresponding empty vector) were transiently transfected with 1 μg of reporter plasmid. The controls included in vitro-cut and uncut vector only. 72 hours later, the cells were fixed and analyzed for fluorescence by FACS. FIG. 6A shows the percentage of GFP-positive cells. FIG. 6B shows the percentage of BFP-positive cells.

Transfection of in vitro-cut reporter DNA leads to a clear surge in fluorescence-positive cells of both colors, reflecting use of both repair pathways. The extent of repair detected with the in vitro-cut reporter is higher than in cellulo-cut conditions, because the cleavage efficiency is nearly 100% in the former and relatively low in the latter. These experiments demonstrate that either I-SceI initiated DSBs or CRISPR initiated DSBs lead to DNA repair events that are detectable with the FluoMulti reporter system.

Example 4-Multifunctional DSB Reporter Construct with Fluorescent Reporter Genes and Csy4 for Reducing Background Fluorescence Detection of the Fluorescence Background:

In order to determine if reporter protein fluorescent signal was detectable in the absence of the initiation of DNA repair, the fluorescent signal of each of the reporter proteins was analyzed in control samples of cells untreated with I-SceI endonuclease. Fluorescent signal in the absence of I-SceI endonuclease to initiate DNA repair is representative of background signal that occurs in the absence of DNA repair mechanisms altering the structure of the DSB reporter.

Figure 7A:
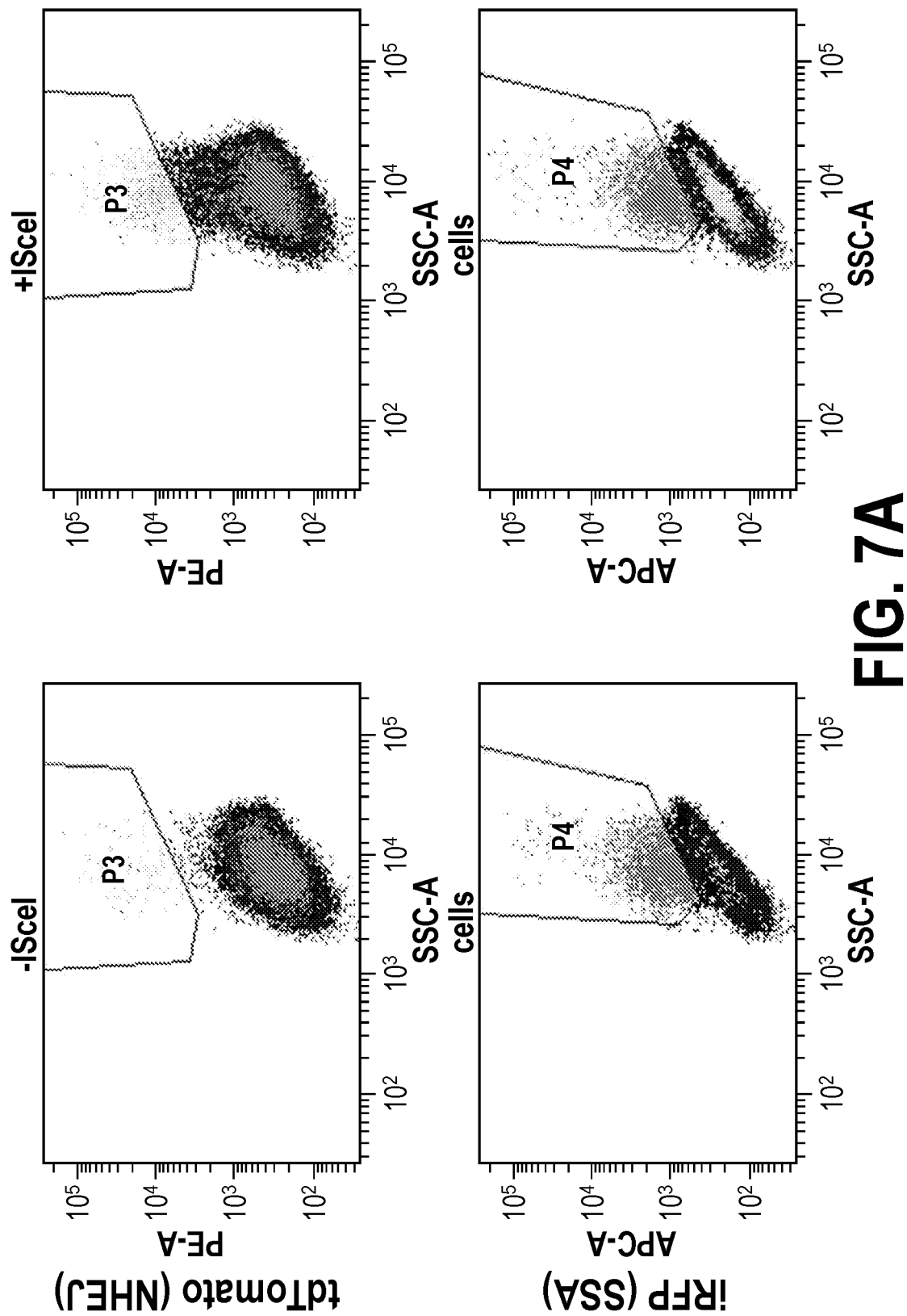
FIG. 7A depicts the fluorescent signal from tdTomato and iRFP in 293T cell clone P19 with and without repair triggered by I-SceI cleavage. The comparison illustrates the fluorescent signal background problem in the absence of DNA repair.
Figure 7B:
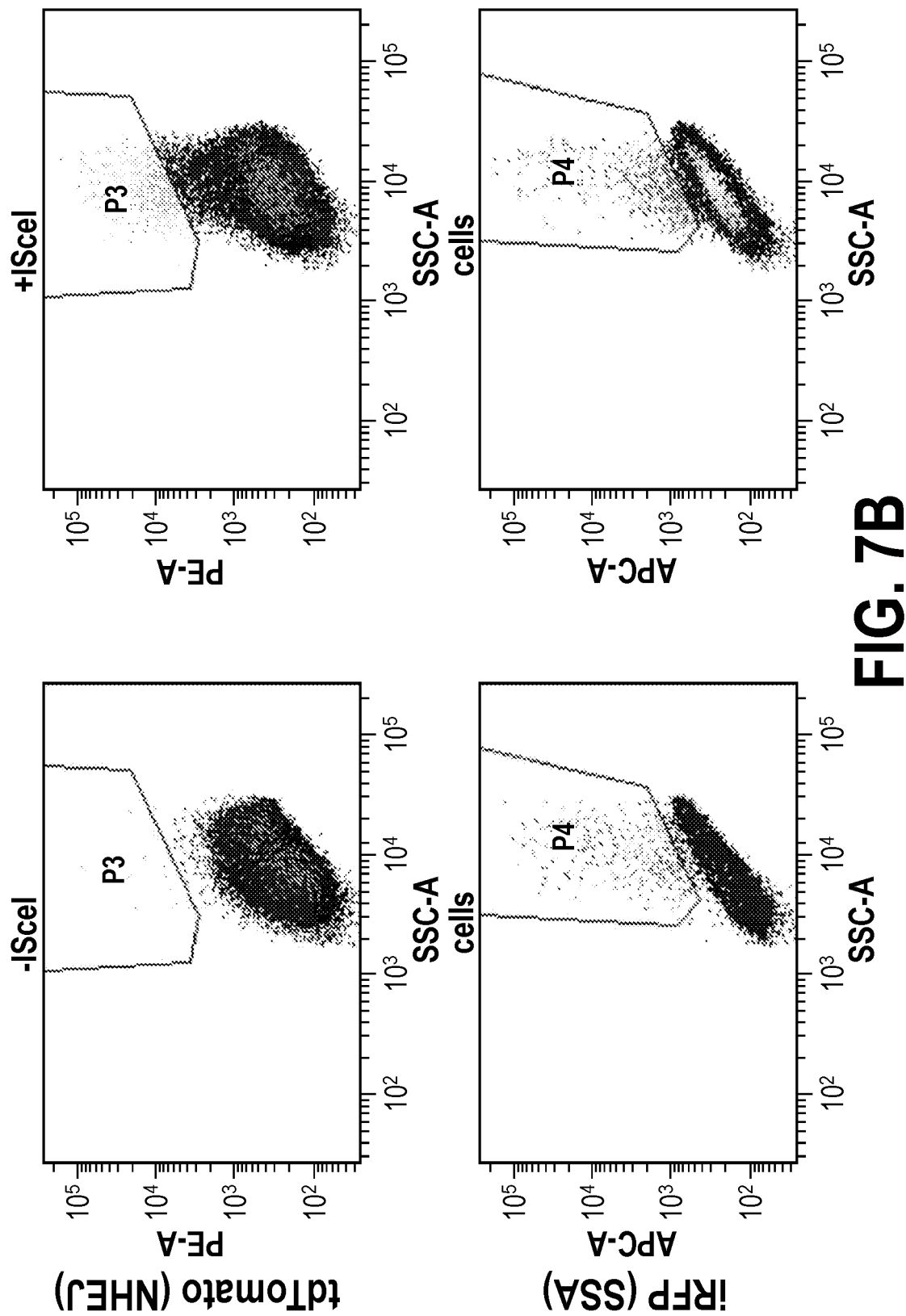
FIG. 7B depicts the fluorescent signal from tdTomato and iRFP in 293T cell clone P22 with and without repair triggered by I-SceI cleavage. The comparison illustrates the fluorescent signal background in the absence of DNA repair.

FIGS. 7A and 7B show detection of tdTomato (representative of NHEJ repair) and iRFP (representative of SSA repair) fluorescent signal in 293T cells that are either treated with I-SceI endonuclease (initiating DNA repair) or untreated control cells. FIG. 7A presents results from 293T cell clone P19, while FIG. 7B presents results from 293T cell clone P22. In both cell clones, one copy of the FluoMulti reporter was integrated at a random location within the genome of the cell. As shown in FIGS. 7A and 7B, 293T untreated control cells in which the FluoMulti reporter was uncut and unrepaired displayed significant background signal of tdTomato and iRFP.

Figure 8A:
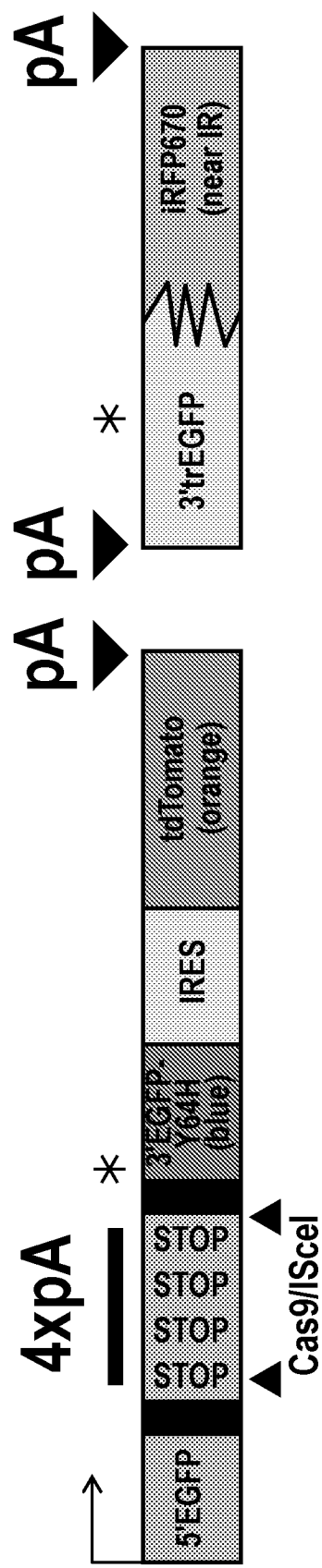
FIG. 8A is a schematic diagram of the nucleic acid reporter construct of FIG. 2 with polyadenylation signals included as transcriptional stop elements.
Figure 8B:
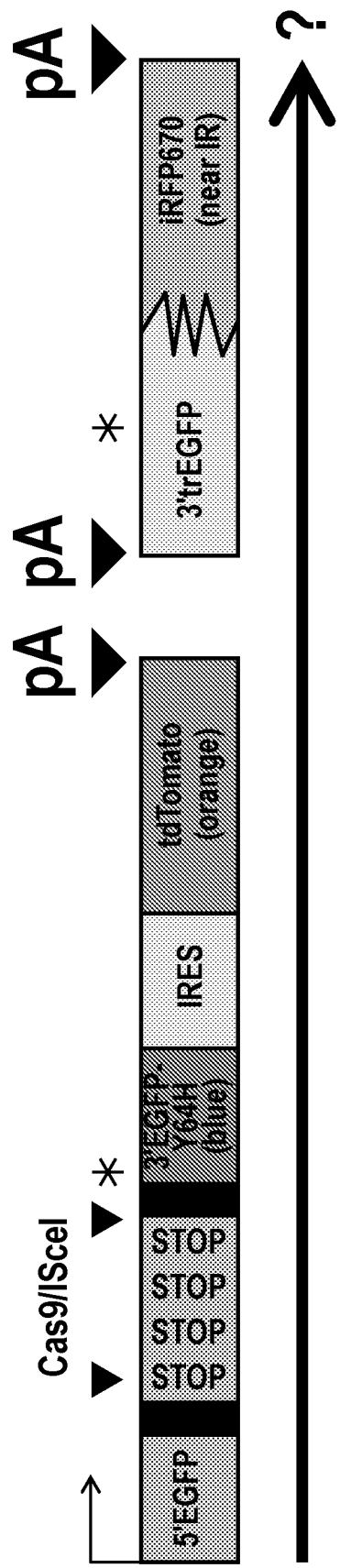
FIG. 8B is a schematic diagram of the nucleic acid reporter construct of FIG. 2 and a model of run-through transcription occurring in the absence of endonuclease induced DNA repair.

Unlike EGFP and GFP, the design of the FluoMulti reporter is such that the coding region of the tdTomato and iRFP reporter protein sequences is intact in the vector. Transcriptional stop elements 5' to the tdTomato and iRFP reporter protein sequences were meant to block expression of these fluorescent proteins in the absence of repair. The background signal shown in FIGS. 7A and 7B demonstrate that these transcriptional stop elements alone are not sufficient to block the expression of tdTomato and iRFP fluorescent proteins. FIG. 8B shows a likely mechanism for expression of the fluorescent reporters in the absence of repair. The mechanism is run-through transcription driven by the promoters contained with the FluoMulti reporter.

DSB Reporter Construct with Csy4 to Reduce Background Fluorescence

Figure 10A:
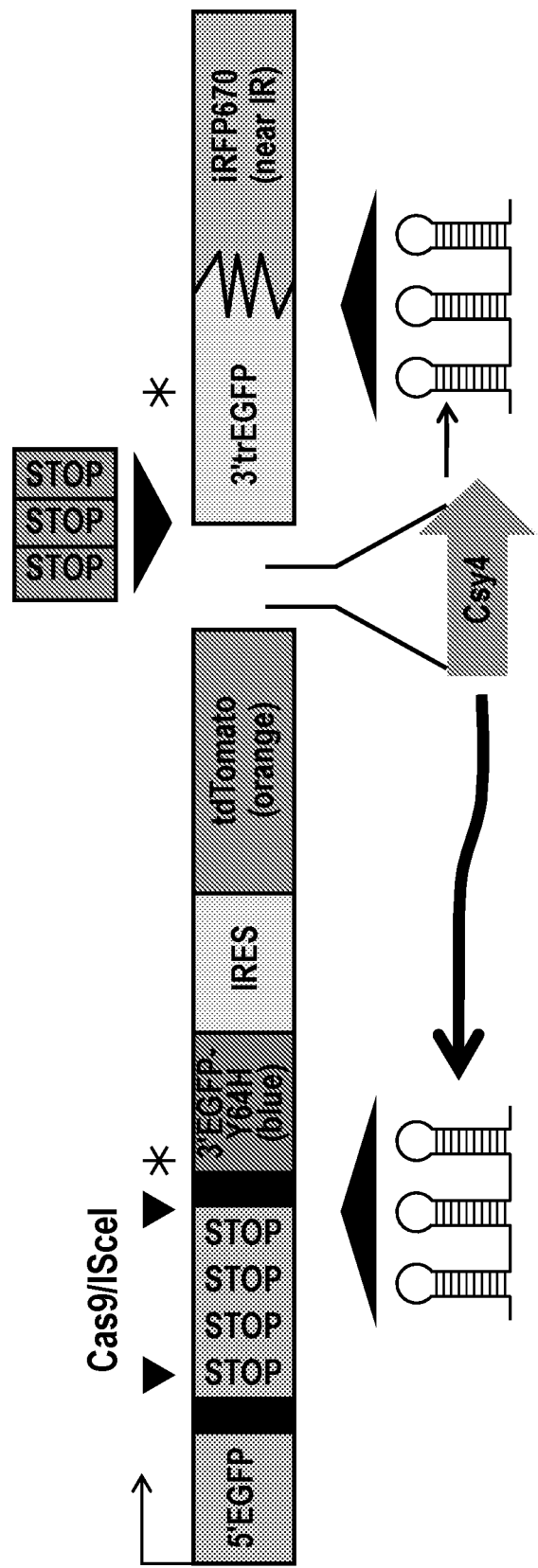
FIG. 10A is a schematic diagram of the nucleic acid reporter construct of FIG. 2 with the addition of a Csy4 expression cassette. A triple hairpin sequence has been added to both the tdTomato polycistronic transcript, as well as, to the polycistronic iRFP transcript.

In order to improve run-through transcription, in some embodiments the DSB reporter construct incorporates a ribonuclease mechanism to destroy mRNA transcripts that result from run-through transcription in the absence of DNA repair. This new reporter is called the FluoMultiCsy4 reporter and shown in FIG. 10A. The ribonuclease used was CRISPR-associated protein Csy4. Csy4 is continually expressed from an expression cassette contained within the FluoMultiCsy4 reporter.

Figure 9A:
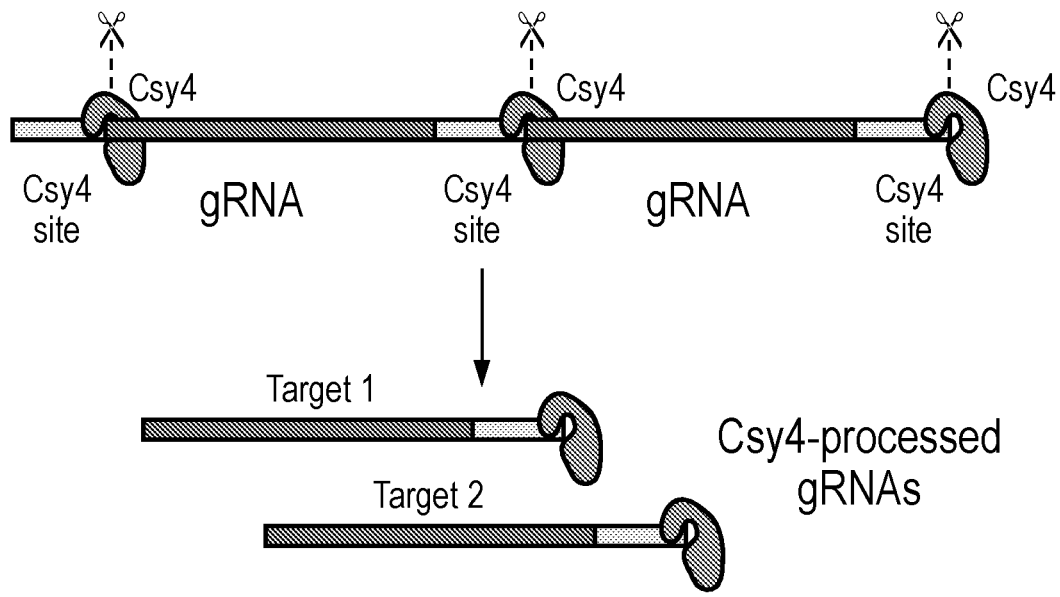
FIG. 9A is a schematic diagram of the mechanism of Csy4 cleavage of guide RNAs (gRNAs).
Figure 9B:
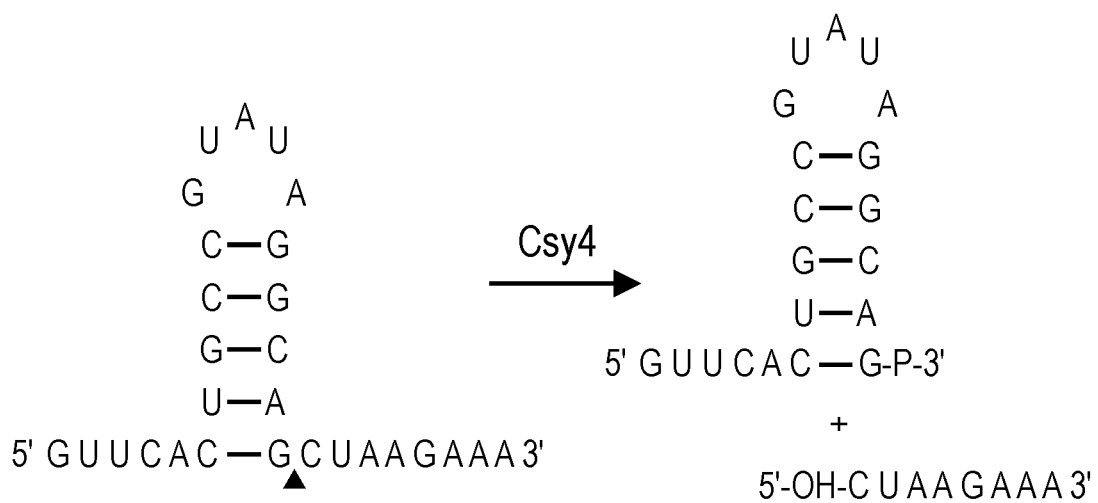
FIG. 9B is a schematic diagram of Csy4 recognition of a hairpin comprising SEQ ID NO: 13 and of Csy4 cleavage of a hairpin into two nucleic acids, one of which comprises SEQ ID NO: 14.

As shown in FIG. 9A, Csy4 can be directed to cleave a specific RNA sequence through the use of guide RNA. Guide RNA is single-stranded RNA that includes an RNA sequence used as template by the CRISPR protein. Schematic diagram FIG. 9B illustrates how Csy4 targets and cleaves a hairpin in RNA of specific sequence.

Figure 10B:
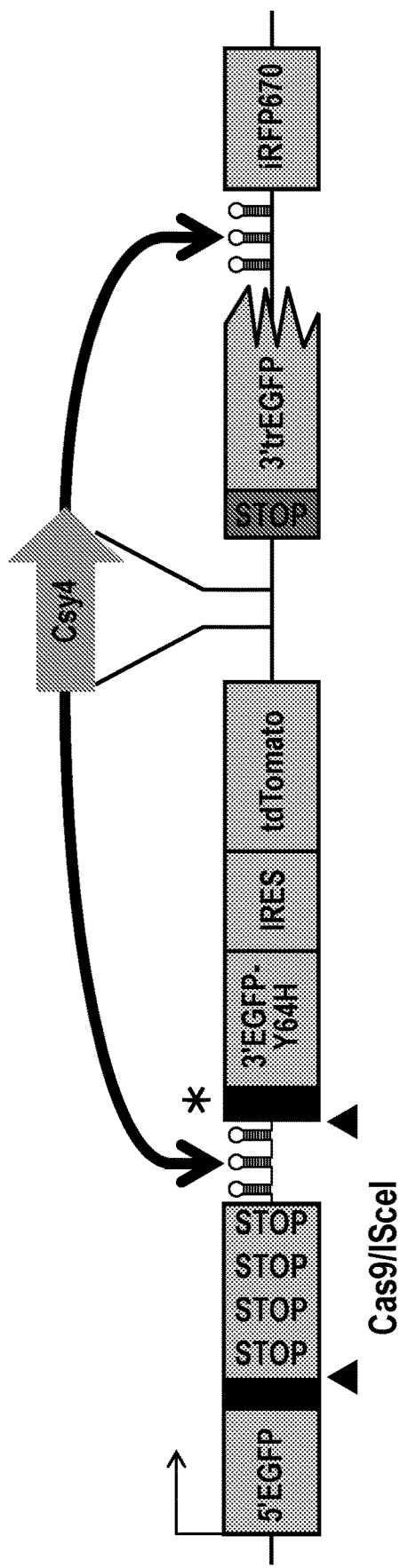
FIG. 10B is a schematic diagram of the nucleic acid reporter construct of FIG. 10A under naïve conditions when there is no I-SceI activity and no DNA repair.

FIG. 10B is a is a schematic diagram that represents the FluoMultiCsy4 reporter in naïve conditions wherein DNA repair has not been initiated by I-SceI. In this state, Csy4 is being continually expressed and will target and destroy spurious run-through transcripts. Since both the polycistronic tdTomato transcript and the polycistronic iRFP transcript mRNA harbor the specific Csy4-targeting hairpin sequence, both transcript mRNAs will be destroyed. The transcripts will not be translated, eliminating tdTomato and iRFP reporter protein fluorescent signal that occurs as background signal.

Figure 10C:
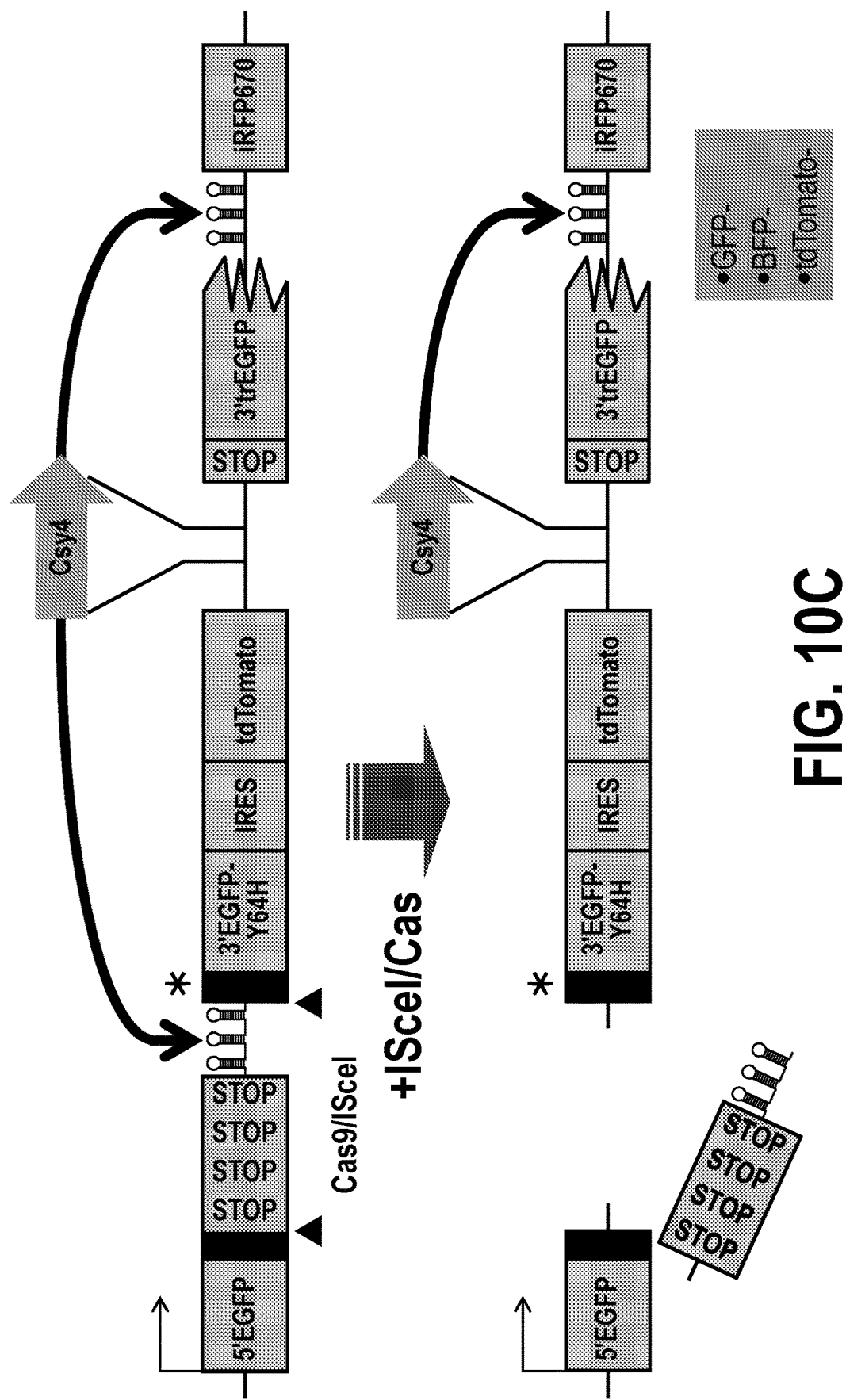
FIG. 10C is a schematic diagram of the nucleic acid reporter construct of FIG. 10A before and after contact with I-SceI, Cas9, or AsiSI endonuclease.

FIG. 10C is a schematic diagram that delineates the I-SceI (or alternatively AsiSI or Cas9) enzyme cutting of the FluoMultiCsy4 reporter. This enzyme-cutting event removes the section of the reporter containing both the polyadenylation transcriptional stop elements and the sequence for the Csy4 associated RNA hairpins.

Figure 10D:
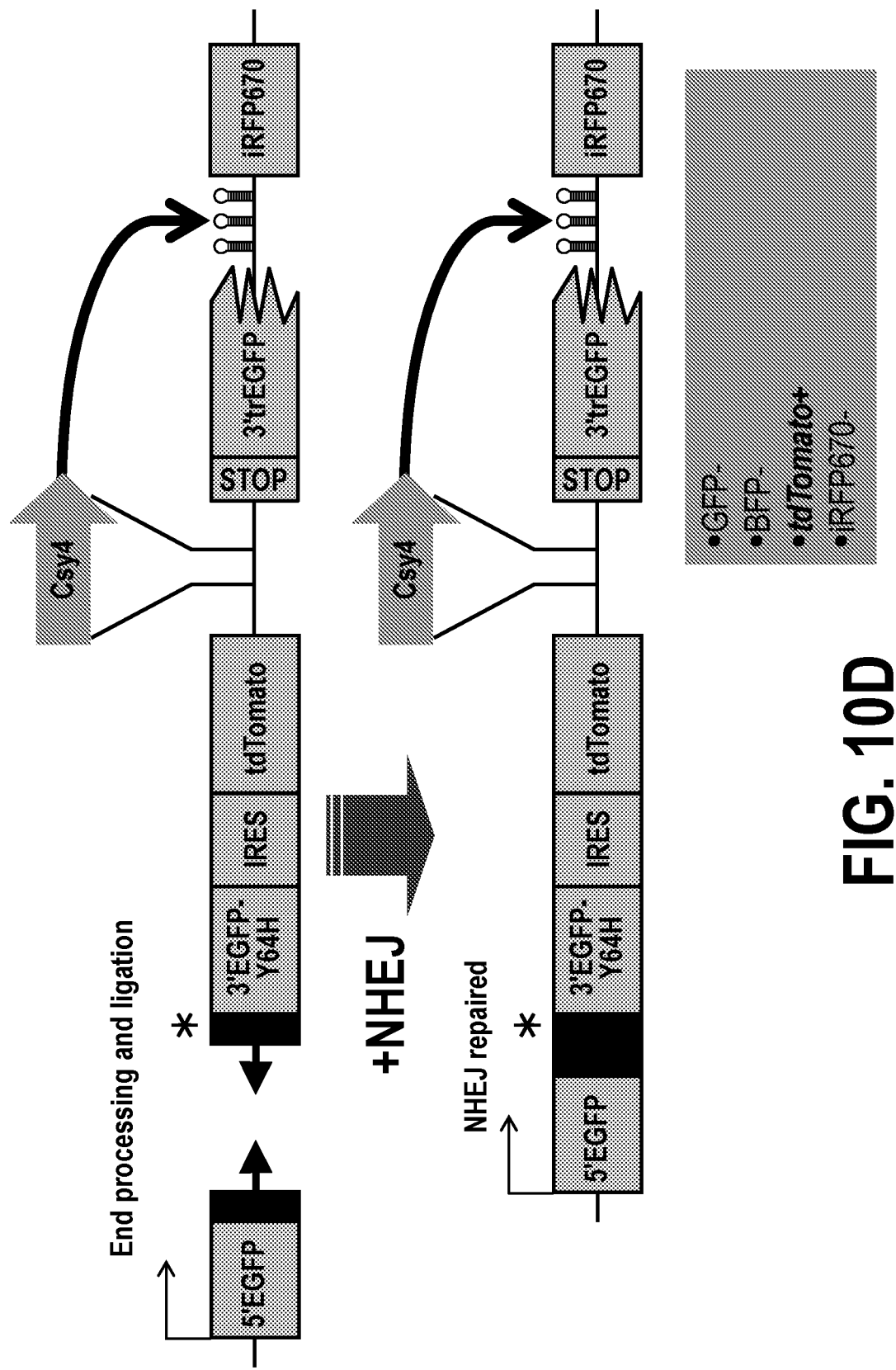
FIG. 10D is a schematic diagram of the nucleic acid reporter construct of FIG. 10C before and after repair by the NHEJ repair pathway.

As shown in FIG. 10D, NHEJ repair allows for translation and expression of only the full tdTomato reporter protein. During NHEJ, the ends of the double-stranded break are ligated together directly (see arrows on ends of the microhomology domains on the top construct). Following the removal of the termination cassette and direct ligation, the transcribed RNA is no longer terminated before transcription of the IRES, and tdTomato protein is expressed. None of the other reporters are expressed at full-length and/or in-frame. Since the Cys4 associated RNA hairpin encoding sequence 5' to tdTomato was removed by the I-SceI cutting enzyme, the tdTomato transcript is not targeted for destruction by Csy4. Alternatively, the Csy4-associated RNA hairpin-encoding sequence remains present 5' to the iRFP670 reporter protein. Ongoing expression of Csy4 causes the destruction of iRFP670 transcript. Therefore, only tdTomato fluorescence signal is present when NHEJ repair occurs.

Figure 10E:
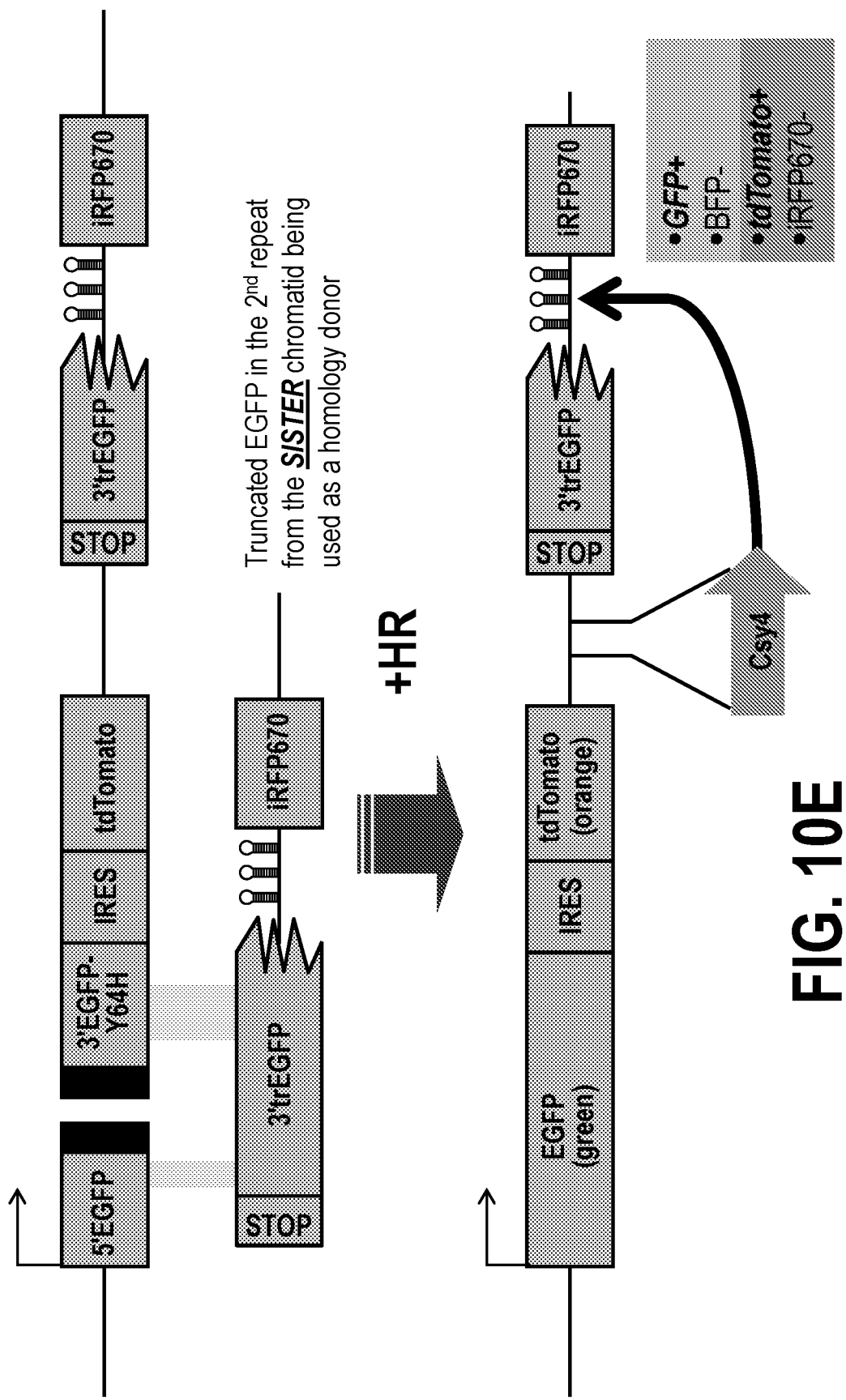
FIG. 10E is a schematic diagram of the nucleic acid reporter construct of FIG. 10C before and after repair by the HR repair pathway.

As shown in FIG. 10E, HR repair allows for translation and expression of GFP and tdTomato. After the DSB has been made in the construct, the 5'EGFP-B portion of the construct from a sister chromatid is used to repair the break. The 5'EGFP-B has homology to both the 5'EGFP-A and the 3'EGFP-Y64H (see gray arrows indicating homologous regions). When the HR repair process is complete, the repaired sequence is that of a full-length EGFP. Both full-length EGFP (green fluorescence) and tdTomato (orange fluorescence) are expressed. Since the Cys4 associated RNA hairpin encoding sequence 5' to tdTomato was removed by the I-SceI cutting enzyme, the EGFP/tdTOMATO bicistronic transcript is not targeted for destruction by Cys4.

Alternatively, the Cys4 associated RNA hairpin-encoding sequence remains 5' to the iRFP670 reporter protein. Ongoing expression of Csy4 causes the destruction of iRFP670 transcript. Therefore, tdTomato and GFP fluorescence signal are present when HR repair occurs.

Figure 10F:
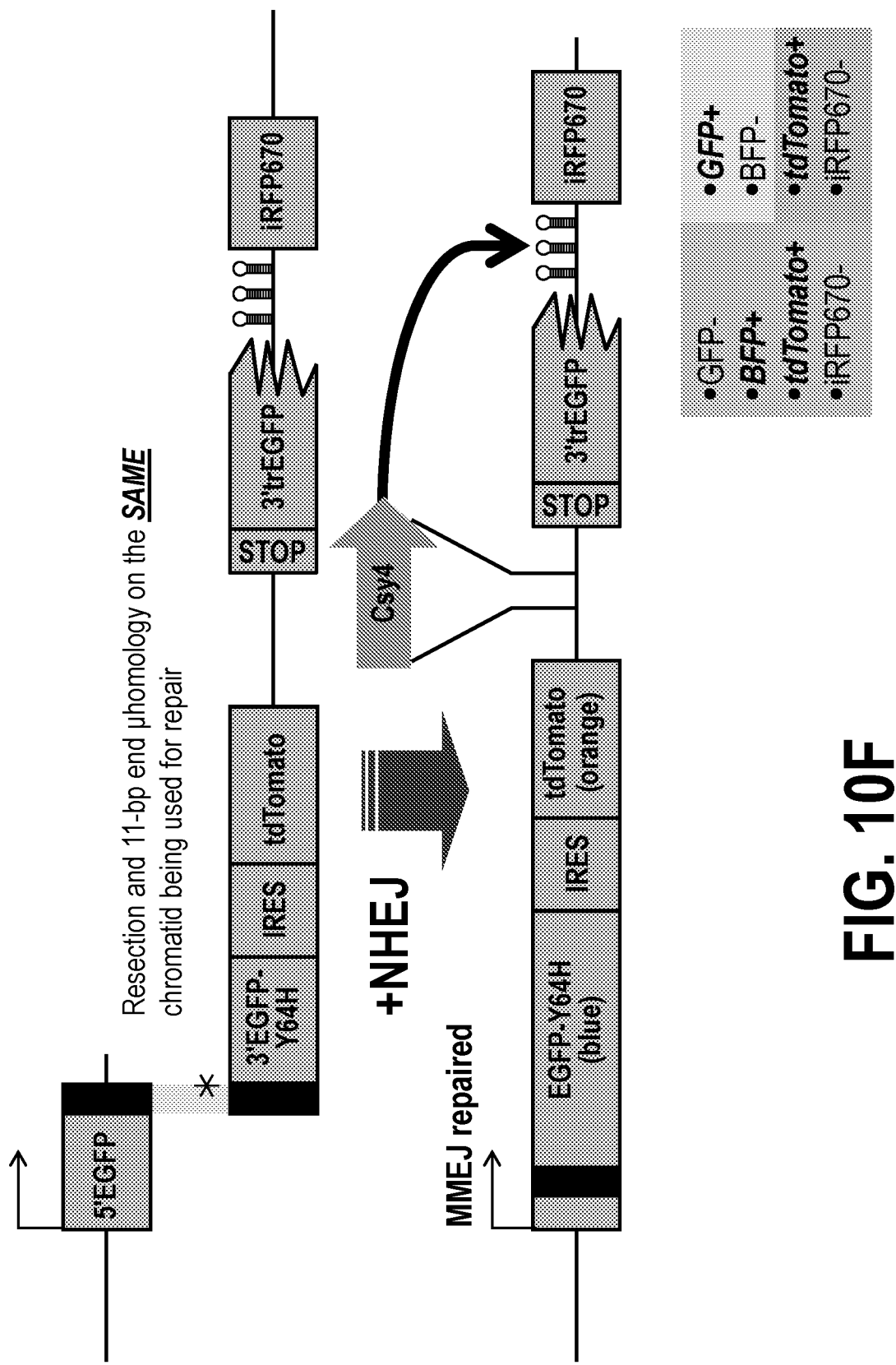
FIG. 10F is a schematic diagram of the nucleic acid reporter construct of FIG. 10C before and after repair by the MMEJ repair pathway.

As shown in FIG. 10F, MMEJ repair allows for translation and expression of BFP and tdTomato. During the MMEJ repair process, the microhomology domains (labeled "u") on each end of the broken chromatid recombine (see gray arrow between the MHD on each end of the break) and the ends of the break are ligated together, leaving a single microhomology domain. This leaves the 5'EGFP-A in the same reading frame as the 3'EGFP-Y64H, allowing expression of a full-length EGFP-Y64H protein and a full-length tdTomato protein. The full-length EGFP-Y64H has the signaling properties of blue fluorescent protein (BFP). Since the Cys4-associated RNA hairpin encoding sequence 5' to tdTomato was removed by the I-SceI cutting enzyme, the EGFP-Y64H/tdTOMATO bicistronic transcript is not targeted for destruction by Cys4.

Alternatively, the Cys4-associated RNA hairpin-encoding sequence remains 5' to the iRFP670 reporter protein. Ongoing expression of Csy4 causes the destruction of iRFP670 transcript. Therefore, tdTomato and BFP fluorescence signal are present when MMEJ repair occurs.

Figure 10G:
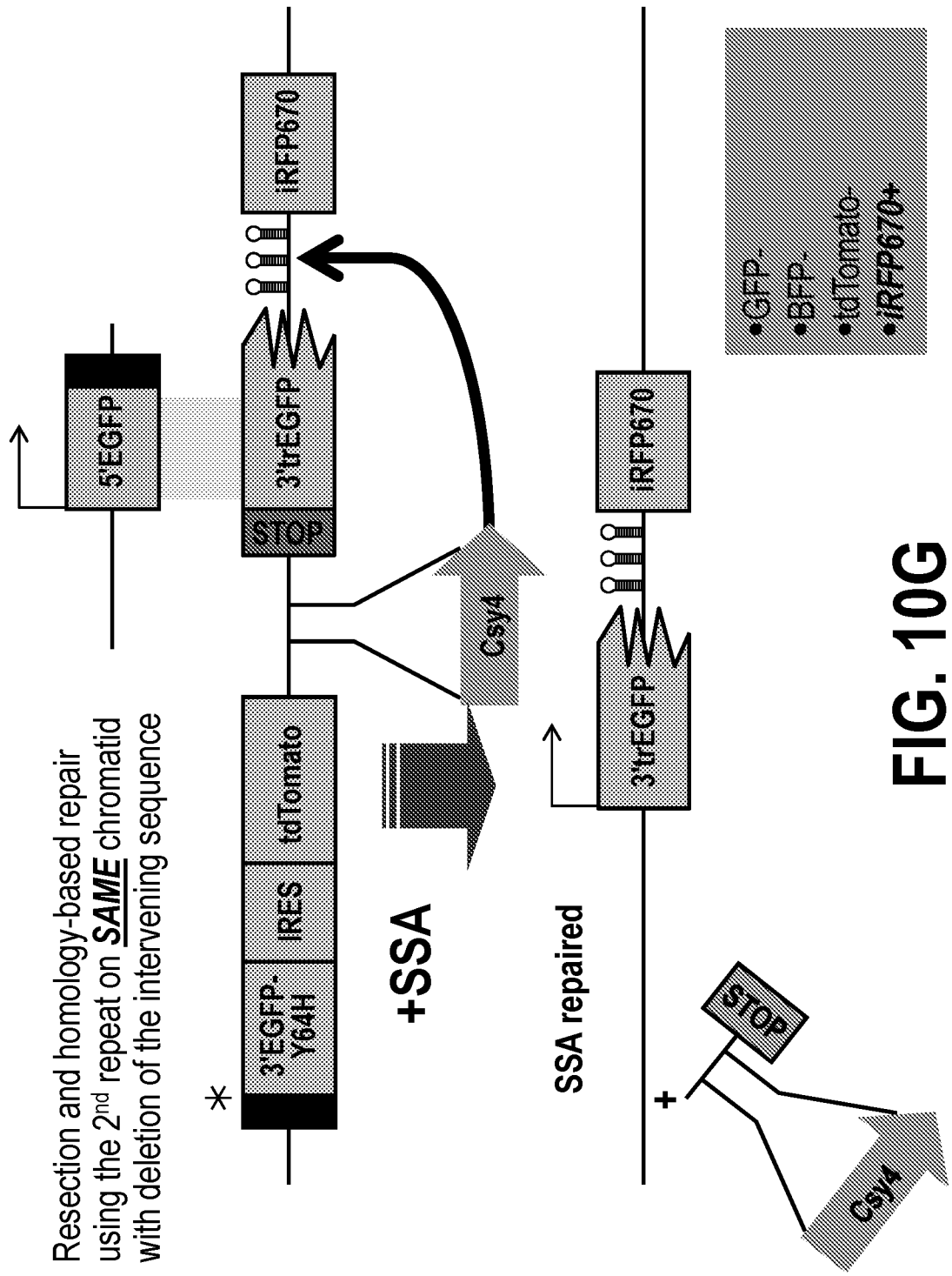
FIG. 10G is a schematic diagram of the nucleic acid reporter construct of FIG. 10C before and after repair by the SSA repair pathway.

As shown in FIG. 10G, SSA repair allows for translation and expression of iRFP. The 5'EGFP-A is annealed with homologous sequence of 5'EGFP-B on the same chromatid. The promoter associated with the 5'EGFP-A drives expression of the iRFP670 protein, which fluoresces maroon. The section of chromatid containing the 3'EGFP-Y64H, the IRES, and the tdTomato is deleted; thus no other fluorescent proteins are retained in the repaired construct. Furthermore, the expression cassette for Csy4 has also been removed in the final repair product. Therefore, iRFP is expressed despite having the Csy4 associated RNA hairpin, because Csy4 is no longer being expressed. Thus, iRFP fluorescence signal is present when SSA repair occurs.

The efficacy of the FluoMultiCsy4 reporter was tested to compare the fluorescent signal observed in cells with forced expression of I-SceI versus control cells without an endonuclease. Plasmids containing the FluoMultiCsy4 reporter were transfected into 293T cells. Clones which integrated a single copy of the FluoMultiCsy4 reporter at a random location in their genome were selected (A2, A7, B10, and B12). These clones were infected with either an empty virus or an ISceI-encoding virus. The fluorescent signal of the cells was then determined by FACs (counting 100,000 cells).

Figure 11A:
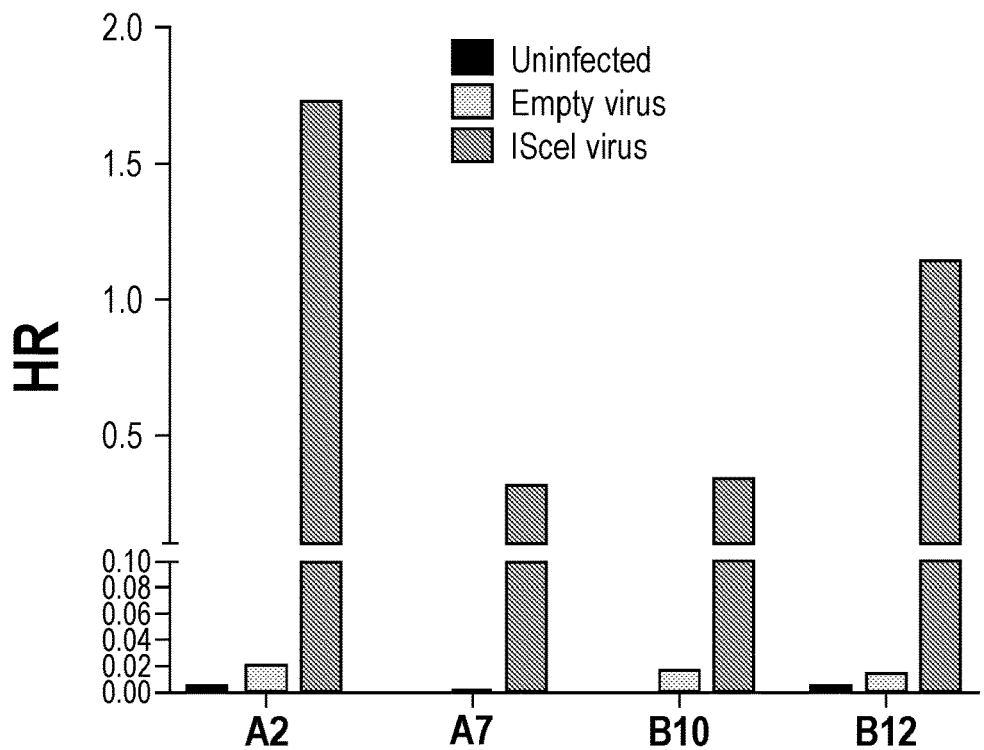
FIGS. 11A-D are a set of histograms depicting detection of four different fluorescent reporter proteins in 293T cells transiently transfected with the nucleic acid reporter construct of FIG. 10A. The 293T cells were either uninfected or infected with an empty virus or an I-SceI encoding virus. Data is shown for 293T cell clones A2, A7, B10, and B12.
Figure 11B:
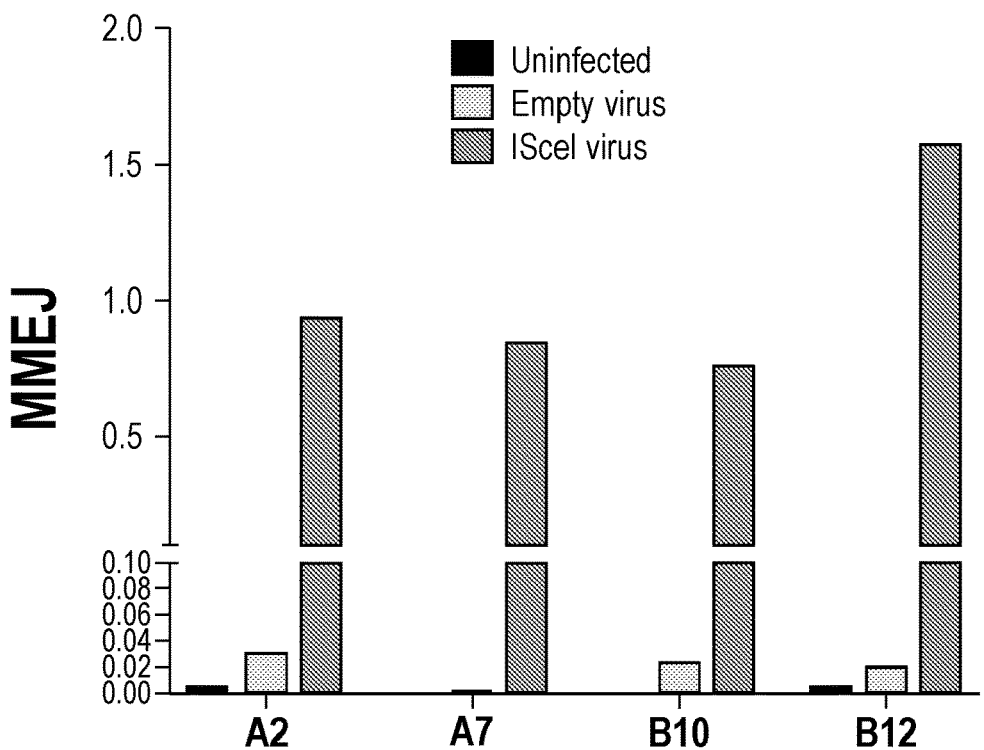
Figure 11C:
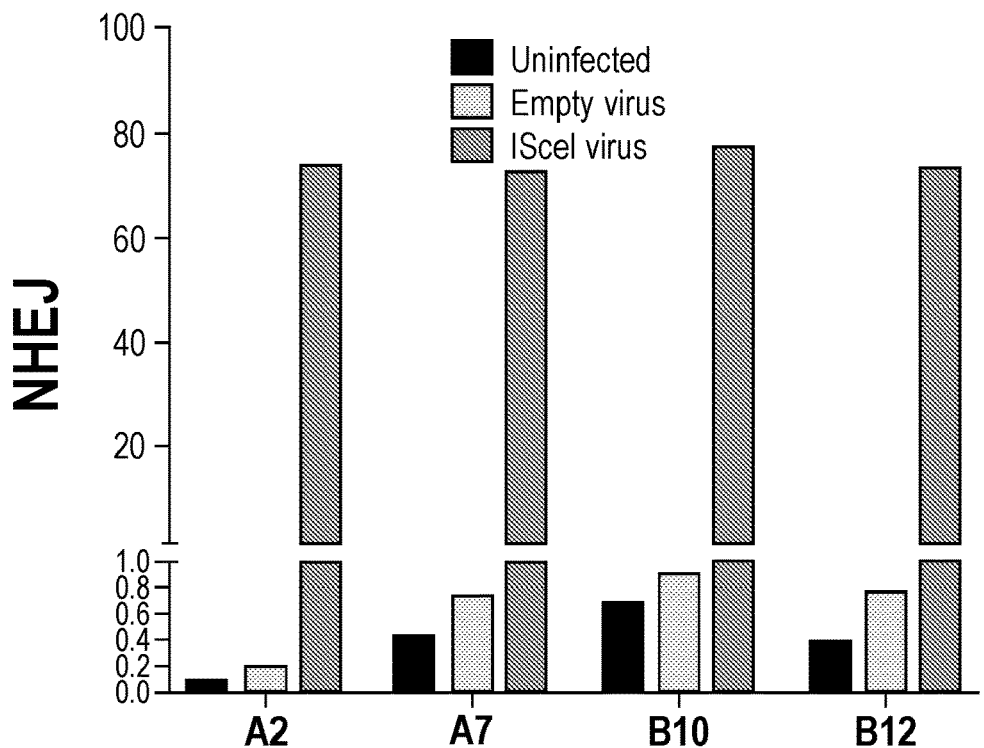
Figure 11D:
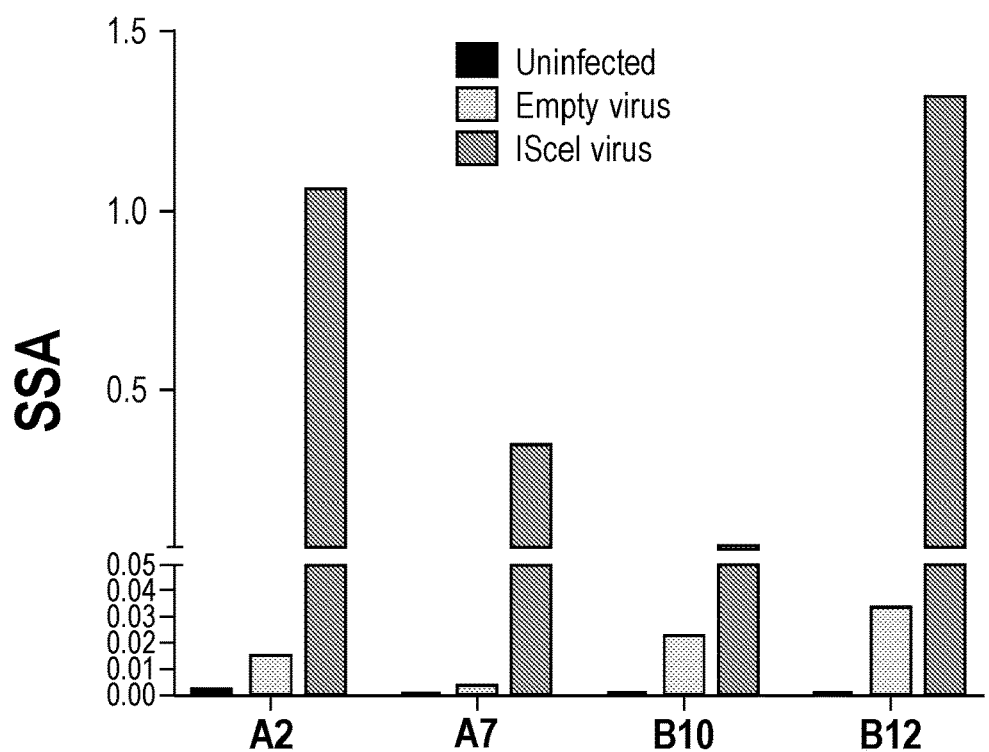

FIGS. 11A-D are a set of histograms that display the percentage of cells counted with a fluorescent signal indicative of HR (FIG. 11A), MMEJ (FIG. 11B), NHEJ (FIG. 11C), or SSA (FIG. 11D). Data is presented for cells infected with ISceI-encoding virus, as well as, uninfected and empty virus controls. The vast majority of the cells that displayed DNA repair used the NHEJ repair mechanism, confirming that NHEJ is the pathway of (double-strand break repair) DSBR most frequently utilized by mammalian cells.

Color-Sorted Cells Harbor the Predicted Repair Products

Figure 12A:
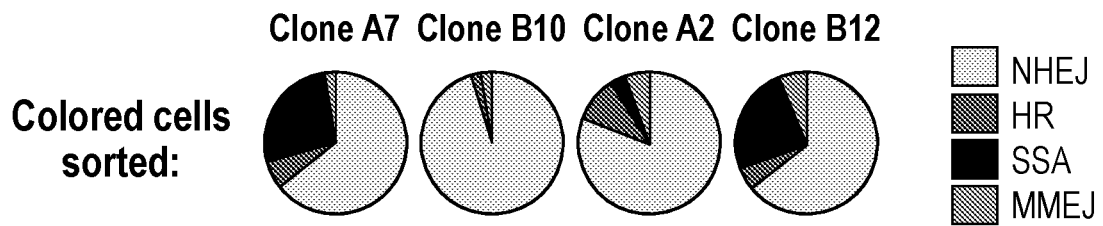
FIGS. 12A-B depict verification that the repair pathway indicated by the emission of a particular fluorescent reporter protein matches the repair pathway indicated based on DNA analysis of the cell. The 293T cells were infected with an I-SceI encoding virus.
Figure 12B:
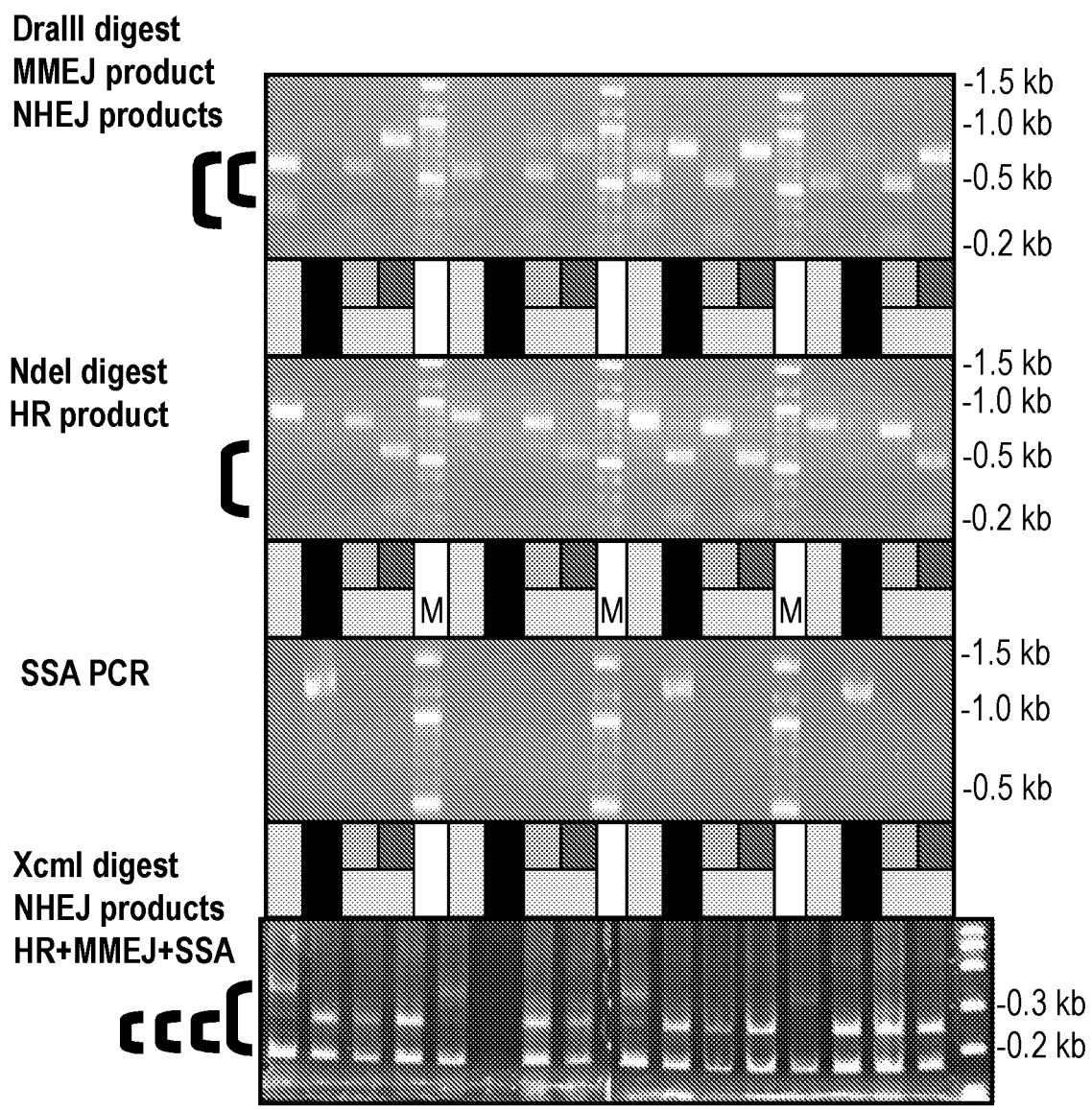

FIGS. 12A-B show the results of experiments performed to determine whether the expected repair products for each different pathway would match the colors that the cells emit. 293T cell clones A2, A7, B10, and B12, which have one copy of the FluoMultiCsy4 reporter integrated into their genome, were infected with an ISceI-encoding virus. As shown in FIG. 12A, the cells were FACS-sorted according to the different colors that they displayed. Genomic DNA was extracted from these color-sorted cells with the purpose of analyzing the repair products formed. The DSB reporter construct was designed with silent mutagenesis to create unique restriction sites in the repair products of each distinct pathway. Repair products from the genomic DNA of the color-sorted cells were PCR-amplified and digested with the appropriate restriction enzymes. For example, in the case of SSA, the PCR product is only amplified when repair by SSA occurs.

The results of these genomic experiments are shown in FIG. 12B. These results indicate that each expected repair product or digested repair product is only detected significantly in the cells that were sorted by color for that specific type of repair. For example, the SSA repair product only amplifies in the gDNA of cells that are sorted for the maroon color, the expected color for SSA, whereas the same PCR product is not detectable in clone B10, which is consistent with almost no cells utilizing SSA for DSB repair.

The Effect of Depletion of Selected DNA Repair Factors on DSB Repair Pathway Choices This experiment examines whether depletion of DNA repair pathway proteins can affect the corresponding repair pathway in ways that are detectable by the FluoMultiCsy4 reporter system assay.

Figures 13C, 13D:
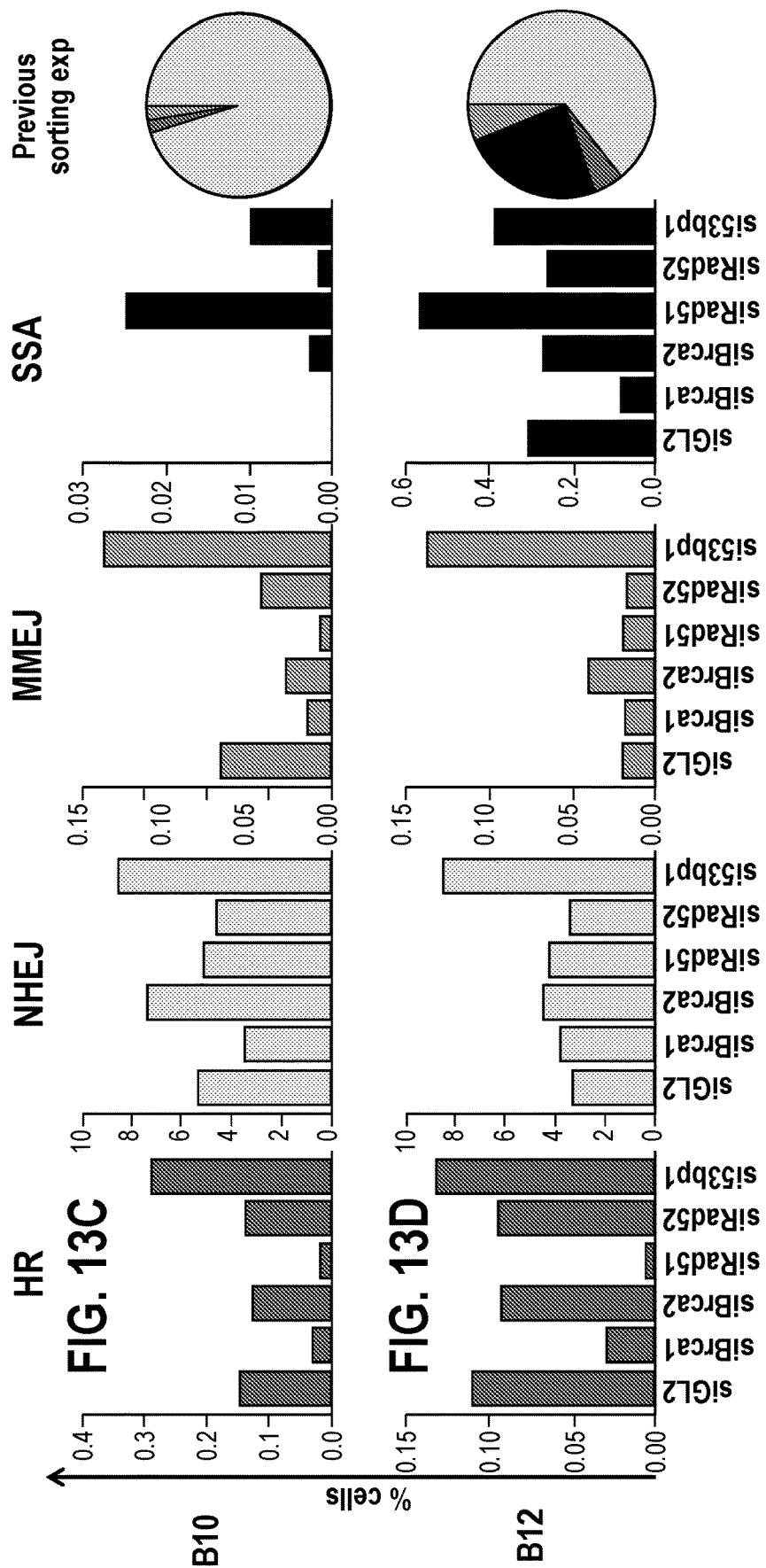
Figure 14A:
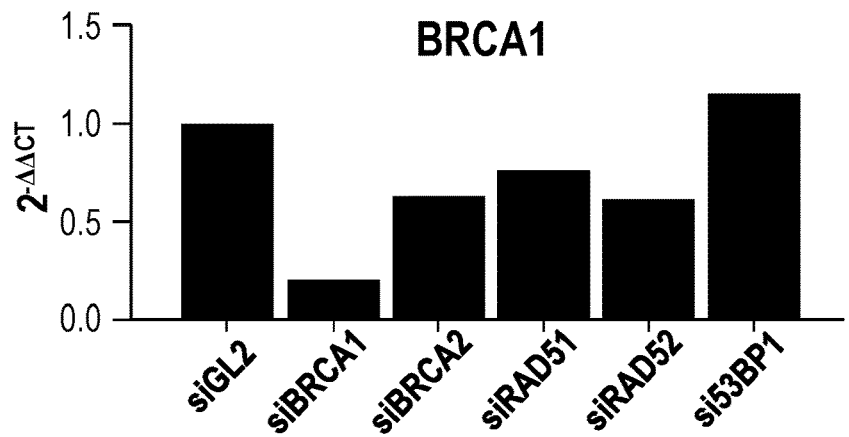
FIGS. 14A-E are a set of histograms depicting the depletion of BRCA1 (FIG. 14A), BRCA2 (FIG. 14B), RAD51 (FIG. 14C), RAD52 (FIG. 14D), or 53BP1 (FIG. 14E) RNA in the presence of tested siRNA molecules used to treat 293T cell clone A2 as determined by qPCR. Decrease in RNA is depicted as a fold difference between treated relative to untreated.
Figure 14B:
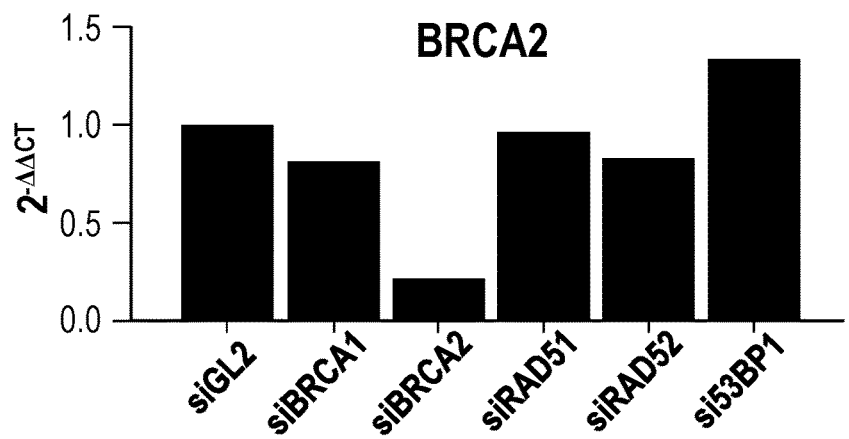
Figure 14C:
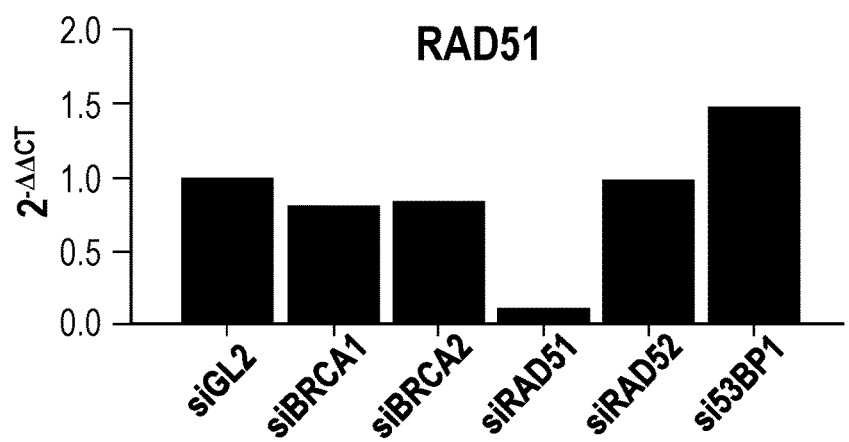
Figure 14D:
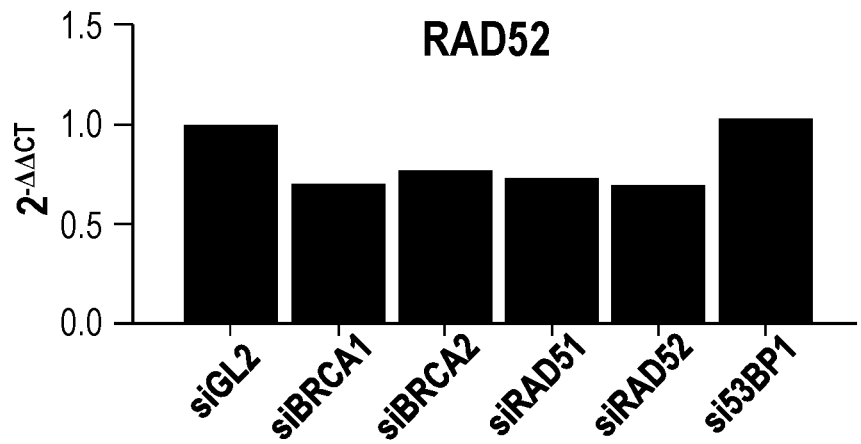
Figure 14E:
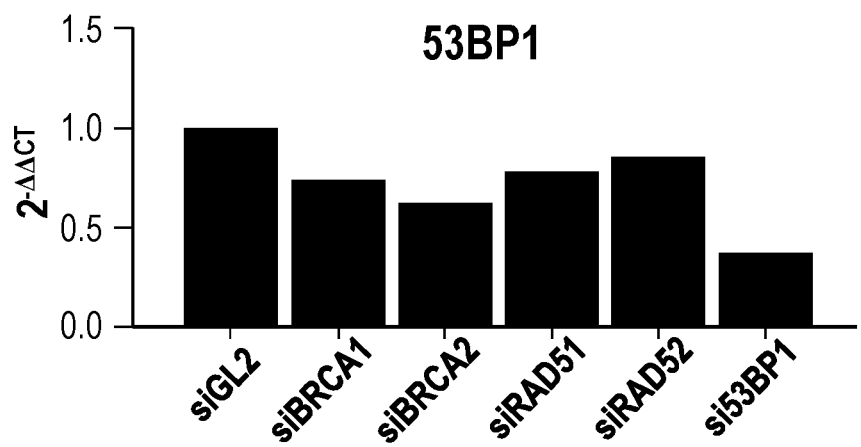
Figure 15A:
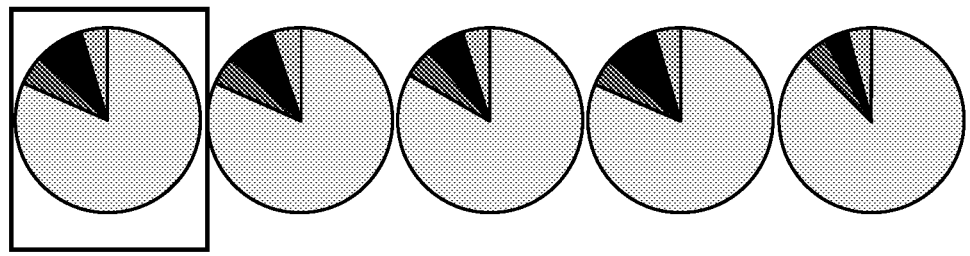
FIGS. 15A-D are a set of pie charts depicting the percent detection of four different fluorescent reporter proteins (corresponding to NHEJ, HR, SSA, and MMEJ repair mechanisms, respectively) in subclones of cell clones A2 (FIG. 15A), A7 (FIG. 15B), B10 (FIG. 15C), and B12 (FIG. 15D).
Figure 15A:
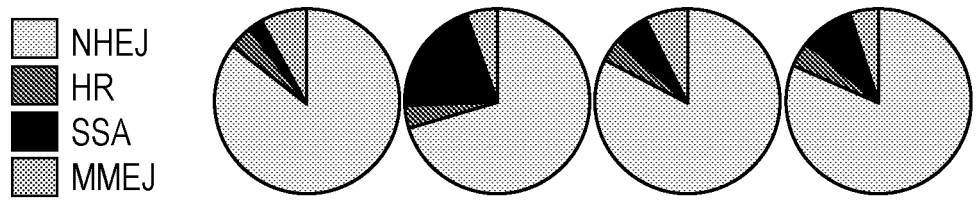
Figure 15B:
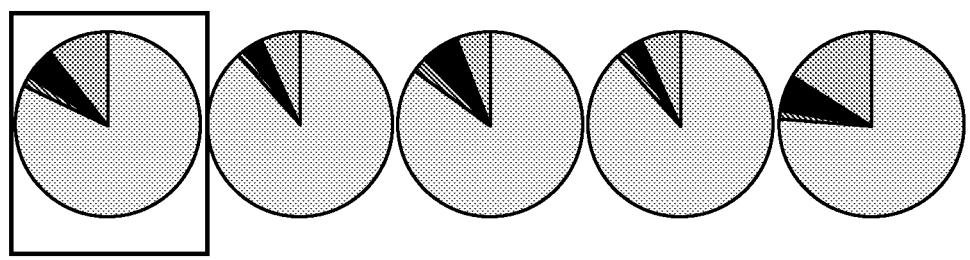
Figure 15B:
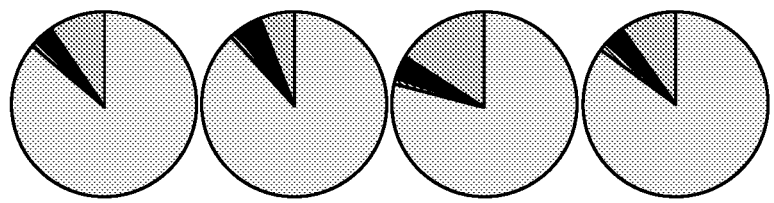
Figure 15C:
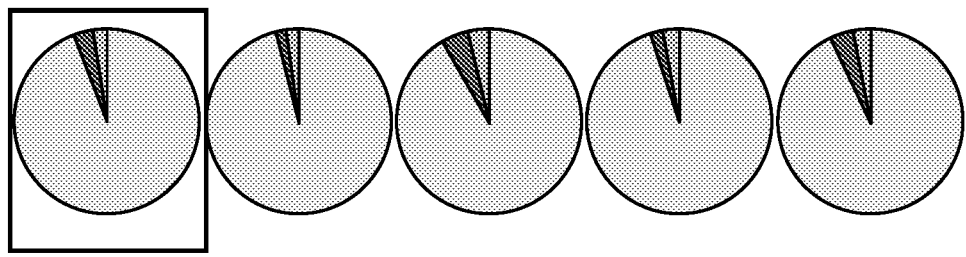
Figure 15C:
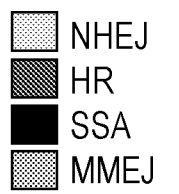
Figure 15D:
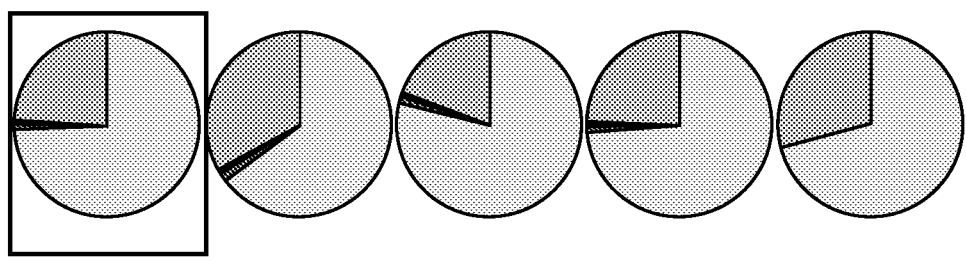
Figure 15D:
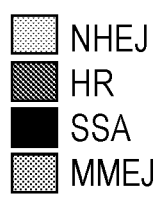

The A2 (FIG. 13A), A7 (FIG. 13B), B10 (FIG. 13C), and B12 (FIG. 13D) clones were infected with ISceI-encoding virus. Next, the cells were transfected with siRNAs targeted at depleting either BRCA1, BRCA2, Rad51, Rad52 or 53BP1. Cells were also transfected with an siRNA control, siGL2, that targets a gene irrelevant to the DNA repair pathways.

FIG. 13 shows the percentage of cells that displayed HR, NHEJ, MMEJ, and SSA repair in the presence of knockdown of the respective DNA repair pathway genes in each of the four clones tested. Depletion of Rad51 leads to an obvious drop in the proportion of HR repair, albeit more or less dramatically depending on the clone analyzed. A less strong but reproducible effect can be detected in MMEJ repair when Rad51 is depleted.

In order to validate the results shown in FIG. 13, the efficiency of siRNA knockdown of BRCA1, BRCA2, Rad51, Rad52, 53BP1, or control protein GL2 was determined. FIGS. 14A-E display the knockdown efficiency of these proteins in the presence of the sRNAs siGL2, siBRCA1, siBRCA2, siRad51, siRad52, or si53BP1. The depletion of the RNA of the relevant protein, BRCA1 (FIG. 14A), BRCA2 (FIG. 14B), Rad51 (FIG. 14C), Rad52 (FIG. 14D), or 53BP1 (FIG. 14E) as determined by qPCR. The change in the quantity of RNA is depicted as a fold difference between treated relative to untreated. With the exception of Rad52, most knockdowns depleted more than 60% of their corresponding targets.

The Choice of a DNA Repair Mechanism is Consistent in Subclones of the Original Clones In order to determine the consistency and reproducibility of the repair pathway choice readouts, subclones were isolated of each original cell clone. Each independent cell clone naturally displays different ratios of repair pathway "preferences" (because in each clone the reporter is integrated in a different genomic location and each one of those locations are probably repaired differently). Therefore, determining the occurrence of different repair pathways in subclones is indicative of how reproducible and/or how stochastic the readouts of DNA repair pathways detected are.

As shown in FIGS. 15A-D, once the subclones were isolated, the DNA repair process was initiated using I-SceI in the subclones, as well as, the original clone. The clones, and respective subclones, of A2 (FIG. 15A), A7 (FIG. 15B), B10 (FIG. 15C), and B12 (FIG. 15D) were analyzed using FACs (counting 100,000 cells). The results from the original parental clone are shown as boxed. The repair choice profiles of the subclones are largely comparable to their respective parental clone, underscoring the robustness and reproducibility of this method.

Figure 16A:
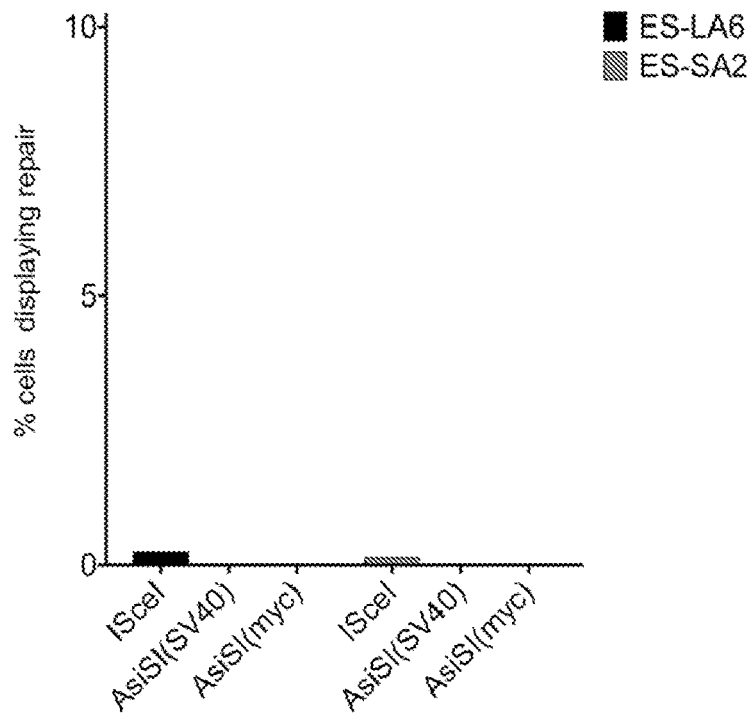
FIGS. 16A-C are a set of histograms depicting the percentage of mouse ES cells (FIG. 16A), 293T cells (FIG. 16B), or T98G cells (FIG. 16C) or that undergo DNA repair when infected with an I-SceI encoding virus or an AsiSI encoding virus.
Figure 16B:
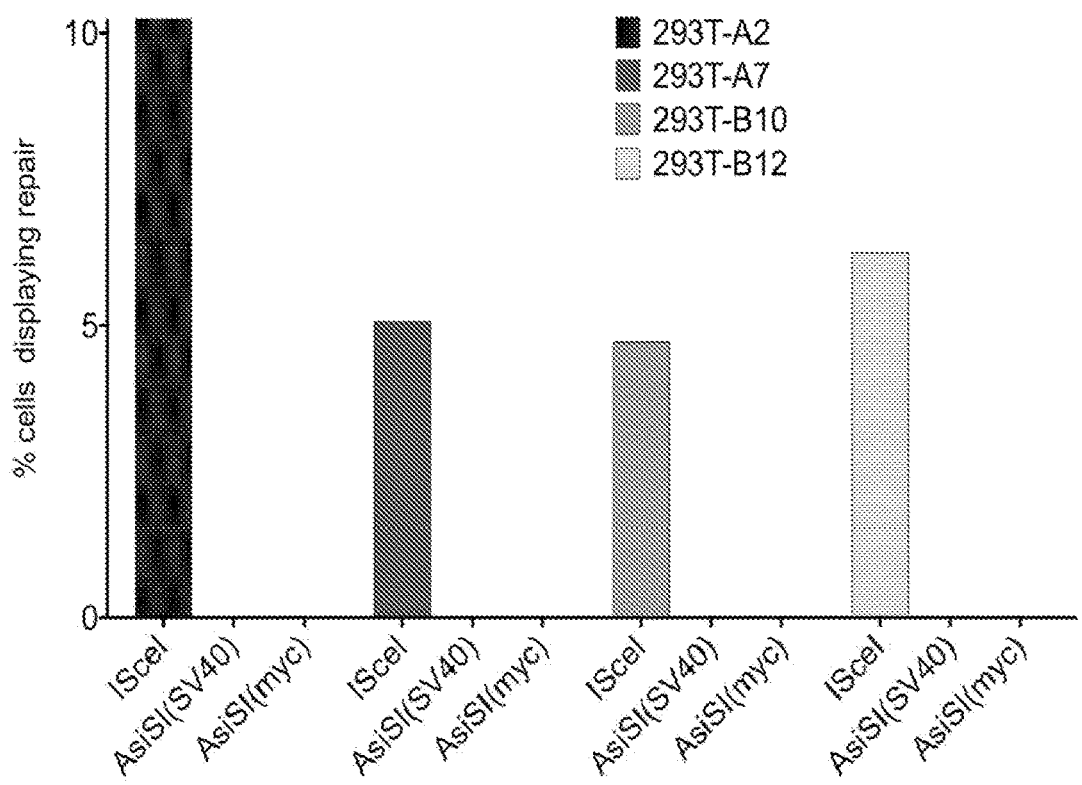
Figure 16C:
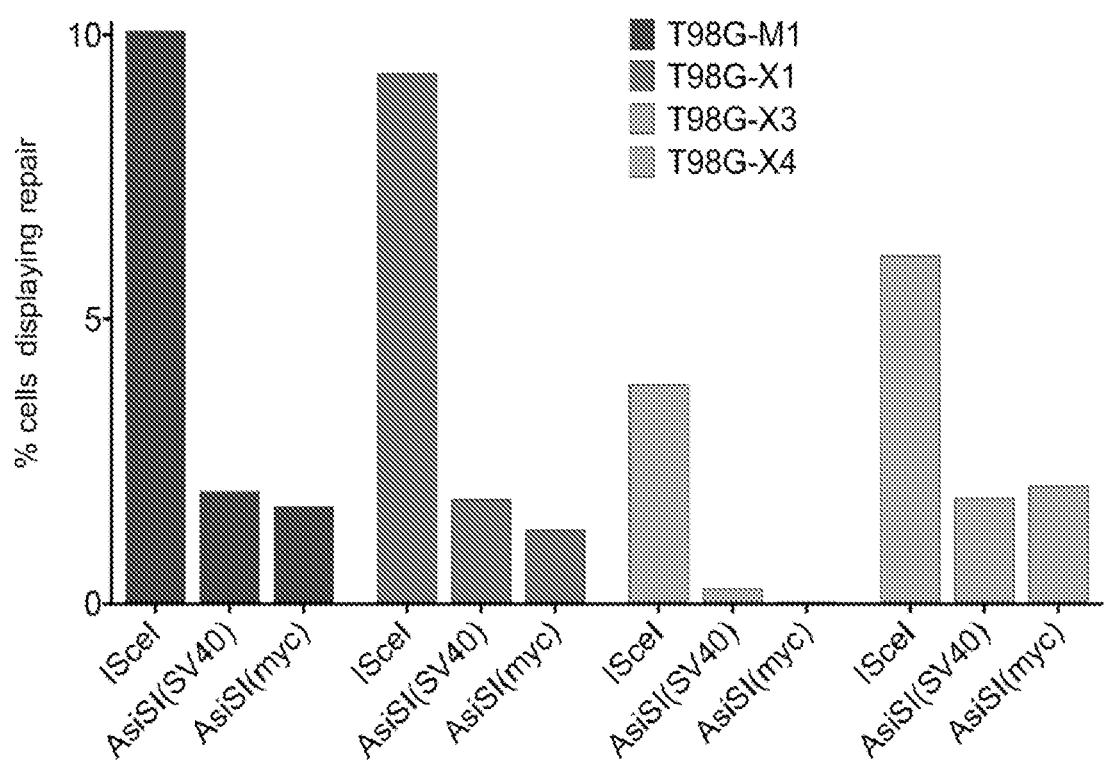

Efficiencies of Different Endonucleases in Different Cell Types on the Percentage of Cells Displaying Repair FIGS. 16A-C show the efficiency of endonucleases I-SceI and AsiSI to induce DNA repair in mouse ES cells (FIG. 16A), 293T cells (FIG. 16B), or T98G cells (FIG. 16C). Clones which integrated a single FluoMultiCsy4 reporter were isolated from 293 Ts, T98Gs and mouse ES cells. These cells were infected with either 3×SV40nls.ISceI-, 3×SV40nls.AsiSI- or 3×MYCnls.AsiSI-encoding viruses, alongside an appropriate empty vector control (not shown). Cells were selected with Puromycin. The cells that displayed DNA repair (any of the four pathways) where counted by FACS (all colored cells were counted). The relative efficiency of endonuclease cutting of the respective enzymes was judged by the number of cells that displayed repair resulting from ectopic expression of the respective enzymes.

This data indicates that repair can be triggered by cleavage at the appropriate cut sites on the reporter with different enzymes including I-SceI and AsiSI (albeit in a cell type-specific manner).

The foregoing description is intended to illustrate but not to limit the scope of the disclosure, which is defined by the scope of the appended claims. Other embodiments are within the scope of the following claims.

What is claimed is:

1. A nucleic acid comprising from 5' to 3':
   (a) a first cassette comprising:
      a 5' portion of an open reading frame of a first reporter gene (5'RP1);
      a first microhomology domain (MHD);
      a sequence comprising from 5' to 3': a first double-stranded endonuclease recognition sequence (DSE-RS) recognized by a first double-stranded endonuclease (DSE), one or more transcriptional terminators, and a second DSE-RS recognized by a second DSE;
      a second MHD that has sequence homology to the first MHD; and
      a 3' portion of an open reading frame for an allele of the first reporter gene (3'RP1),
      wherein a complete open reading frame of the first reporter gene (RP1) comprises from 5' to 3': 5'RP1, the first MHD or the second MHD, and 3'RP1,
      wherein removal of the sequence between the cleavage site in the first DSE-RS and the cleavage site in the second DSE-RS from the first cassette results in a reading frame shift of 3'RP1 relative to its native reading frame;
   (b) a second cassette comprising:
      an internal ribosome entry site sequence (IRES);
      an open reading frame of a second reporter gene (RP2) that is operably linked to the IRES;
   (c) a third cassette comprising a portion of an open reading frame of a third reporter gene (RP3), wherein the portion of RP3 comprises from 5' to 3':
      a first portion that has sequence homology to the 5'RP1; and
      a second portion that has sequence homology to the 3'RP1,
      wherein homologous recombination between the first and third cassettes results in a complete open reading frame of the third reporter gene comprising from 5' to 3': a 5' portion of the 5'RP1, the portion of RP3, and a 3' portion of the 3'RP1; and
   (d) a fourth cassette comprising an open reading frame of a fourth reporter gene (RP4) lacking a start codon,
      wherein the first and second cassettes are operably linked, and wherein the third and fourth cassettes are fused in the same reading frame.

2. The nucleic acid of claim 1:
   (a) comprising a linker nucleotide sequence encoding a cleavage site of a protease or a ribosomal skipping peptide, wherein the linker nucleotide sequence is located between the third cassette and the fourth cassette and is in the same reading frame as the third and fourth cassette;
  (b) wherein:
    (i) the RP1 gene product is capable of producing a first signal;
    (ii) the RP2 gene product is capable of producing a second signal;
    (iii) the RP3 gene product is capable of producing a third signal; and
    (iv) the RP4 gene product is capable of producing a fourth signal;
  (c) wherein a complete open reading frame of RP1 consists of from 5' to 3': 5'RP1, the first MHD or the second MHD, and 3'RP1;
  (d) further comprising a promoter sequence operably linked to the first cassette; and/or
  (e) wherein the third cassette does not comprise a start codon in the RP3 reading frame.

3. The nucleic acid of claim 1, wherein:
  (a) one or more of RP1, RP2, RP3, and RP4 are a fluorescent protein, optionally wherein each of RP1, RP2, RP3, and RP4 is a fluorescent protein;
  (b) RP1 encodes EGFP-Y64H, optionally wherein the EGFP-Y64H comprises the amino acid sequence of SEQ ID NO: 4;
  (c) RP3 encodes EGFP, optionally wherein the EGFP comprises the amino acid sequence of SEQ ID NO: 5;
  (d) RP2 encodes tdTomato, optionally wherein the tdTomato comprises the amino acid sequence of SEQ ID NO: 6;
  (e) RP4 encodes iRFP670, optionally wherein the iRFP670 comprises the amino acid sequence of SEQ ID NO: 7;
  (f) one or more of RP1, RP2, RP3, and RP4 are an enzyme that catalyzes a reaction with a substrate to produce an observable change in that substrate; and/or
  (g) the one or more transcriptional terminators are selected from the group consisting of: human actin beta (hACTB) terminator sequence, phosphoglucokinase (PGK) terminator sequence, simian virus 40 (SV40) terminator sequence, human growth hormone (hGH) terminator sequence, bovine growth hormone (bGH) terminator sequence, and rabbit beta-globin (rbGlob) terminator sequence.

4. The nucleic acid of claim 1, wherein the first and second DSE are the same DSE.

5. The nucleic acid of claim 1, wherein the first and/or second DSE is a rare-cutting endonuclease, optionally wherein the rare-cutting endonuclease is I-SceI or AsiSI.

6. The nucleic acid of claim 1,
  wherein the first DSE is an RNA-guided DNA endonuclease associated with a guide RNA comprising a nucleotide sequence complementary to the first DSE-RS, and/or
  the second DSE is an RNA-guided DNA endonuclease associated with a guide RNA comprising a nucleotide sequence complementary to the second DSE-RS.

7. The nucleic acid of claim 6, wherein the RNA-guided DNA endonuclease is selected from the group consisting of spCas9, saCas9, and Cpf1 and/or wherein the first and/or the second DSE-RSs comprise a protospacer adjacent motif (PAM) sequence.

8. The nucleic acid of claim 1, wherein:
  (a) the first DSE is a transcription activator-like nuclease (TALEN) or a zinc finger nuclease;
  (b) the second DSE is a transcription activator-like nuclease (TALEN) or a zinc finger nuclease;
  (c) the first and/or the second DSE-RSs comprise a nucleotide sequence of low frequency in a genome;
  (d) the first and second cassettes comprise SEQ ID NO: 2;
  (e) the third and fourth cassettes comprise SEQ ID NO: 3; and/or
  (f) wherein the nucleic acid sequence comprises SEQ ID NO: 1.

9. The nucleic acid of claim 1, wherein the transcriptional terminators of the first cassette comprise polyadenylation signal sequences.

10. The nucleic acid of claim 9, wherein:
  (a) the transcriptional terminators comprise four polyadenylation signal sequences, optionally wherein the nucleic acid sequence comprises an additional three polyadenylation signal sequences not within the first cassette;
  (b) the CRISPR-associated protein is Csy4; and/or
  (c) the open reading frame of the CRISPR-associated protein is located 3' to the RP2.

11. The nucleic acid of claim 9, wherein the first cassette further comprises a nucleic acid sequence that forms an RNA hairpin upon transcription or wherein the fourth cassette further comprises a nucleic acid sequence that forms an RNA hairpin upon transcription.

12. The nucleic acid of claim 11, wherein:
  (a) the nucleic acid sequence that forms the RNA hairpin upon transcription comprises sequence that is cleaved by the CRISPR-associated protein;
  (b) the nucleic acid sequence that forms the RNA hairpin upon transcription forms multiple hairpins;
  (c) the nucleic acid sequence that forms the RNA hairpin is located between the 5' portion of the first reporter gene and the 3' portion of the first reporter gene; and/or
  (d) the nucleic acid sequence that forms the RNA hairpin is located between the third reporter gene and fourth reporter gene.

13. The nucleic acid of claim 1, wherein the second cassette further comprises an open reading frame of a CRISPR-associated protein.

14. The nucleic acid of claim 1, wherein the nucleic acid sequence further comprises a fifth cassette comprising an additional reporter protein or proteins.

15. A vector comprising the nucleic acid of claim 1, and/or a nucleic acid having a sequence complementarity thereto.

16. An isolated cell comprising the vector of claim 15.

17. The isolated cell of claim 16, wherein the cell comprises a nucleic acid encoding the first DSE and/or the second DSE.

18. A method for detecting a type of double-stranded break repair mechanism in an isolated cell, comprising:
  (a) obtaining a cell comprising the vector of claim 15;
  (b) expressing in the cell the first DSE and the second DSE, thereby generating a double-stranded break; and
  (c) detecting one or more of the first, second, third, and/or fourth signals in response to the double-stranded break, wherein detection of a first, second, third, and/or fourth signal is indicative of a type of double-stranded break repair mechanism.

19. The method of claim 18, wherein:
  (a) detecting only the second signal indicates that the cell used non-homologous end joining (NHEJ) to repair the double-stranded break;
  (b) detecting only the second signal and the third signal indicates that the cell used homologous recombination (HR) to repair the double-stranded break;

(c) detecting only the first signal and the second signal indicates that the cell used microhomology-mediated end joining (MMEJ) to repair the double-stranded break;

(d) detecting only the fourth signal indicates that the cell used single-strand annealing (SSA) to repair the double-stranded break; and/or (e) the cell is a cancer cell, optionally wherein the cancer cell is from a cancer patient and/or the signal(s) from the cancer cell is detected in a tumor sample.

20. A method for detecting a type of double-stranded break repair mechanism in an isolated cell, comprising:

(i) integrating a nucleic acid sequence into the genome of a cell, wherein the nucleic acid sequence comprises at least four reporter genes that generate a different signal, wherein the nucleic acid comprises from 5' to 3':

(a) a first cassette comprising:
a 5' portion of an open reading frame of a first reporter gene (5'RP1);
a first microhomology domain (MHD);
a sequence comprising from 5' to 3': a first double-stranded endonuclease recognition sequence (DSE-RS) recognized by a first double-stranded endonuclease (DSE), one or more transcriptional terminators, and a second DSE-RS recognized by a second DSE;
a second MHD that has sequence homology to the first MHD; and
a 3' portion of an open reading frame for an allele of the first reporter gene (3'RP1),
wherein a complete open reading frame of the first reporter gene (RP1) comprises from 5' to 3': 5'RP1, the first MHD or the second MHD, and 3'RP1,
wherein removal of the sequence between the cleavage site in the first DSE-RS and the cleavage site in the second DSE-RS from the first cassette results in a reading frame shift of 3'RP1 relative to its native reading frame;

(b) a second cassette comprising:
an internal ribosome entry site sequence (IRES);
an open reading frame of a second reporter gene (RP2) that is operably linked to the IRES;

(c) a third cassette comprising a portion of an open reading frame of a third reporter gene (RP3), wherein the portion of RP3 comprises from 5' to 3':
a first portion that has sequence homology to the 5'RP1; and
a second portion that has sequence homology to the 3'RP1,
wherein homologous recombination between the first and third cassettes results in a complete open reading frame of the third reporter gene comprising from 5' to 3': a 5' portion of the 5'RP1, the portion of RP3, and a 3' portion of the 3'RP1; and (d) a fourth cassette comprising an open reading frame of a fourth reporter gene (RP4) lacking a start codon,
wherein the first and second cassettes are operably linked, and wherein the third and fourth cassettes are fused in the same reading frame;

(ii) inducing a double-stranded break into the nucleic acid sequence; and (iii) detecting at least one signal generated by at least one reporter gene, that signal being indicative of the type of double-stranded break repair mechanism,
wherein a different signal or combination of signals is detected for each of the double-stranded break repair mechanisms HR, NHEJ, MMEJ, and SSA.

* * * * *